(12) United States Patent
Junttila

(10) Patent No.: US 10,946,093 B2
(45) Date of Patent: Mar. 16, 2021

(54) METHODS OF TREATING CANCER USING PD-1 AXIS BINDING ANTAGONISTS AND MEK INHIBITORS

(71) Applicant: Genentech, Inc., South San Francisco, CA (US)

(72) Inventor: Melissa Junttila, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/399,118

(22) Filed: Jan. 5, 2017

(65) Prior Publication Data

US 2017/0112925 A1 Apr. 27, 2017

Related U.S. Application Data

(63) Continuation of application No. PCT/CN2015/040582, filed on Jul. 15, 2015.

(60) Provisional application No. 62/024,988, filed on Jul. 15, 2014.

(51) Int. Cl.
| | |
|---|---|
| *A61K 39/00* | (2006.01) |
| *A61K 39/395* | (2006.01) |
| *C07K 16/28* | (2006.01) |
| *A61K 31/4523* | (2006.01) |

(52) U.S. Cl.
CPC ...... *A61K 39/3955* (2013.01); *A61K 31/4523* (2013.01); *A61K 39/39558* (2013.01); *C07K 16/2803* (2013.01); *C07K 16/2827* (2013.01); *A61K 2039/505* (2013.01); *A61K 2039/542* (2013.01); *C07K 2317/52* (2013.01); *C07K 2317/56* (2013.01); *C07K 2317/72* (2013.01); *C07K 2317/73* (2013.01); *C07K 2317/76* (2013.01)

(58) Field of Classification Search
CPC ............ A61K 39/3955; A61K 31/4523; A61K 2039/505; C07K 16/2803; C07K 16/2827; C07K 2317/56; C07K 2317/76
See application file for complete search history.

(56) References Cited

U.S. PATENT DOCUMENTS

| | | | |
|---|---|---|---|
| 4,708,871 A | 11/1987 | Geysen | |
| 4,816,567 A | 3/1989 | Cabilly et al. | |
| 4,833,092 A | 5/1989 | Geysen | |
| 5,223,409 A | 6/1993 | Ladner et al. | |
| 5,403,484 A | 4/1995 | Ladner et al. | |
| 5,428,130 A | 6/1995 | Capon et al. | |
| 5,475,096 A | 12/1995 | Gold et al. | |
| 5,545,806 A | 8/1996 | Lonberg et al. | |
| 5,545,807 A | 8/1996 | Surani et al. | |
| 5,556,762 A | 9/1996 | Pinilla et al. | |
| 5,569,825 A | 10/1996 | Lonberg et al. | |
| 5,571,689 A | 11/1996 | Heuckeroth et al. | |
| 5,591,828 A | 1/1997 | Bosslet et al. | |
| 5,625,126 A | 4/1997 | Lonberg et al. | |
| 5,633,425 A | 5/1997 | Lonberg et al. | |
| 5,641,870 A | 6/1997 | Rinderknecht et al. | |
| 5,661,016 A | 8/1997 | Lonberg et al. | |
| 5,663,143 A | 9/1997 | Ley et al. | |
| 5,750,373 A | 5/1998 | Garrard et al. | |
| 6,075,181 A | 6/2000 | Kucherlapati et al. | |
| 6,150,584 A | 11/2000 | Kucherlapati et al. | |
| 6,982,321 B2 | 1/2006 | Winter | |
| 7,087,409 B2 | 8/2006 | Barbas, III et al. | |
| 7,491,829 B2 | 2/2009 | Laird et al. | |
| 8,217,149 B2 | 7/2012 | Irving et al. | |
| 9,724,413 B2 | 8/2017 | Maecker et al. | |
| 9,920,123 B2 | 3/2018 | Irving et al. | |
| 10,646,567 B2 | 5/2020 | Maecker | |
| 2009/0217401 A1 | 8/2009 | Korman | |
| 2010/0203056 A1 | 8/2010 | Irving | |
| 2011/0086837 A1 | 4/2011 | Belvin | |
| 2013/0034559 A1 | 2/2013 | Queva et al. | |
| 2014/0341902 A1* | 11/2014 | Maecker | A61K 39/39558 424/135.1 |
| 2016/0222117 A1 | 8/2016 | Irving et al. | |
| 2017/0107287 A1 | 4/2017 | Irving et al. | |
| 2018/0021431 A1 | 1/2018 | Maecker et al. | |

FOREIGN PATENT DOCUMENTS

| | | |
|---|---|---|
| CA | 2385412 A1 | 11/2002 |
| EP | 0 404 097 A2 | 12/1990 |
| JP | 2005-530709 A | 10/2005 |
| JP | 2006-340714 A | 12/2006 |
| JP | 2008-501631 A | 1/2008 |
| JP | 2008-544755 A | 12/2008 |
| JP | 2009-511490 A | 3/2009 |
| JP | 2009-527521 A | 7/2009 |

(Continued)

OTHER PUBLICATIONS

Bucheit et al, Biochemical Pharmacology 87:381-389, Published online Nov. 28, 2013 (Year: 2013).*
Ahmadzadeh, M. et al. "Tumor Antigen-Specific CD8 T Cells Infiltrating the Tumor Express High Levels of PD-1 and are Functionally Impaired," *Blood* 114(8):1537-1544, (Aug. 20, 2009).
Barbas III, C.F. et al. "In Vitro Evolution of a Neutralizing Human Antibody to Human Immunodeficiency Virus Type 1 to Enhance Affinity and Broaden Strain Cross-Reactivity," *Proc. Natl. Acad. Sci. USA* 91:3809-3813, (Apr. 1994).
Boerner, P. et al. "Production of Antigen-Specific Human Monoclonal Antibodies From in Vitro-Primed Human Splenocytes," *The Journal of Immunology* 147(1):86-95, (Jul. 1, 1991).

(Continued)

*Primary Examiner* — Lei Yao
(74) *Attorney, Agent, or Firm* — Morrison & Foerster LLP

(57) ABSTRACT

The present invention describes combination treatment comprising a PD-1 axis binding antagonist and a MEK inhibitor and methods for use thereof, including methods of treating conditions where enhanced immunogenicity is desired such as increasing tumor immunogenicity for the treatment of cancer.

24 Claims, 2 Drawing Sheets

Specification includes a Sequence Listing.

(56) References Cited

FOREIGN PATENT DOCUMENTS

| | | |
|---|---|---|
| JP | 2010-501585 A | 1/2010 |
| JP | 2010-536723 A | 12/2010 |
| JP | 2011-507889 A | 3/2011 |
| JP | 2011-512332 A | 4/2011 |
| JP | 2012-500652 A | 1/2012 |
| JP | 2012-500847 A | 1/2012 |
| JP | 2012-511329 A | 5/2012 |
| JP | 2013-512251 A | 4/2013 |
| TW | 201032822 A1 | 9/2010 |
| WO | WO-1984/03506 A1 | 9/1984 |
| WO | WO-1984/03564 A1 | 9/1984 |
| WO | WO-1991/10741 A1 | 7/1991 |
| WO | WO-1993/11161 A1 | 6/1993 |
| WO | WO-1996/33735 A1 | 10/1996 |
| WO | WO-1996/34096 A1 | 10/1996 |
| WO | WO-1998/24893 A2 | 6/1998 |
| WO | WO-2002/17952 A2 | 3/2002 |
| WO | WO-2002/17952 A3 | 3/2002 |
| WO | WO-2003/077914 A1 | 9/2003 |
| WO | WO-2004/42072 A2 | 5/2004 |
| WO | WO-2004/045617 A1 | 6/2004 |
| WO | WO-2004/092219 A2 | 10/2004 |
| WO | WO-2005/094376 A2 | 10/2005 |
| WO | WO-2005/094376 A3 | 10/2005 |
| WO | WO-2005/121142 A1 | 12/2005 |
| WO | WO-2006/121168 A1 | 11/2006 |
| WO | WO-2007/002325 A1 | 1/2007 |
| WO | WO-2007/002433 A1 | 1/2007 |
| WO | WO-2007/005874 A2 | 1/2007 |
| WO | WO-2007/044515 A1 | 4/2007 |
| WO | WO-2007/096259 A1 | 8/2007 |
| WO | WO-2008/024725 A1 | 2/2008 |
| WO | WO-2008/101840 A1 | 8/2008 |
| WO | WO-2009/021887 A1 | 2/2009 |
| WO | WO-2009/064675 A1 | 5/2009 |
| WO | WO-2009/073533 A2 | 6/2009 |
| WO | WO-2009/073533 A3 | 6/2009 |
| WO | WO-2009/085983 A1 | 7/2009 |
| WO | WO-2009/101611 A1 | 8/2009 |
| WO | WO-2009/111277 A1 | 9/2009 |
| WO | WO-2009/111278 A2 | 9/2009 |
| WO | WO-2009/111279 A1 | 9/2009 |
| WO | WO-2009/111280 A1 | 9/2009 |
| WO | WO-2009/114335 A2 | 9/2009 |
| WO | WO-2010/006225 A1 | 1/2010 |
| WO | WO-2010/027423 A2 | 3/2010 |
| WO | WO-2010/027423 A3 | 3/2010 |
| WO | WO-2010/027827 A2 | 3/2010 |
| WO | WO-2010/056735 A1 | 5/2010 |
| WO | WO-2010/077634 A1 | 7/2010 |
| WO | WO-2011/057222 A1 | 5/2011 |
| WO | WO-2011/060328 A1 | 5/2011 |
| WO | WO-2011/066342 A2 | 6/2011 |
| WO | WO-2011/066389 A1 | 6/2011 |
| WO | WO-2011/109400 A2 | 9/2011 |
| WO | WO-2011/109400 A3 | 9/2011 |
| WO | WO-2013/019906 A1 | 2/2013 |
| WO | WO2013019906 * | 2/2013 |
| WO | WO-2013/063001 A1 | 5/2013 |
| WO | WO-2014/151634 A1 | 9/2014 |
| WO | WO-2014/159835 A1 | 10/2014 |
| WO | WO-2014/195852 A1 | 12/2014 |
| WO | WO-2016/011160 A1 | 1/2016 |

OTHER PUBLICATIONS

Bretscher, P. and Cohn, M. et al. "A Theory of Self-Nonself Discrimination," *Science* 169:1042-1049, (Sep. 11, 1970).

Bretscher, P.A. "A Two-Step, Two-Signal Model for the Primary Activation of Precursor Helper T Cells," *Proc. Natl. Acad. Sci. USA* 96:185-190, (Jan. 1999).

Bruggemann, M. et al. "Designer Mice: The Production of Human Antibody Repertoires in Transgenic Animals," *Year Immunol.* 7:33-40, (1993).

Capel, J.A. et al. "Heterogeneity of Human IgG Fc Receptors," *Immunomethods* 4:25-34, (1994).

Chothia, C. and Lesk, A.M. "Canonical Structures for the Hypervariable Regions of Immunoglobulins," *J. Mol. Biol.* 196:901-917, (1987).

Clackson, T. et al. "Making Antibody Fragments Using Phage Display Libraries," *Nature* 352:624-628, (Aug. 15, 1991).

Cwirla, S.E. et al. "Peptides on Phage: A Vast Library of Peptides for Identifying Ligands," *Proc. Natl. Acad. Sci. USA* 87:6378-6382, (Aug. 1990).

Daëron, M. "Fc Receptor Biology," *Annu. Rev. Immunol.* 15:203-234, (1997).

Dankort. D. et al. "Braf$^{V600E}$ Cooperates with Pten Silencing to Elicit Metastatic Melanoma," *Nat. Genet.* 41(5):544-552, (May 2009).

De Haas, M. et al. "Fcγ Receptors of Phagocytes," *J. Lab Clin. Med.* 126(4):330-341, (Oct. 1995).

Fellouse, F.A. et al. "Synthetic Antibodies from a Four-Amino-Acid Code: A Dominant Role for Tyrosine in Antigen Recognition," *Proc. Natl. Acad. Sci. USA* 101(34):12467-12472, (Aug. 24, 2004).

Fishwild, D.M. et al. "High-Avidity Human IgGk Monoclonal Antibodies from a Novel Strain of Minilocus Transgenic Mice," *Nature Biotechnology* 14:845-851, (Jul. 1996).

Geysen, H.M. et al. "Use of Peptide Synthesis to Probe Viral Antigens for Epitopes to a Resolution of a Single Amino Acid," *Proc. Natl. Acad. Sci. USA* 81:3998-4002, (Jul. 1984).

Geysen, H.M. et al. "Small Peptides Induce Antibodies With a Sequence and Structural Requirement for Binding Antigen Comparable to Antibodies Raised Against the Native Protein," *Proc. Natl. Acad. Sci. USA* 82:178-182, (Jan. 1985).

Geysen, H.M. et al. "Strategies for Epitope Analysis Using Peptide Synthesis," *Journal of Immunological Methods* 102:259-274, (1987).

Ghetie, V. et al. "Increasing the Serum Persistence of an IgG Fragment by Random Mutagenesis," *Nature Biotechnology* 15:637-640, (Jul. 1997).

Ghetie, V. and Ward, E.S. "FcRn: The MHC Class I-Related Receptor That is More Than an IgG Transporter," *Immunology Today* 18(12):592-598, (Dec. 1997).

Guyer, R.L. et al. "Immunoglobulin Binding by Mouse Intestinal Epithelial Cell Receptors," *The Journal of Immunology* 117(2):587-593, (Aug. 1976).

Hamers-Casterman. C. et al. "Naturally Occurring Antibodies Devoid of Light Chains," *Nature* 363:446-448, (Jun. 3, 1993).

Harris, W.J. "Therapeutic Monoclonals: Production of Humanized Monoclonal Antibodies for In Vivo Imaging and Therapy," *Biochemical Society Transactions* 23:1035-1038, (1995).

Hawkins, R.E. et al. "Selection of Phage Antibodies by Binding Affinity: Mimicking Affinity Maturation," *J.Mol. Biol.* 266:889-896, (1992).

Hinton, P.R. et al. "Engineered Human IgG Antibodies with Longer Serum Half-Lives in Primates," *The Journal of Biological Chemistry* 279(8):6213-6216, (Feb. 20, 2004).

Holliger, P. et al. "'Diabodies': Small Bivalent and Bispecific Antibody Fragments," *Proc. Natl. Acad. Sci. USA* 90:6444-6448, (Jul. 1993).

Hongo, J.-A.S. et al. "Development and Characterization of Murine Monoclonal Antibodies to the Latency-Associated Peptide of Transforming Growth Factor $β_1$," *Hybridoma* 14(3):253-260, (1995).

Hoogenboom, H.R. and Winter, G. "By-Passing Immunisation: Human Antibodies from Synthetic Repertoires of Germline $V_H$ Gene Segments Rearranged in Vitro," *J. Mol. Biol.* 227:381-388, (1992).

Hu-Lieskovan, S. et al. "Improved Antitumor Activity of Immunotherapy With BRAF and MEK Inhibitors in BRAF$_{V600E}$ Melanoma," *Science Translational Medicine* 7(279):279ra41, (Mar. 18, 2015).

Hurle, M.R. and Gross, M. "Protein Engineering Techniques for Antibody Humanization," *Current Opinion in Biotechnology* 5:428-433, (1994).

International Preliminary Report on Patentablility dated Jan. 17, 2017, for PCT Application No. PCT/US2015/040582, filed on Jul. 15, 2015, 10 pages.

(56) References Cited

OTHER PUBLICATIONS

International Search Report dated Oct. 30, 2015, for PCT Application No. PCT/US2015/040582, filed on Jul. 15, 2015, 5 pages.
Jackson, J.R. et al. "In Vitro Antibody Maturation: Improvements of a High Affinity, Neutralizing Antibody Against IL-1β," *The Journal of Immunology* 154:3310-3319, (1995).
Jakobovits, A. et al. "Analysis of Homozygous Mutant Chimeric Mice: Deletion of the Immunoglobulin Heavy-Chain Joining Region Blocks B-Cell Development and Antibody Production," *Proc. Natl. Acad. Sci. USA* 90:2551-2555, (Mar. 1993).
Jakobovits, A. et al. "Germ-Line Transmission and Expression of a Human-Derived Yeast Artificial Chromosome," *Nature* 362:255-258, (Mar. 18, 1993).
Jenkins, M.K. and Schwartz, R.H. "Antigen Presentation by Chemically Modified Splenocytes Induces Antigen-Specific T Cell Unresponsiveness in Vitro and In Vivo," *Journal of Experimental Medicine* 165:302-319, (Feb. 1987).
Jiang, X. et al. "The Activation of MAPK in Melanoma Cells Resistant to BRAF Inhibition Promotes PD-L1 Expression That Is Reversible by MEK and PI3K Inhibition," *Clinical Cancer Research* 19(3):598-609, (Feb. 1, 2013).
Johnson, G. and Wu, T.T. "The Kabat Database and a Bioinformatics Example," *Methods in Molecular Biology* 248:11-25, (2003).
Jones, P.T. et al. "Replacing the Complementarity-Determining Regions in a Human Antibody With Those from a Mouse," *Nature* 321:522-525, (May 1986).
Kang, A.S. et al. "Linkage of Recognition and Replication Functions by Assembling Combinatorial Antibody Fab Libraries Along Phage Surfaces," *Proc. Natl. Acad. Sci. USA*, 88:4363-4366, (May 29, 1991).
Keir, M.E. et al. "PD-1 and Its Ligands in Tolerance and Immunity," *Annu. Rev. Immunol.* 26:677-704, (2008).
Kim J.-K. et al. "Localization of the Site of the Murine IgG1 Molecule That Is Involved in Binding to the Murine Intestinal Fc Receptor," *Eur. J. Immunol* 24:2429-2434, (1994).
Kohler, G. and Milstein, C. "Continuous Cultures of Fused Cells Secreting Antibody of Predefined Specificity," *Nature* 256:495-497, (Aug. 7, 1975).
Lafferty, K.J. and Cunningham, A.J. "A New Analysis of Allogeneic Interactions," *Aust. J. Exp. Biol. Med Sci.* 53(Pt. 1):27-42, (1975).
Lee, C.V. et al. "Bivalent Antibody Phage Display Mimics Natural Immunoglobulin," *Journal of Immunological Methods* 284:119-132, (2004).
Lee, C.V. et al. "High-Affinity Human Antibodies from Phage-Displayed Synthetic Fab Libraries with a Single Framework Scaffold," *J. Mol. Biol.* 340:1073-1093, (2004).
Lenschow, D.J. et al. "CD28/B7 System of T Cell Costimulation," *Annu. Rev. Immunol.* 14:233-258, (1996).
Lesche, R. et al. "Cre/loxP—Mediated Inactivation of the Murine Pten Tumor Suppressor Gene," *Genesis* 32:148-149, (2002).
Li, J. et al. "Human Antibodies for Immunotherapy Development Generated Via A Human B Cell Hybridoma Technology," *Proc. Natl. Acad. Sci. USA* 103(10):3557-3562, (Mar. 7, 2006).
Lonberg, N. et al. "Antigen-Specific Human Antibodies from Mice Comprising Four Distinct Genetic Modifications," *Nature* 368:856-859, (Apr. 28, 1994).
Lonberg, N. and Huszar, D. "Human Antibodies from Transgenic Mice," *Intern. Rev. Immunol.* 13:65-93, (1995).
Lowman, H.B. et al. "Selecting High-Affinity Binding Proteins by Monovalent Phage Display," *Biochemistry* 30(45):10822-10838, (1991).
Marks, J.D. et al. "By-passing Immunization: Human Antibodies from V-Gene Libraries Displayed on Phage," *J. Mol. Biol.* 222:581-597, (1991).
Marks, J.D. et al. "By-Passing Immunization: Building High Affinity Human Antibodies by Chain Shuffling," *Bio/Technology* 10:779-783, (Jul. 1992).
Martin-Liberal, J.and Larkin, J. "New RAF Kinase Inhibitors in Cancer Therapy," *Expert Opin. Pharmacother* 15(9):1235-1245, (2014).

Medivation Press Release (2016). "U.S. FDA Lifts Partial Clinical Hold on Medivation's Pidilizumab," Retrieved May 16, 2017 from http://www.marketwired.com/press-release/us-fda-lifts-partial-clinical-hold-on-medivations-pidilizumab-nasdaq-mdvn-2104281.htm, 2 pages.
Menzies, A.M. and Long, G.V. "Recent Advances in Melanoma Systemic Therapy. BRAF Inhibitors, CTLA4 Antibodies and Beyond," *European Journal of Cancer* 49:3229-3241, (2013).
Morrison, S.L. et al. "Chimeric Human Antibody Molecules: Mouse Antigen-Binding Domains With Human Constant Region Domains," *Proc. Natl. Acad. Sci. USA* 81:6851-6855, (Nov. 1984).
Morrison, S.L. "Success in Specification," *Nature* 368:812-813, (Apr. 28, 1994).
Neuberger, M. "Generating High-Avidity Human Mabs in Mice," *Nature Biotechnology* 14:826, (Jul. 1996).
Nicolaou, K.C. et al. "Calicheamicin $\theta^I_1$: A Rationally Designed Molecule with Extremely Potent and Selective DNA Cleaving Properties and Apoptosis Inducing Activity," *Angew. Chem. Int. Ed. Engl.* 33(2):183-186, (1994).
Okazaki, T. and Honjo, T. "PD-1 and PD-1 Ligands: From Discovery to Clinical Application," *International Immunology* 19(7):813-824, (2007).
Presta, L.G. "Antibody Engineering," *Current Opinion in Structural Biology* 2:593-596, (1992).
Ravetch, J.V. and Kinet, J.-P. "Fc Receptors," *Annu. Rev. Immunol.* 9:457-492, (1991).
Riechmann, L. et al. "Reshaping Human Antibodies for Therapy," *Nature* 332:323-329, (Mar. 24, 1988).
Schier, R. et al. "Identification of Functional and Structural Amino-Acid Residues by Parsimonious Mutagenesis," *Gene.* 16:147-155, (1996).
Schoofs, P.G. et al. "Epitopes of an Influenza Viral Peptide Recognized by Antibody At Single Amino Acid Resolution," *The Journal of Immunology* 140(2):611-616, (Jan. 15, 1988).
Sharpe, A.H. and Freeman, G.J. "The B7-CD28 Superfamily," *Nat. Rev.* 2:116-126, (Feb. 2002).
Sheriff, S. and Constantine, K.L. "Redefining the Minimal Antigen-Binding Fragment," *Nature Structural Biology* 3(9):733-736, (Sep. 1996).
Shields, R.L. et al. "High Resolution Mapping of the Binding Site on Human IgG1 for FcγRI, FcγRII, FcγRIII, and FcRn and Design of IgG1 Variants with Improved Binding to the FcγR*," *The Journal of Biological Chemistry* 276(9):6591-6604, (Mar. 2, 2001).
Sidhu, S.S. et al. "Phage-Displayed Antibody Libraries of Synthetic Heavy Chain Complementarity Determining Regions," *J. Mol. Biol.* 338:299-310, (2004).
Smith, G.P. "Surface Presentation of Protein Epitopes Using Bacteriophage Expression Systems," *Current Opinion in Biotechnology* 2:688-673, (1991).
Tentori, L. et al. "Challenging Resistance Mechanisms to Therapies for Metastatic Melanoma," *Trends Pharmacol. Sci.* 34(12):656-666, (Dec. 2013).
Thompson, R.H. et al. "Tumor B7-H1 Is Associated With Poor Prognosis in Renal Cell Carcinoma Patients With Long-Term Follow-Up," *Cancer Res.* 66(7):3381-3385, (Apr. 1, 2006).
Tsai, J. et al. "Discovery of a Selective Inhibitor of Oncogenic B-Raf Kinase With Potent Antimelanoma Activity," *Proc. Natl. Acad. Sci.* 105(8):3041-3046, (Feb. 26, 2008).
Van Dijk, M.A. and Van De Winkel, J.G.J. "Human Antibodies as Next Generation Therapeutics," *Current Opinion in Chemical Biology* 5:368-374, (2001).
Vaswani, S.K. and Hamilton, R.G. "Humanized Antibodies as Potential Therapeutic Drugs," *Ann. Allergy, Asthma & Immunol.* 81:105-115, (Aug. 1998).
Vella, L.J. et al. "The Kinase Inhibitors Dabrafenib and Trametinib Affect Isolated Immune Cell Populations," *Oncoimmunology* 3(7):e946367, 3 pages, (Aug. 1, 2014).
Written Opinion for PCT Application No. PCT/US2015/040582, filed on Jul. 15, 2015, 9 pages.
Xu, J.L. et al."Diversity in the CDR3 Region of $V_H$ is Sufficient for Most Antibody Specificities," *Immunity* 13:37-45, (Jul. 2000).
Yelton, D.E. et al. "Affinity Maturation of the BR96 Anti-Carcinoma Antibody by Codon-Based Mutagenesis," *The Journal of Immunology* 155:1994-2004, (1995).

(56) References Cited

OTHER PUBLICATIONS

Zambon, A. et al. "Small Molecule Inhibitors of BRAF in Clinical Trials," *Bioorg. & Med. Chem. Lett.* 22:789-792, (2012).

Zapata, G. et al. "Engineering Linear F(ab')$_2$ Fragments for Efficient Production in *Escherichia coli* and Enhanced Antiproliferative Activity," *Protein Engineering* 8(10):1057-1062, (1995).

Ghiotto, M. et al. (Aug. 2010, e-pub. Jun. 29, 2010). "PD-L1 and PD-L2 Differ in Their Molecular Mechanisms of Interaction With PD-1," *Int. Immunol.* 22(8):651-660, 19 pages.

Brahmer, J.R. et al. (Jul. 1, 2010). "Phase I Study of Single-Agent Anti-Programmed Death-I (MDX-1106) in Refractory Solid Tumors: Safety, Clinical Activity, Pharmacodynamics, and Immunologic Correlated," *J. Clin. Oncology* 28(18):3167-3175.

Namikawa, N. (Apr. 1, 2012). "Melanoma and Non-Melanoma Skin Cancers, I. Guidelines for Melanoma Diagnosis and Treatment: Summary and Points for Revision—Focusing on Novel Drug Therapies," *Jpn. J. Cancer Chemother.* 39(4):533-537. (Partial English Translation).

Wagenaar, T. R. et al. (2013, e-pub. Sep. 24, 2013). "Reistance to Vermurafenib Resulting From a Novel Mutation in the BRAFV600E Kinase Domain," *Pigment Cell Melanoma Res.* 27:124-133.

Benson, D.M. et al. "The PD-1/PD-L1 Axis Modulates the Natural Killer Cell Versus Multiple Myeloma Effect: a Therapeutic Target for CT-011, a Novel Monclonal Anti-PD-1 Antibody," *Blood* 116(13):2286-2293 (Sep. 2010, e-pub. May 11, 2010).

Berenbaum, M.C. et al. (1977). "Synergy, Additivism and Antagonism in Immunosuppression," *Clin. Exp. Immunol.* 28:1-18.

Berthon, C. et al. "In Acute Myeloid Leukemia, B7-H1 (PD-L1) Protection of Blasts From Cytotoxic T Cells is Induced by TLR Ligands and Interferon-Gamma and Can be Reversed Using MEK Inhibitors," *Cancer Immunology, Immunotherapy* 59(12):1839-1849 (2010, e-pub. Sep. 4, 2010).

Boni, A. et al. "Selective BRAF$_{V600E}$ Inhibition Enhances T-Cell Recognition of Melanoma Without Affecting Lymphocyte Function," *Cancer Res.* 70(13):5213-5219 (Jul. 1, 2010, e-pub. Jun. 15, 2010).

Eggermont, A.M.M. et al. "New Drugs in Melanoma: It's a Whole New World," *European Journal of Cancer* 47(14):2150-2157 (Jul. 2011, e-pub. Jul. 27, 2011).

Genentech, Inc. "Transforming the Future of Cancer Treatment. Oncology Research and Development," located at <www.roche.com/roche_oncology_r_d_.pdf,> 16 pages.

Guan et al., "BRAF Gene Mutations in Colorectal Cancer," *Journal of Clinical and Experimental Pathology* 26(3):356-359, (Jun. 2010). (English Translation of the Abstract Only.).

Hwu, W-J.. "Targeted Therapy for Metastatic Melanoma: From Bench to Bedside," *HemOncToday* (Jun. 25, 2010). Located at <http:www.healio.com/hematology-oncology/melanoma-skin-cancer/news/print/hematolo . . . >, last visited May 14, 2014, 4 pages.

International Search Report dated Nov. 6, 2012, for PCT Application No. PCT/US2012/049233, filed on Aug. 1, 2012, 7 pages.

Jin, H-T. et al. "Role of PD-1 in Regulating T-cell Immunity," *Current Topics in Microbiology and Immunology* 350:17-37 (2011).

Liu, J. et al. "Plasma Cells From Multiple Myeloma Patients Express B7-H1 (PD-L1) and Increase Expression After Stimulation with IFN-γ and TLR Ligands via a MyD88-TRAF6, and MEK-Dependent Pathway," *Blood* 110(1):296-304, (Jul. 2007).

Nomi, T. et al. "Clinical Significance and Therapeutic Potential of the Programmed Death-1 Ligand/Programmed Death-1 Pathway in Human Pancreatic Cancer," *Clinical Cancer Research, The American Association for Cancer Research* 13(7):2151-2157 (Apr. 1, 2007).

Okazaki, T. et al. "Granulocyte Colony-Stimulating Facor Promotes Tumor Angiogenesis Vai Increasing Circulating Endothelial Progenitor Cells and Gr1+GD11b+ Cells in Cancer Antimal Models," *Intern. Immun.* 18(1):813 (2007, e-pub. Dec. 13, 2005).

Wiesenthal Cancer Group. (Mar. 14, 2012). "Synergy Analysis of "Classic" and Newer Drug Combinations," located at *Human Tumor Assay Journal*, on-line at http://weisenthal.org/synergy1.htm, 1 page.

Written Opinion dated Nov. 6, 2012, for PCT Application No. PCT/US2012/049233, filed on Aug. 1, 2012, 9 pages.

Yamakawa, M. et al. "The Dipole Moments of Some Heptafulvene Derivatives," *J. Am. Chem. Soc.* 82:5665-5667 (Nov. 5, 1960).

U.S. Appl. No. 14/825,779, filed Aug. 13, 2015, entitled "Methods of Using Anti-PD-L1 Antibodies and Their Use to Enhance T-Cell Function to Treat Tumor Immunity," by inventor "Irving et al." (Copy not submitted herewith pursuant to the waiver of 37 C.F.R. 1.98(a)(2)(iii) issued by the Office dated Sep. 21, 2004).

\* cited by examiner

SEQUENCE LISTING

```
<160> NUMBER OF SEQ ID NOS: 28

<210> SEQ ID NO 1
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = D or G

<400> SEQUENCE: 1

Gly Phe Thr Phe Ser Xaa Ser Trp Ile His
1               5                   10

<210> SEQ ID NO 2
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = S or L
<220> FEATURE:
<221> NAME/KEY: VARIANT
<222> LOCATION: 10
<223> OTHER INFORMATION: Xaa = T or S

<400> SEQUENCE: 2

Ala Trp Ile Xaa Pro Tyr Gly Gly Ser Xaa Tyr Tyr Ala Asp Ser Val
1               5                   10                  15

Lys Gly

<210> SEQ ID NO 3
<211> LENGTH: 9
<212> TYPE: PRT
<213> ORGANISM: Artificial Sequence
<220> FEATURE:
<223> OTHER INFORMATION: Synthetic Construct

<400> SEQUENCE: 3

Arg His Trp Pro Gly Gly Phe Asp Tyr
1               5
```

<210> SEQ ID NO 4
<211> LENGTH: 25
<212> TYPE: PRT
<213> ORGANISM: Artificial Sequence
<220> FEATURE:
<223> OTHER INFORMATION: Synthetic Construct

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 5
<211> LENGTH: 13
<212> TYPE: PRT
<213> ORGANISM: Artificial Sequence
<220> FEATURE:
<223> OTHER INFORMATION: Synthetic Construct

<400> SEQUENCE: 5

Trp Val Arg Gln Ala Pro Gly Lys Gly Leu Glu Trp Val
1               5                   10

<210> SEQ ID NO 6
<211> LENGTH: 32
<212> TYPE: PRT
<213> ORGANISM: Artificial Sequence
<220> FEATURE:
<223> OTHER INFORMATION: Synthetic Construct

<400> SEQUENCE: 6

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 7
<211> LENGTH: 11
<212> TYPE: PRT
<213> ORGANISM: Artificial Sequence
<220> FEATURE:
<223> OTHER INFORMATION: Synthetic Construct

<400> SEQUENCE: 7

Trp Gly Gln Gly Thr Leu Val Thr Val Ser Ala
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = D or V
<220> FEATURE:
<221> NAME/KEY: VARIANT
<222> LOCATION: 6
<223> OTHER INFORMATION: Xaa = V or I
<220> FEATURE:
<221> NAME/KEY: VARIANT
<222> LOCATION: 7
<223> OTHER INFORMATION: Xaa = S or N
<220> FEATURE:
<221> NAME/KEY: VARIANT

```
<222> LOCATION: 9
<223> OTHER INFORMATION: Xaa = A or F
<220> FEATURE:
<221> NAME/KEY: VARIANT
<222> LOCATION: 10
<223> OTHER INFORMATION: Xaa = V or L

<400> SEQUENCE: 8

Arg Ala Ser Gln Xaa Xaa Xaa Thr Xaa Xaa Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = F or T
<220> FEATURE:
<221> NAME/KEY: VARIANT
<222> LOCATION: 6
<223> OTHER INFORMATION: Xaa = Y or A

<400> SEQUENCE: 9

Ser Ala Ser Xaa Leu Xaa Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Y, G, F, or S
<220> FEATURE:
<221> NAME/KEY: VARIANT
<222> LOCATION: 4
<223> OTHER INFORMATION: Xaa = L, Y, F or W
<220> FEATURE:
<221> NAME/KEY: VARIANT
<222> LOCATION: 5
<223> OTHER INFORMATION: Xaa = Y, N, A, T, G, F or I
<220> FEATURE:
<221> NAME/KEY: VARIANT
<222> LOCATION: 6
<223> OTHER INFORMATION: Xaa = H, V, P, T or I
<220> FEATURE:
<221> NAME/KEY: VARIANT
<222> LOCATION: 8
<223> OTHER INFORMATION: Xaa = A, W, R, P or T

<400> SEQUENCE: 10

Gln Gln Xaa Xaa Xaa Xaa Pro Xaa Thr
1               5

<210> SEQ ID NO 11
<211> LENGTH: 23
<212> TYPE: PRT
<213> ORGANISM: Artificial Sequence
<220> FEATURE:
<223> OTHER INFORMATION: Synthetic Construct

<400> SEQUENCE: 11

Asp Ile Gln Met Thr Gln Ser Pro Ser Ser Leu Ser Ala Ser Val Gly
1               5                   10                  15
```

Asp Arg Val Thr Ile Thr Cys
            20

<210> SEQ ID NO 12
<211> LENGTH: 15
<212> TYPE: PRT
<213> ORGANISM: Artificial Sequence
<220> FEATURE:
<223> OTHER INFORMATION: Synthetic Construct

<400> SEQUENCE: 12

Trp Tyr Gln Gln Lys Pro Gly Lys Ala Pro Lys Leu Leu Ile Tyr
1               5                   10                  15

<210> SEQ ID NO 13
<211> LENGTH: 32
<212> TYPE: PRT
<213> ORGANISM: Artificial Sequence
<220> FEATURE:
<223> OTHER INFORMATION: Synthetic Construct

<400> SEQUENCE: 13

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 14
<211> LENGTH: 11
<212> TYPE: PRT
<213> ORGANISM: Artificial Sequence
<220> FEATURE:
<223> OTHER INFORMATION: Synthetic Construct

<400> SEQUENCE: 14

Phe Gly Gln Gly Thr Lys Val Glu Ile Lys Arg
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic Construct

<400> SEQUENCE: 15

Gly Phe Thr Phe Ser Asp Ser Trp Ile His
1               5                   10

<210> SEQ ID NO 16
<211> LENGTH: 18
<212> TYPE: PRT
<213> ORGANISM: Artificial Sequence
<220> FEATURE:
<223> OTHER INFORMATION: Synthetic Construct

<400> SEQUENCE: 16

Ala Trp Ile Ser Pro Tyr Gly Gly Ser Thr Tyr Tyr Ala Asp Ser Val
1               5                   10                  15

Lys Gly

<210> SEQ ID NO 17
<211> LENGTH: 11
<212> TYPE: PRT
<213> ORGANISM: Artificial Sequence
<220> FEATURE:

<223> OTHER INFORMATION: Synthetic Construct

<400> SEQUENCE: 17

Arg Ala Ser Gln Asp Val Ser Thr Ala Val Ala
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Synthetic Construct

<400> SEQUENCE: 18

Ser Ala Ser Phe Leu Tyr Ser
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic Construct

<400> SEQUENCE: 19

Gln Gln Tyr Leu Tyr His Pro Ala Thr
1               5

<210> SEQ ID NO 20
<211> LENGTH: 118
<212> TYPE: PRT
<213> ORGANISM: Artificial Sequence
<220> FEATURE:
<223> OTHER INFORMATION: Synthetic Construct

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala
        115

<210> SEQ ID NO 21
<211> LENGTH: 108
<212> TYPE: PRT
<213> ORGANISM: Artificial Sequence
<220> FEATURE:
<223> OTHER INFORMATION: Synthetic Construct

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
            100                 105

<210> SEQ ID NO 22
<211> LENGTH: 440
<212> TYPE: PRT
<213> ORGANISM: Artificial Sequence
<220> FEATURE:
<223> OTHER INFORMATION: Synthetic Construct

<400> SEQUENCE: 22

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

```
Asp Gly Val Glu Val His Asn Ala Lys Thr Lys Pro Arg Glu Glu Gln
            275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
        370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 23
<211> LENGTH: 214
<212> TYPE: PRT
<213> ORGANISM: Homo sapiens

<400> SEQUENCE: 23

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

Phe Asn Arg Gly Glu Cys
    210

<210> SEQ ID NO 24
<211> LENGTH: 118
<212> TYPE: PRT
<213> ORGANISM: Artificial Sequence
<220> FEATURE:
<223> OTHER INFORMATION: Synthetic Construct

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 25
<211> LENGTH: 11
<212> TYPE: PRT
<213> ORGANISM: Artificial Sequence
<220> FEATURE:
<223> OTHER INFORMATION: Synthetic Construct

<400> SEQUENCE: 25

Trp Gly Gln Gly Thr Leu Val Thr Val Ser Ser
1               5                   10

<210> SEQ ID NO 26
<211> LENGTH: 448
<212> TYPE: PRT
<213> ORGANISM: Artificial Sequence
<220> FEATURE:
<223> OTHER INFORMATION: Synthetic Construct

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
                100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 27
<211> LENGTH: 214
<212> TYPE: PRT
<213> ORGANISM: Artificial Sequence
<220> FEATURE:
<223> OTHER INFORMATION: Synthetic Construct

<400> SEQUENCE: 27

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 28
<211> LENGTH: 122
<212> TYPE: PRT
<213> ORGANISM: Artificial Sequence
<220> FEATURE:
<223> OTHER INFORMATION: Synthetic Construct

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys
        115                 120
```

METHODS OF TREATING CANCER USING PD-1 AXIS BINDING ANTAGONISTS AND MEK INHIBITORS

CROSS REFERENCE TO RELATED APPLICATIONS

This application is a continuation of International Application No. PCT/US2015/040582, filed internationally on Jul. 15, 2015, which claims the priority benefit of U.S. provisional application Ser. No. 62/024,988, filed Jul. 15, 2014; each of which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392027500SEQLIST.txt, date recorded: Dec. 19, 2016, size: 21 KB).

BACKGROUND

The provision of two distinct signals to T-cells is a widely accepted model for lymphocyte activation of resting T lymphocytes by antigen-presenting cells (APCs). Lafferty et al, Aust. J. Exp. Biol. Med. ScL 53: 27-42 (1975). This model further provides for the discrimination of self from non-self and immune tolerance. Bretscher et al, Science 169: 1042-1049 (1970); Bretscher, P. A., P.N.A.S. USA 96: 185-190 (1999); Jenkins et al, J. Exp. Med. 165: 302-319 (1987). The primary signal, or antigen specific signal, is transduced through the T-cell receptor (TCR) following recognition of foreign antigen peptide presented in the context of the major histocompatibility-complex (MHC). The second or co-stimulatory signal is delivered to T-cells by co-stimulatory molecules expressed on antigen-presenting cells (APCs), and induces T-cells to promote clonal expansion, cytokine secretion and effector function. Lenschow et al., Ann. Rev. Immunol. 14:233 (1996). In the absence of co-stimulation, T-cells can become refractory to antigen stimulation, do not mount an effective immune response, and further may result in exhaustion or tolerance to foreign antigens.

In the two-signal model T-cells receive both positive and negative secondary co-stimulatory signals. The regulation of such positive and negative signals is critical to maximize the host's protective immune responses, while maintaining immune tolerance and preventing autoimmunity. Negative secondary signals seem necessary for induction of T-cell tolerance, while positive signals promote T-cell activation. While the simple two-signal model still provides a valid explanation for naive lymphocytes, a host's immune response is a dynamic process, and co-stimulatory signals can also be provided to antigen-exposed T-cells. The mechanism of co-stimulation is of therapeutic interest because the manipulation of co-stimulatory signals has shown to provide a means to either enhance or terminate cell-based immune response. Recently, it has been discovered that T cell dysfunction or anergy occurs concurrently with an induced and sustained expression of the inhibitory receptor, programmed death 1 polypeptide (PD-1). As a result, therapeutic targeting of PD-1 and other molecules which signal through interactions with PD-1, such as programmed death ligand 1 (PD-L1) and programmed death ligand 2 (PD-L2) are an area of intense interest.

PD-L1 is overexpressed in many cancers and is often associated with poor prognosis (Okazaki T et al., Intern. Immun. 2007 19(7):813) (Thompson R H et al., Cancer Res 2006, 66(7):3381). Interestingly, the majority of tumor infiltrating T lymphocytes predominantly express PD-1, in contrast to T lymphocytes in normal tissues and peripheral blood T lymphocytes indicating that up-regulation of PD-1 on tumor-reactive T cells can contribute to impaired antitumor immune responses (Blood 2009 114(8):1537). This may be due to exploitation of PD-L1 signaling mediated by PD-L1 expressing tumor cells interacting with PD-1 expressing T cells to result in attenuation of T cell activation and evasion of immune surveillance (Sharpe et al., Nat Rev 2002) (Keir M E et al., 2008 Annu. Rev. Immunol. 26:677). Therefore, inhibition of the PD-L1/PD-1 interaction may enhance CD8+ T cell-mediated killing of tumors.

The inhibition of PD-1 axis signaling through its direct ligands (e.g., PD-L1, PD-L2) has been proposed as a means to enhance T cell immunity for the treatment of cancer (e.g., tumor immunity). Moreover, similar enhancements to T cell immunity have been observed by inhibiting the binding of PD-L1 to the binding partner B7-1. Furthermore, combining inhibition of PD-1 signaling with other signaling pathways (e.g. MAPK pathway, "MEK") that are deregulated in tumor cells may further enhance treatment efficacy. However, an optimal therapeutic treatment would combine blockade of PD-1 receptor/ligand interaction with an agent that directly inhibited tumor growth, optionally further including unique immune enhancing properties not provided by PD-1 blockade alone. There remains a need for such an optimal therapy for treating, stabilizing, preventing, and/or delaying development of various cancers.

All references, publications, and patent applications disclosed herein are hereby incorporated by reference in their entirety.

BRIEF SUMMARY

Provided herein are methods for treating or delaying progression of cancer in an individual comprising administering to the individual an effective amount of a PD-1 axis binding antagonist and a MEK inhibitor, wherein the individual has cancer or is at risk of developing cancer that is resistant to a B-raf antagonist. In some embodiments, the method further comprises diagnosing the individual as having a cancer that is resistant to a B-raf antagonist, wherein the diagnosing occurs prior to administering the effective amount of the PD-1 axis binding antagonist and the MEK inhibitor. In some embodiments, the method further comprises selecting an individual for treatment based on the individual having cancer that is resistant to a B-raf antagonist or assessing that the individual is at risk of developing cancer that is resistant to a B-raf antagonist, wherein the selecting occurs prior to administering the effective amount of the PD-1 axis binding antagonist and the MEK inhibitor. In some embodiments, the individual has not been previously treated with a B-raf antagonist. In some embodiments, the individual has been previously treated with a B-raf antagonist.

In another aspect, provided herein are methods for treating or delaying progression of cancer in an individual comprising (a) diagnoising the individual as having a cancer that is resistant to a B-raf antagonist; and (b) administering to the individual an effective amount of a PD-1 axis binding antagonist and a MEK inhibitor, wherein the administering occurs after diagnosing the individual. In some embodiments, the individual has not been previously treated with a B-raf antagonist. In some embodiments, the individual has been previously treated with a B-raf antagonist.

In another aspect, provided herein are methods for treating or delaying progression of cancer in an individual comprising (a) selecting an individual for treatment based on the individual having cancer that is resistant to a B-raf antagonist or assessing that the individual is at risk of developing cancer that is resistant to a B-raf antagonist; and (b) administering to the individual an effective amount of a PD-1 axis binding antagonist and a MEK inhibitor, wherein the administering occurs after selecting the individual. In some embodiments, the individual has not been previously treated with a B-raf antagonist. In some embodiments, the individual has been previously treated with a B-raf antagonist.

In another aspect, provided herein are methods for treating or delaying progression of cancer in an individual comprising administering to the individual an effective amount of a PD-1 axis binding antagonist and a MEK inhibitor, wherein the individual has been previously treated with a B-raf antagonist for cancer.

In some embodiments, the cancer in the individual has progressed within 1 month, 6 months, 1 year, or 5 years after completing a B-raf antagonist-based therapy regimen. In some embodiments, the B-raf antagonist is a small molecule inhibitor, an antibody, a peptide, a peptidomimetic, an aptamer or a polynucleotide. In some embodiments, the B-raf antagonist is dabrafenib, vemurafenib, GSK 2118436, RAF265, XL281, ARQ736, BAY73-4506, sorafenib, PLX4720, PLX-3603, GSK2118436, GDC-0879, or N-(3-(5-(4-chlorophenyl)-1H-pyrrolo[2,3-b]pyridine-3-carbonyl)-2,4-difluorophenyl)propane-1-sulfonamide. In some embodiments, the B-raf antagonist is a selective B-raf antagonist of B-raf V600. In some embodiments, the selective B-raf antagonist of B-raf V600 is a selective antagonist of B-raf V600E. In some embodiments, the selective B-raf antagonist of B-raf V600 is a selective antagonist of B-raf V600E, B-raf V600K, and/or V600D. In some embodiments, the selective B-raf antagonist of B-raf V600 is a selective antagonist of B-raf V600R.

In some embodiments, the cancer contains a BRAF V600E mutation, a BRAF wildtype, a KRAS wildtype, or an activating KRAS mutation. In some embodiments, the treatment results in a sustained response in the individual after cessation of the treatment. In some embodiments, the individual has colorectal cancer, melanoma, lung cancer, ovarian cancer, breast cancer, pancreatic cancer, hematological malignancy, bladder cancer, and/or renal cell carcinoma. In some embodiments, the cancer is metastatic.

In some embodiments, the PD-1 axis binding antagonist is selected from the group consisting of a PD-1 binding antagonist, a PD-L1 binding antagonist and a PD-L2 binding antagonist. In some embodiments, the PD-1 axis binding antagonist is a PD-1 binding antagonist. In some embodiments, the PD-1 binding antagonist inhibits the binding of PD-1 to its ligand binding partners. In some embodiments, the PD-1 binding antagonist inhibits the binding of PD-1 to PD-L1, PD-1 to PD-L2, or PD-1 to both PD-L1 and PD-L2. In some embodiments, the PD-1 binding antagonist is an antibody. In some embodiments, the PD-1 binding antagonist is MDX-1106, Merck 3745, CT-011, MEDI-0680, PDR001, REGN2810, BGB-108, BGB-A317, or AMP-224. In some embodiments, the PD-1 binding antagonist is nivolumab, pembrolizumab, pidilizumab, MEDI-0680, PDR001, REGN2810, BGB-108, BGB-A317, or AMP-224. In some embodiments, the PD-1 axis binding antagonist is a PD-L1 binding antagonist. In some embodiments, the PD-L1 binding antagonist inhibits the binding of PD-L1 to PD-1, PD-L1 to B7-1, or PD-L1 to both PD-1 and B7-1. In some embodiments, the PD-L1 binding antagonist is an anti-PD-L1 antibody. In some embodiments, the anti-PD-L1 antibody is a monoclonal antibody. In some embodiments, the anti-PD-L1 antibody is an antibody fragment selected from the group consisting of Fab, Fab'-SH, Fv, scFv, and (Fab')$_2$ fragments. In some embodiments, the anti-PD-L1 antibody is a humanized antibody or a human antibody. In some embodiments, the PD-L1 binding antagonist is selected from the group consisting of: YW243.55.S70, MPDL3280A, MEDI4736, MDX-1105, and MSB0010718C. In some embodiments, the PD-L1 binding antagonist is selected from the group consisting of: YW243.55.S70, atezolizumab, durvalumab, MDX-1105, and avelumab. In some embodiments, the antibody comprises a heavy chain comprising HVR-H1 sequence of SEQ ID NO: 15, HVR-H2 sequence of SEQ ID NO:16, and HVR-H3 sequence of SEQ ID NO:3; and a light chain comprising HVR-L1 sequence of SEQ ID NO:17, HVR-L2 sequence of SEQ ID NO:18, and HVR-L3 sequence of SEQ ID NO: 19. In some embodiments, the antibody comprises a heavy chain variable region comprising the amino acid sequence of SEQ ID NO:24 or 28 and a light chain variable region comprising the amino acid sequence of SEQ ID NO:21. In some embodiments, the PD-1 axis binding antagonist is a PD-L2 binding antagonist. In some embodiments, the PD-L2 binding antagonist is an antibody. In some embodiments, the PD-L2 binding antagonist is an immunoadhesin. In some embodiments, the MEK inhibitor is a competitive inhibitor of MEK. In some embodiments, the MEK inhibitor is more selective against an activating KRAS mutation. In some embodiments, the MEK inhibitor is an allosteric inhibitor of MEK. In some embodiments, the MEK inhibitor is more selective against an activating BRAF mutation. In some embodiments, the MEK inhibitor is a compound of the formula (I), (II), (III), (IV), (V), (VI) or (VII), or a pharmaceutically acceptable salt or solvate thereof. In some embodiments, the MEK inhibitor is selected from the group consisting of G02442104, G-38963, G02443714, G00039805 and GDC-0973, or a pharmaceutically acceptable salt or solvate thereof. In some embodiments, the MEK inhibitor is G02443714, G02442104 or G00039805.

In some embodiments, the MEK inhibitor is administered continuously. In some embodiments, the MEK inhibitor is administered intermittently. In some embodiments, the MEK inhibitor is administered before the PD-1 axis binding antagonist. In some embodiments, the MEK inhibitor is administered simultaneous with the PD-1 axis binding antagonist. In some embodiments, the MEK inhibitor is administered after the PD-1 axis binding antagonist. In some embodiments, the PD-1 axis binding antagonist and/or the MEK inhibitor is administered intravenously, intramuscularly, subcutaneously, topically, orally, transdermally, intraperitoneally, intraorbitally, by implantation, by inhalation, intrathecally, intraventricularly, or intranasally.

In another aspect, provided herein are kits comprising a PD-1 axis binding antagonist and a package insert comprising instructions for using the PD-1 axis binding antagonist in combination with a MEK inhibitor to treat or delay progression of cancer in an individual, wherein the individual has cancer or is at risk of developing cancer that is resistant to a B-raf antagonist. In another aspect, provided herein are kits comprising a PD-1 axis binding antagonist and a MEK inhibitor, and a package insert comprising instructions for using the PD-1 axis binding antagonist and the MEK inhibitor to treat or delay progression of cancer in an individual, wherein the individual has cancer or is at risk of developing cancer that is resistant to a B-raf antagonist. In another aspect, provided herein are kits comprising a MEK inhibitor and a package insert comprising instructions for using the MEK inhibitor in combination with a PD-1 axis binding antagonist to treat or delay progression of cancer in an individual, wherein the individual has cancer or is at risk of developing cancer that is resistant to a B-raf antagonist. In another aspect, provided herein are kits comprising a PD-1 axis binding antagonist and a package insert comprising instructions for using the PD-1 axis binding antagonist in combination with a MEK inhibitor to treat or delay progression of cancer in an individual, wherein the individual has been previously treated with a B-raf antagonist for cancer. In another aspect, provided herein are kits comprising a PD-1 axis binding antagonist and a MEK inhibitor, and a package insert comprising instructions for using the PD-1 axis binding antagonist and the MEK inhibitor to treat or delay progression of cancer in an individual, wherein the individual has been previously treated with a B-raf antagonist for cancer. In another aspect, provided herein are kits comprising a MEK inhibitor and a package insert comprising instructions for using the MEK inhibitor in combination with a PD-1 axis binding antagonist to treat or delay progression of cancer in an individual, wherein the individual has been previously treated with a B-raf antagonist for cancer.

In some embodiments, the individual is a human.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

DETAILED DESCRIPTION

I. General Techniques

Figure 1:
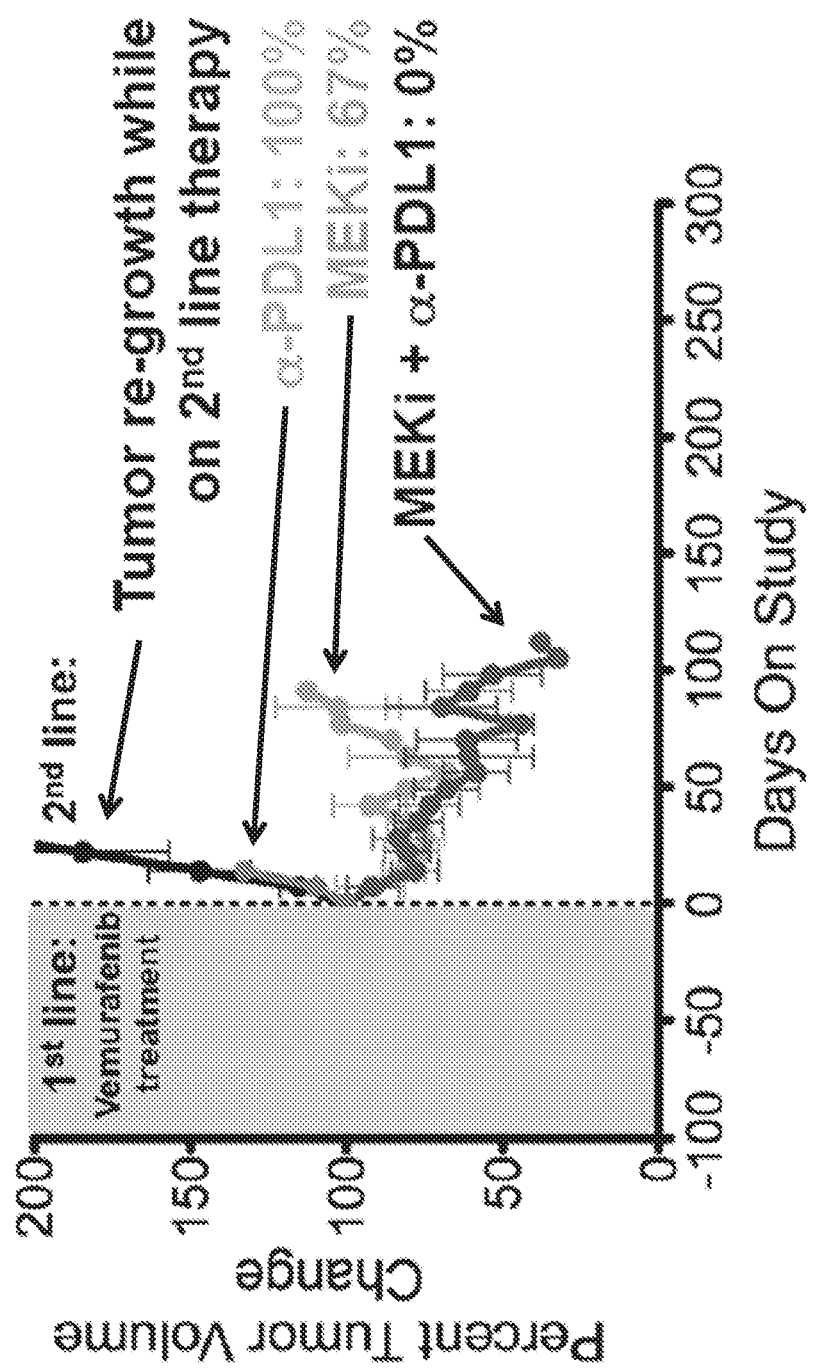
FIG. 1 shows tumor re-growth upon treatment with anti-PDL1, a MEK inhibitor, or both. The graph shows the percent tumor volume change over time during treatment with the indicated agent(s).

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual,* and *Animal Cell Culture* (R. I. Freshney, ed. (1987)); *Oligonucleotide Synthesis* (M. J. Gait, ed., 1984); *Methods in Molecular Biology,* Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction,* (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

II. Definitions

The term "antagonist" is used in the broadest sense, and includes any molecule that partially or fully blocks, inhibits, or neutralizes a biological activity of a native polypeptide disclosed herein. In a similar manner, the term "agonist" is used in the broadest sense and includes any molecule that mimics a biological activity of a native polypeptide disclosed herein. Suitable agonist or antagonist molecules specifically include agonist or antagonist antibodies or antibody fragments, fragments or amino acid sequence variants of native polypeptides, peptides, antisense oligonucleotides, small organic molecules, etc. Methods for identifying agonists or antagonists of a polypeptide may comprise contacting a polypeptide with a candidate agonist or antagonist molecule and measuring a detectable change in one or more biological activities normally associated with the polypeptide.

The term "aptamer" refers to a nucleic acid molecule that is capable of binding to a target molecule, such as a polypeptide. For example, an aptamer of the invention can specifically bind to a B-raf polypeptide, or to a molecule in a signaling pathway that modulates the expression or activity of B-raf. The generation and therapeutic use of aptamers are well established in the art. See, e.g., U.S. Pat. No. 5,475,096, and the therapeutic efficacy of Macugen® (Eyetech, New York) for treating age-related macular degeneration.

The term "PD-1 axis binding antagonist" is a molecule that inhibits the interaction of a PD-1 axis binding partner with either one or more of its binding partner, so as to remove T-cell dysfunction resulting from signaling on the PD-1 signaling axis—with a result being to restore or enhance T-cell function (e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonists" is a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific aspect, a PD-1 binding antagonist is MDX-1106 described herein. In another specific aspect, a PD-1 binding antagonist is Merck 3745 described herein. In another specific aspect, a PD-1 binding antagonist is CT-011 described herein.

The term "PD-L1 binding antagonists" is a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific aspect, an anti-PD-L1 antibody is YW243.55.S70 described herein. In another specific aspect, an anti-PD-L1 antibody is MDX-1105 described herein. In still another specific aspect, an anti-PD-L1 antibody is MPDL3280A (atezolizumab) described herein.

The term "PD-L2 binding antagonists" is a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

The term "dysfunction" in the context of immune dysfunction, refers to a state of reduced immune responsiveness to antigenic stimulation. The term includes the common elements of both exhaustion and/or anergy in which antigen recognition may occur, but the ensuing immune response is ineffective to control infection or tumor growth.

The term "dysfunctional", as used herein, also includes refractory or unresponsive to antigen recognition, specifically, impaired capacity to translate antigen recognition into down-stream T-cell effector functions, such as proliferation, cytokine production (e.g., IL-2) and/or target cell killing.

The term "anergy" refers to the state of unresponsiveness to antigen stimulation resulting from incomplete or insufficient signals delivered through the T-cell receptor (e.g. increase in intracellular $Ca^{+2}$ in the absence of ras-activation). T cell anergy can also result upon stimulation with antigen in the absence of co-stimulation, resulting in the cell becoming refractory to subsequent activation by the antigen even in the context of costimulation. The unresponsive state can often be overriden by the presence of Interleukin-2. Anergic T-cells do not undergo clonal expansion and/or acquire effector functions.

The term "exhaustion" refers to T cell exhaustion as a state of T cell dysfunction that arises from sustained TCR signaling that occurs during many chronic infections and cancer. It is distinguished from anergy in that it arises not through incomplete or deficient signaling, but from sustained signaling. It is defined by poor effector function, sustained expression of inhibitory receptors and a transcriptional state distinct from that of functional effector or memory T cells. Exhaustion prevents optimal control of infection and tumors. Exhaustion can result from both extrinsic negative regulatory pathways (e.g., immunoregulatory cytokines) as well as cell intrinsic negative regulatory (costimulatory) pathways (PD-1, B7-H3, B7-H4, etc.).

"Enhancing T-cell function" means to induce, cause or stimulate a T-cell to have a sustained or amplified biological function, or renew or reactivate exhausted or inactive T-cells. Examples of enhancing T-cell function include: increased secretion of γ-interferon from $CD8^+$ T-cells, increased proliferation, increased antigen responsiveness (e.g., viral, pathogen, or tumor clearance) relative to such levels before the intervention. In one embodiment, the level of enhancement is as least 50%, alternatively 60%, 70%, 80%, 90%, 100%, 120%, 150%, or 200%. The manner of measuring this enhancement is known to one of ordinary skill in the art.

A "T cell dysfunctional disorder" is a disorder or condition of T-cells characterized by decreased responsiveness to antigenic stimulation. In a particular embodiment, a T-cell dysfunctional disorder is a disorder that is specifically associated with inappropriate increased signaling through PD-1. In another embodiment, a T-cell dysfunctional disorder is one in which T-cells are anergic or have decreased ability to secrete cytokines, proliferate, or execute cytolytic activity. In a specific aspect, the decreased responsiveness results in ineffective control of a pathogen or tumor expressing an immunogen. Examples of T cell dysfunctional disorders characterized by T-cell dysfunction include unresolved acute infection, chronic infection and tumor immunity.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

"Immunogenicity" refers to the ability of a particular substance to provoke an immune response. Tumors are immunogenic and enhancing tumor immunogenicity aids in the clearance of the tumor cells by the immune response. Examples of enhancing tumor immunogenicity include treatment with anti-PDL antibodies and a MEK inhibitor.

"Sustained response" refers to the sustained effect on reducing tumor growth after cessation of a treatment. For example, the tumor size may remain to be the same or smaller as compared to the size at the beginning of the administration phase. In some embodiments, the sustained response has a duration at least the same as the treatment duration, at least 1.5×, 2.0×, 2.5×, or 3.0× length of the treatment duration.

As used herein, "cancer" and "cancerous" refer to or describe the physiological condition in mammals that is typically characterized by unregulated cell growth. Included in this definition are benign and malignant cancers as well as dormant tumors or micrometastases. Examples of cancer include but are not limited to, carcinoma, lymphoma, blastoma, sarcoma, and leukemia. More particular examples of such cancers include but are not limited to squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. Examples of cancer may include primary tumors of any of the above types of cancer or metastatic tumors at a second site derived from any of the above types of cancer.

The term "antibody" includes monoclonal antibodies (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, F(ab')$_2$, and Fv). The term "immunoglobulin" (Ig) is used interchangeably with "antibody" herein.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology*, 8th Edition, Daniel P. Sties, Abba I. Terr and Tristram G. Parsolw (eds), Appleton & Lange, Norwalk, Conn., 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the CH sequence and function, e.g., humans express the following subclasses: IgG1, IgG2A, IgG2B, IgG3, IgG4, IgA1 and IgA2.

The "variable region" or "variable domain" of an antibody refers to the amino-terminal domains of the heavy or light chain of the antibody. The variable domains of the heavy chain and light chain may be referred to as "VH" and "VL", respectively. These domains are generally the most variable parts of the antibody (relative to other antibodies of the same class) and contain the antigen binding sites.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al., *Sequences of Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent cellular toxicity.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. *Monoclonal* antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein., *Nature,* 256:495-97 (1975); Hongo et al., *Hybridoma,* 14 (3): 253-260 (1995), Harlow et al., *Antibodies: A Laboratory Manual,* (Cold Spring Harbor Laboratory Press, 2$^{nd}$ ed. 1988); Hammerling et al., in: *Monoclonal Antibodies* and T-Cell Hybridomas 563-681 (Elsevier, N.Y., 1981)), recombinant DNA methods (see, e.g., U.S. Pat. No. 4,816,567), phage-display technologies (see, e.g., Clackson et al., *Nature,* 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and U.S. Pat. No. 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The term "naked antibody" refers to an antibody that is not conjugated to a cytotoxic moiety or radiolabel.

The terms "full-length antibody," "intact antibody" or "whole antibody" are used interchangeably to refer to an antibody in its substantially intact form, as opposed to an antibody fragment. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8(10): 1057-1062 [1995]); single-chain antibody molecules and multispecific antibodies formed from antibody fragments. Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in *The Pharmacology of Monoclonal Antibodies,* vol. 113, Rosenburg and Moore eds., Springer-Verlag, New York, pp. 269-315 (1994).

"Functional fragments" of the antibodies of the invention comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Natl. Acad. Sci. USA* 90: 6444-6448 (1993).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)). Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from an HVR (hereinafter defined) of the recipient are replaced by residues from an HVR of a non-human species (donor antibody) such as mouse, rat, rabbit or non-human primate having the desired specificity, affinity, and/or capacity. In some instances, framework ("FR") residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR are typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, for example, Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227: 381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA*, 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk, *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact | |
|---|---|---|---|---|---|
| L1 | L24-L34 | L24-L34 | L26-L32 | L30-L36 | |
| L2 | L50-L56 | L50-L56 | L50-L52 | L46-L55 | |
| L3 | L89-L97 | L89-L97 | L91-L96 | L89-L96 | |
| H1 | H31-H35B | H26-H35B | H26-H32 | H30-H35B | (Kabat numbering) |
| H1 | H31-H35 | H26-H35 | H26-H32 | H30-H35 | (Chothia numbering) |
| H2 | H50-H65 | H50-H58 | H53-H55 | H47-H58 | |
| H3 | H95-H102 | H95-H102 | H96-H101 | H93-H101 | |

HVRs may comprise "extended HVRs" as follows: 24-36 or 24-34 (L), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

"Framework" or "FR" residues are those variable-domain residues other than the HVR residues as herein defined.

A "human consensus framework" or "acceptor human framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, 5$^{th}$ Ed. Public Health Service, National Institutes of Health, Bethesda, Md. (1991). Examples include for the VL, the subgroup may be subgroup kappa I, kappa II, kappa III or kappa IV as in Kabat et al., supra. Additionally, for the VH, the subgroup may be subgroup I, subgroup II, or subgroup III as in Kabat et al., supra. Alternatively, a human consensus framework can be derived from the above in which particular residues, such as when a human framework residue is selected based on its homology to the donor framework by aligning the donor framework sequence with a collection of various human framework sequences. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less.

A "VH subgroup III consensus framework" comprises the consensus sequence obtained from the amino acid sequences in variable heavy subgroup III of Kabat et al., supra. In one embodiment, the VH subgroup III consensus framework amino acid sequence comprises at least a portion or all of each of the following sequences: EVQLVESGG-GLVQPGGSLRLSCAAS (HC-FR1)(SEQ ID NO:4), WVRQAPGKGLEWV (HC-FR2), (SEQ ID NO:5), RFTI-SADTSKNTAYLQMNSLRAEDTAVYYCAR (HC-FR3, SEQ ID NO:6), WGQGTLVTVSA (HC-FR4), (SEQ ID NO:7).

A "VL kappa I consensus framework" comprises the consensus sequence obtained from the amino acid sequences in variable light kappa subgroup I of Kabat et al., supra. In one embodiment, the VH subgroup I consensus framework amino acid sequence comprises at least a portion or all of each of the following sequences: DIQMTQSPSSL-SASVGDRVTITC (LC-FR1) (SEQ ID NO:11), WYQQKPGKAPKLLIY (LC-FR2) (SEQ ID NO:12), GVPSRFSGSGSGTDFTLTISSLQPEDFATYYC (LC-FR3) (SEQ ID NO: 13), FGQGTKVEIKR (LC-FR4)(SEQ ID NO:14).

An "amino-acid modification" at a specified position, e.g. of the Fc region, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by VH- and VL-domain shuffling. Random mutagenesis of HVR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

As use herein, the term "specifically binds to" or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of ≤1 µM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2 (including IgG2A and IgG2B), IgG-3, or IgG-4 subtypes, IgA (including IgA-1 and IgA-2), IgE, IgD or IgM. The Ig fusions preferably include the substitution of a domain of a polypeptide or antibody described herein in the place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995. For example, useful immunoadhesins as second medicaments useful for combination therapy herein include polypeptides that comprise the extracellular or PD-1 binding portions of PD-L1 or PD-L2 or the extracellular or PD-L1 or PD-L2 binding portions of PD-1, fused to a constant domain of an immunoglobulin sequence, such as a PD-L1 ECD-Fc, a PD-L2 ECD-Fc, and a PD-1 ECD-Fc, respectively. Immunoadhesin combinations of Ig Fc and ECD of cell surface receptors are sometimes termed soluble receptors.

A "fusion protein" and a "fusion polypeptide" refer to a polypeptide having two portions covalently linked together, where each of the portions is a polypeptide having a different property. The property may be a biological property, such as activity in vitro or in vivo. The property may also be simple chemical or physical property, such as binding to a target molecule, catalysis of a reaction, etc. The two portions may be linked directly by a single peptide bond or through a peptide linker but are in reading frame with each other.

A "PD-1 oligopeptide," "PD-Li oligopeptide," or "PD-L2 oligopeptide" is an oligopeptide that binds, preferably specifically, to a PD-1, PD-L1 or PD-L2 negative costimulatory polypeptide, respectively, including a receptor, ligand or signaling component, respectively, as described herein. Such oligopeptides may be chemically synthesized using known oligopeptide synthesis methodology or may be prepared and purified using recombinant technology. Such oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more. Such oligopeptides may be identified using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., *Proc. Natl. Acad. Sci. U.S.A.*, 81:3998-4002 (1984); Geysen et al., *Proc. Natl. Acad. Sci. U.S.A.*, 82:178-182 (1985); Geysen et al., in *Synthetic Peptides as Antigens,* 130-149 (1986); Geysen et al., *J. Immunol. Meth.*, 102:259-274 (1987); Schoofs et al., *J. Immunol.,* 140:611-616 (1988), Cwirla, S. E. et al. *Proc. Natl. Acad. Sci. USA,* 87:6378 (1990); Lowman, H. B. et al. *Biochemistry,* 30:10832 (1991); Clackson, T. et al. *Nature,* 352: 624 (1991); Marks, J. D. et al., *J. Mol. Biol.,* 222:581 (1991); Kang, A. S. et al. *Proc. Natl. Acad. Sci. USA,* 88:8363 (1991), and Smith, G. P., *Current Opin. Biotechnol.,* 2:668 (1991).

A "blocking" antibody or an "antagonist" antibody is one that inhibits or reduces a biological activity of the antigen it binds. In some embodiments, blocking antibodies or antagonist antibodies substantially or completely inhibit the biological activity of the antigen. The anti-PD-L1 antibodies of the invention block the signaling through PD-1 so as to restore a functional response by T-cells (e.g., proliferation, cytokine production, target cell killing) from a dysfunctional state to antigen stimulation.

An "agonist" or activating antibody is one that enhances or initiates signaling by the antigen to which it binds. In some embodiments, agonist antibodies cause or activate signaling without the presence of the natural ligand.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the invention include human IgG1, IgG2 (IgG2A, IgG2B), IgG3 and IgG4.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see M. Daëron, *Annu. Rev. Immunol.* 15:203-234 (1997). FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin. Med.* 126: 330-41 (1995). Other FcR8, including those to be identified in the future, are encompassed by the term "FcR" herein.

The term "Fe receptor" or "FcR" also includes the neonatal receptor, FcRn, which is responsible for the transfer of maternal IgGs to the fetus. Guyer et al., *J. Immunol.* 117: 587 (1976) and Kim et al., *J. Immunol.* 24: 249 (1994). Methods of measuring binding to FcRn are known (see, e.g., Ghetie and Ward, *Immunol. Today* 18: (12): 592-8 (1997); Ghetie et al., *Nature Biotechnology* 15 (7): 637-40 (1997); Hinton et al., *J. Biol. Chem.* 279 (8): 6213-6 (2004); WO 2004/92219 (Hinton et al.). Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants which improved or diminished binding to FcRs. See also, e.g., Shields et al., *J. Biol. Chem.* 9(2): 6591-6604 (2001).

The phrase "substantially reduced," or "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

The term "substantially similar" or "substantially the same," as used herein, denotes a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., Kd values). The difference between said two values is, for example, less than about 50%, less than about 40%, less than about 30%, less than about 20%, and/or less than about 10% as a function of the reference/comparator value.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

A "package insert" refers to instructions customarily included in commercial packages of medicaments that contain information about the indications customarily included in commercial packages of medicaments that contain information about the indications, usage, dosage, administration, contraindications, other medicaments to be combined with the packaged product, and/or warnings concerning the use of such medicaments, etc.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. For example, an individual is successfully "treated" if one or more symptoms associated with cancer are mitigated or eliminated, including, but are not limited to, reducing the proliferation of (or destroying) cancerous cells, decreasing symptoms resulting from the disease, increasing the quality of life of those suffering from the disease, decreasing the dose of other medications required to treat the disease, delaying the progression of the disease, and/or prolonging survival of individuals.

As used herein, "delaying progression of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

As used herein, "reducing or inhibiting cancer relapse" means to reduce or inhibit tumor or cancer relapse or tumor or cancer progression. As disclosed herein, cancer relapse and/or cancer progression include, without limitation, cancer metastasis.

An "effective amount" is at least the minimum concentration required to effect a measurable improvement or prevention of a particular disorder. An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent or desirably stop) cancer cell infiltration into peripheral organs; inhibit (i.e., slow to some extent and desirably stop) tumor metastasis; inhibiting to some extent tumor growth; and/or relieving to some extent one or more of the symptoms associated with the disorder. An effective amount can be administered in one or more administrations. For purposes of this invention, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, "in conjunction with" refers to administration of one treatment modality in addition to another treatment modality. As such, "in conjunction with" refers to administration of one treatment modality before, during, or after administration of the other treatment modality to the individual.

As used herein, "complete response" or "CR" refers to disappearance of all target lesions; "partial response" or "PR" refers to at least a 30% decrease in the sum of the longest diameters (SLD) of target lesions, taking as reference the baseline SLD; and "stable disease" or "SD" refers to neither sufficient shrinkage of target lesions to qualify for PR, nor sufficient increase to qualify for PD, taking as reference the smallest SLD since the treatment started.

As used herein, "progressive disease" or "PD" refers to at least a 20% increase in the SLD of target lesions, taking as reference the smallest SLD recorded since the treatment started or the presence of one or more new lesions.

As used herein, "progression free survival" (PFS) refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall response rate" (ORR) refers to the sum of complete response (CR) rate and partial response (PR) rate.

As used herein, "overall survival" refers to the percentage of individuals in a group who are likely to be alive after a particular duration of time.

A "chemotherapeutic agent" is a chemical compound useful in the treatment of cancer. Examples of chemotherapeutic agents include alkylating agents such as thiotepa and cyclophosphamide (CYTOXAN®); alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; pemetrexed; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; TLK-286; CDP323, an oral alpha-4 integrin inhibitor; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Nicolaou et al., Angew. Chem Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, and imatinib (a 2-phenylaminopyrimidine derivative), as well as other c-Kit inhibitors; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Additional examples of chemotherapeutic agents include anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); estrogen receptor antagonists such as fulvestrant (FASLODEX®); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, such definition of chemotherapeutic agents includes bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); an anti-estrogen such as fulvestrant; a Kit inhibitor such as imatinib or EXEL-0862 (a tyrosine kinase inhibitor); EGFR inhibitor such as erlotinib or cetuximab; an anti-VEGF inhibitor such as bevacizumab; arinotecan; rmRH (e.g., ABARELIX®); lapatinib and lapatinib ditosylate (an ErbB-2 and EGFR dual tyrosine kinase small-molecule inhibitor also known as GW572016); 17AAG (geldanamycin derivative that is a heat shock protein (Hsp) 90 poison), and pharmaceutically acceptable salts, acids or derivatives of any of the above.

As used herein, the term "cytokine" refers generically to proteins released by one cell population that act on another cell as intercellular mediators or have an autocrine effect on the cells producing the proteins. Examples of such cytokines include lymphokines, monokines; interleukins ("ILs") such as IL-1, IL-1α, IL-2, IL-3, IL-4, IL-5, IL-6, IL-7, IL-8, IL-9, IL10, IL-11, IL-12, IL-13, IL-15, IL-17A-F, IL-18 to IL-29 (such as IL-23), IL-31, including PROLEUKIN® rIL-2; a tumor-necrosis factor such as TNF-α or TNF-β, TGF-β1-3; and other polypeptide factors including leukemia inhibitory factor ("LIF"), ciliary neurotrophic factor ("CNTF"), CNTF-like cytokine ("CLC"), cardiotrophin ("CT"), and kit ligand ("KL").

As used herein, the term "chemokine" refers to soluble factors (e.g., cytokines) that have the ability to selectively induce chemotaxis and activation of leukocytes. They also trigger processes of angiogenesis, inflammation, wound healing, and tumorigenesis. Example chemokines include IL-8, a human homolog of murine keratinocyte chemoattractant (KC).

As used herein and in the appended claims, the singular forms "a," "or," and "the" include plural referents unless the context clearly dictates otherwise.

Reference to "about" a value or parameter herein includes (and describes) variations that are directed to that value or parameter per se. For example, description referring to "about X" includes description of "X".

The term "alkyl" as used herein refers to a saturated linear or branched-chain monovalent hydrocarbon radical of one to twelve carbon atoms. Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 1-heptyl, 1-octyl, and the like.

The term "alkenyl" refers to linear or branched-chain monovalent hydrocarbon radical of two to twelve carbon atoms with at least one site of unsaturation, i.e., a carbon-carbon, sp$^2$ double bond, wherein the alkenyl radical includes radicals having "cis" and "trans" orientations, or alternatively, "E" and "Z" orientations. Examples include, but are not limited to, ethylenyl or vinyl (—CH=CH$_2$), allyl (—CH$_2$CH=CH$_2$), and the like.

The term "alkynyl" refers to a linear or branched monovalent hydrocarbon radical of two to twelve carbon atoms with at least one site of unsaturation, i.e., a carbon-carbon, sp triple bond. Examples include, but are not limited to, ethynyl (—C≡CH), propynyl (propargyl, —CH$_2$C≡CH), and the like.

The terms "carbocycle", "carbocyclyl", "carbocyclic ring" and "cycloalkyl" refer to a monovalent non-aromatic, saturated or partially unsaturated ring having 3 to 12 carbon atoms as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo [2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-18 carbon atoms derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, naphthalene, anthracene, indenyl, indanyl, 1,2-dihydronaphthalene, 1,2,3,4-tetrahydronaphthyl, and the like.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to 18 ring atoms in which at least one ring atom is a heteroatom selected from nitrogen, oxygen and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6]system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidinyl, morpholinyl, thiomorpholinyl, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, and azabicyclo[2.2.2]hexanyl. Spiro moieties are also included within the scope of this definition. Examples of a heterocyclic group wherein ring atoms are substituted with oxo (=O) moieties are pyrimidinonyl and 1,1-dioxo-thiomorpholinyl.

The term "heteroaryl" refers to a monovalent aromatic radical of 5- or 6-membered rings, and includes fused ring systems (at least one of which is aromatic) of 5-18 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The heterocycle or heteroaryl groups may be carbon (carbon-linked) or nitrogen (nitrogen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The heteroatoms present in heteroaryl or heterocyclcyl include the oxidized forms such as $N^+ \rightarrow O^-$, $S(O)$ and $S(O)_2$.

The term "halo" refers to F, Cl, Br or I.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

It is understood that aspects and variations of the invention described herein include "consisting of" and/or "consisting essentially of" aspects and variations.

III. Methods

In one aspect, provided herein is a method for treating or delaying progression of cancer in an individual comprising administering to the individual an effective amount of a PD-1 axis binding antagonist and a MEK inhibitor.

The methods of this invention may find use in treating conditions where enhanced immunogenicity is desired such as increasing tumor immunogenicity for the treatment of cancer. A variety of cancers may be treated, or their progression may be delayed, including but are not limited to a cancer that may contain a B-raf V600E mutation, a cancer that may contain a B-raf wildtype, a cancer that may contain a KRAS wildtype, or a cancer that may contain an activating KRAS mutation.

In some embodiments, the individual has cancer or is at risk of developing cancer that is resistant to a B-raf antagonist. In some embodiments, the individual has been previously treated with a B-raf antagonist for cancer. In some embodiments, the individual has not been previously treated with a B-raf antagonist. B-raf is a serine-threonine kinase known to be frequently mutated in cancer, e.g., malignant melanoma, colorectal, ovarian, and thyroid cancer. Typically, B-raf mutations observed in cancer include activating mutations, such as the V600E mutation. Without wishing to be bound to theory, it is thought that activating mutations in B-raf promote deregulated MAPK/ERK signaling, leading to tumor cell proliferation and survival.

While B-raf antagonists (e.g., B-raf inhibitors) are known to produce effective short-term increases in patient survival and tumor regression, resistance to B-raf inhibition is frequently observed (see, e.g., Tentori, L., et al. Trends Pharmacol. Sci. 34(12):656-66 (2013)). Resistance to B-raf inhibition may be characterized by numerous phenomena. In some embodiments, resistance to B-raf inhibition may be characterized by one or more of MAPK pathway reactivation, PI3K activation, CRAF upregulation, NRAS mutation, PDGFR overexpression, COT1 overexpression, IGFR-1 overexpression, MEK1 mutation, HGF expression, PD-L1 overexpression, MEK2 mutation, MITF focal amplification, AKT mutation (e.g., AKT1 or AKT3), B-raf amplification, and the formation of RAF dimers (e.g., CRAF/CRAF dimers, CRAF/B-raf dimers, and mutated dimerizing B-raf such as a B-raf variant lacking exons 4-8).

In some embodiments, resistance to B-raf inhibition may refer to a cancer cell or tumor that is refractory to B-raf inhibition. Resistance to B-raf inhibition is used herein in the broadest sense and may include any cancer cell that was previously or may be expected to be sensitive to B-raf inhibition through any particular mechanism or at any particular dose of a B-raf antagonist of the present disclosure. Resistance to B-raf inhibition may refer to B-raf activity in the presence of a B-raf antagonist. Resistance to B-raf inhibition may refer to a cell that grows in the presence of a B-raf antagonist when it is not expected to grow under such a condition, regardless of the enzymatic activity of B-raf that may be present.

In some embodiments, the B-raf antagonist is a small molecule inhibitor, an antibody, a peptide, a peptidomimetic, an aptamer or a polynucleotide.

In some embodiments, the individual has previously been treated with a B-raf antagonist. In some embodiments, a B-raf antagonist may include vemurafenib (also known as ZELBORAF®), dabrafenib (also known as TAFINLAR®), LGX818, GSK 2118436, RAF265, XL281, ARQ736, BAY73-4506, sorafenib, PLX4720, PLX-3603, GSK2118436, GDC-0879, or N-(3-(5-(4-chlorophenyl)-1H-pyrrolo [2,3-b]pyridine-3-carbonyl)-2,4-difluorophenyl)propane-1-sulfonamide. In some embodiments, a B-raf antagonist may include MLN2480, LY3009120, a MEK inhibitor such as trametinib (also known as MEKINIST®), or an EGFR inhibitor such as erlotinib (also known as TARCEVA®). Further descriptions of B-raf inhibitors may be found in Zambon, A. et al. Bioorg. Med. Chem. Lett. 22(2):789-92 (2012); Tentori, L., et al. Trends Pharmacol. Sci. 34(12):656-66 (2013); and Martin-Liberal, J. and Larkin, J. Expert Opin. Pharmacother. 15(9):1235-45 (2014), WO2007/002325, WO2007/002433, WO2009111278, WO2009111279, WO2009111277, WO2009111280 and U.S. Pat. No. 7,491,829.

In some embodiments, the B-raf antagonist is a selective B-raf antagonist of B-raf V600. In some embodiments, the selective B-raf antagonist of B-raf V600 is a selective antagonist of B-raf V600E. In some embodiments, the selective B-raf antagonist of B-raf V600 is a selective antagonist of B-raf V600E, B-raf V600K, and/or V600D. In some embodiments, the selective B-raf antagonist of B-raf V600 is a selective antagonist of B-raf V600R. Techniques for generating and assaying B-raf antagonists that are selective for B-raf V600 have been described in the art; see, e.g., Tsai, J, et al., Proc. Natl. Acad. Sci. 105(8):3041-6 (2008).

In some embodiments, the cancer contains a BRAF V600E mutation, a BRAF wildtype, a KRAS wildtype, or an activating KRAS mutation. Methods for detecting the presence of such mutations may include, without limitation, PCR, Sanger sequencing, use of a mutation-specific antibody, and the like. Methods for determining whether a cancer expresses a B-raf V600 are known in the art, including without limitation the COBAS® 4800 B-raf V600 Mutation Test kit (Roche).

In some embodiments, the patient's cancer has been shown to express a B-raf biomarker. In some embodiments, B-raf biomarker is mutant B-raf. In some embodiments, mutant B-raf is B-raf V600. In some embodiments, B-raf V600 is B-raf V600E. In some embodiments, mutant B-raf is constitutively active.

In some embodiments, the cancer patient has progressed while receiving a B-raf antagonist therapy (i.e., the patient is "B-raf refractory"), or the patient has progressed within 1 month, 2 months, 3 months, 4 months, 5, months, 6 months, 7 months, 8 months, 9 months, 10 months, 11, months, 12 months, or more after completing a B-raf antagonist-based therapy regimen.

In some embodiments, vemurafenib resistant cancer is meant that the cancer patient has progressed while receiving vemurafenib-based therapy (i.e., the patient is "vemurafenib refractory"). In some embodiments, cancer in the patient has progressed within 1 month, 2 months, 3 months, 4 months, 5, months, 6 months, 7 months, 8 months, 9 months, 10 months, 11, months, 12 months, or more after completing a vemurafenib-based therapy regimen. In some embodiments, the cancer in the individual has progressed within 1 month, 2 months, 3 months, 4 months, 5, months, 6 months, 7 months, 8 months, 9 months, 10 months, 11, months, 1 year, 2 years, 3 years, 4 years, or 5 years after completing a B-raf antagonist-based therapy regimen.

In some embodiments, the treatment results in a sustained response in the individual after cessation of the treatment.

In some embodiments, resistance to, e.g., B-raf inhibitor develops (is acquired) after treatment with B-raf antagonist. In other embodiments, the patient (e.g., the patient having B-raf resistant cancer) has not been previously treated with a B-raf antagonist.

In some embodiments, the patient is currently being treated with B-raf antagonist, such as a B-raf inhibitor. In some embodiments, the patient was previously treated with B-raf antagonist. In some embodiments, the patient was not previously treated with B-raf antagonist.

In some embodiments, the individual has colorectal cancer, melanoma, lung cancer, ovarian cancer, breast cancer, pancreatic cancer, hematological malignancy, bladder cancer, and/or renal cell carcinoma. In some embodiments, the individual has non-small cell lung cancer. The non-small cell lung cancer may be at early stage or at late stage. In some embodiments, the individual has small cell lung cancer. The small cell lung cancer may be at early stage or at late stage. In some embodiments, the individual has renal cell cancer. The renal cell cancer may be at early stage or at late stage. In some embodiments, the individual has colorectal cancer. The colorectal cancer may be at early stage or late stage. In some embodiments, the individual has ovarian cancer. The ovarian cancer may be at early stage or at late stage. In some embodiments, the individual has breast cancer. The breast cancer may be at early stage or at late stage. In some embodiments, the individual has pancreatic cancer. The pancreatic cancer may be at early stage or at late stage. In some embodiments, the individual has gastric carcinoma. The gastric carcinoma may be at early stage or at late stage.

In some embodiments, the individual has bladder cancer. The bladder cancer may be at early stage or at late stage. In some embodiments, the individual has esophageal cancer. The esophageal cancer may be at early stage or at late stage. In some embodiments, the individual has mesothelioma. The mesothelioma may be at early stage or at late stage. In some embodiments, the individual has melanoma. The melanoma may be at early stage or at late stage. In some embodiments, the individual has head and neck cancer. The head and neck cancer may be at early stage or at late stage. In some embodiments, the individual has thyroid cancer. The thyroid cancer may be at early stage or at late stage. In some embodiments, the individual has sarcoma. The sarcoma may be at early stage or late stage. In some embodiments, the individual has prostate cancer. The prostate cancer may be at early stage or at late stage. In some embodiments, the individual has glioblastoma. The glioblastoma may be at early stage or at late stage. In some embodiments, the individual has cervical cancer. The cervical cancer may be at early stage or at late stage. In some embodiments, the individual has thymic carcinoma. The thymic carcinoma may be at early stage or at late stage. In some embodiments, the individual has leukemia. The leukemia may be at early stage or at late stage. In some embodiments, the individual has lymphomas. The lymphoma may be at early stage or at late stage. In some embodiments, the individual has myelomas. The myelomas may be at early stage or at late stage. In some embodiments, the individual has mycosis fungoides. The mycosis fungoides may be at early stage or at late stage. In some embodiments, the individual has merkel cell cancer. The merkel cell cancer may be at early stage or at late stage. In some embodiments, the individual has hematologic malignancies. The hematological malignancies may be early stage or late stage. In some embodiments, the individual is a human. In some embodiments, the cancer is metastatic.

In some embodiments, the individual is a mammal, such as domesticated animals (e.g., cows, sheep, cats, dogs, and horses), primates (e.g., humans and non-human primates such as monkeys), rabbits, and rodents (e.g., mice and rats). In some embodiments, the individual treated is a human.

In another aspect, provided herein is a method of enhancing immune function in an individual having cancer comprising administering an effective amount of a PD-1 axis binding antagonist and a MEK inhibitor.

In some embodiments, the CD8 T cells in the individual have enhanced priming, activation, proliferation and/or cytolytic activity relative to prior to the administration of the PD-1 pathway antagonist and the MEK inhibitor. In some embodiments, the CD8 T cell priming is characterized by elevated CD44 expression and/or enhanced cytolytic activity in CD8 T cells. In some embodiments, the CD8 T cell activation is characterized by an elevated frequency of $\gamma$-IFN$^+$ CD8 T cells. In some embodiments, the CD8 T cell is an antigen-specific T-cell. In some embodiments, the immune evasion by signaling through PD-L1 surface expression is inhibited.

In some embodiments, the cancer cells in the individual have elevated expression of MHC class I antigen expression relative to prior to the administration of the PD-1 pathway antagonist and the MEK inhibitor.

In some embodiments, the antigen presenting cells in the individual have enhanced maturation and activation relative prior to the administration of the PD-1 pathway antagonist and the MEK inhibitor. In some embodiments, wherein the antigen presenting cells are dendritic cells. In some embodiments, the maturation of the antigen presenting cells is characterized by increased frequency of CD83$^+$ dendritic cells. In some embodiments, the activation of the antigen presenting cells is characterized by elevated expression of CD80 and CD86 on dendritic cells.

In some embodiments, the serum levels of cytokine IL-10 and/or chemokine IL-8, a human homolog of murine KC, in the individual are reduced relative prior to the administration of the anti-PD-L1 antibody and the MEK inhibitor.

In some embodiments, the cancer has elevated levels of T-cell infiltration.

In some embodiments, the combination therapy of the invention comprises administration of a PD-1 axis binding antagonist and a MEK inhibitor. The PD-1 axis binding antagonist and the MEK inhibitor may be administered in any suitable manner known in the art. For example, The PD-1 axis binding antagonist and the MEK inhibitor may be administered sequentially (at different times) or concurrently (at the same time).

In some embodiments, the MEK inhibitor is administered continuously. In some embodiments, the MEK inhibitor is administered intermittently. In some embodiments, the MEK inhibitor is administered before administration of the PD-1 axis binding antagonist. In some embodiments, the MEK inhibitor is administered simultaneously with administration of the PD-1 axis binding antagonist. In some embodiments, the MEK inhibitor is administered after administration of the PD-1 axis binding antagonist.

In some embodiments, provided is a method for treating or delaying progression of cancer in an individual comprising administering to the individual an effective amount of a PD-1 axis binding antagonist and a MEK inhibitor, further comprising administering an additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy. In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PI3K/AKT/mTOR pathway, HSP90 inhibitor, tubulin inhibitor, apoptosis inhibitor, and/or chemopreventative agent. The additional therapy may be one or more of the chemotherapeutic agents described hereabove.

The PD-1 axis binding antagonist and the MEK inhibitor may be administered by the same route of administration or by different routes of administration. In some embodiments, the PD-1 axis binding antagonist is administered intravenously, intramuscularly, subcutaneously, topically, orally, transdermally, intraperitoneally, intraorbitally, by implantation, by inhalation, intrathecally, intraventricularly, or intranasally. In some embodiments, the MEK inhibitor is administered intravenously, intramuscularly, subcutaneously, topically, orally, transdermally, intraperitoneally, intraorbitally, by implantation, by inhalation, intrathecally, intraventricularly, or intranasally. An effective amount of the PD-1 axis binding antagonist and the MEK inhibitor may be administered for prevention or treatment of disease. The appropriate dosage of the PD-1 axis binding antagonist and/or the MEK inhibitor may be determined based on the type of disease to be treated, the type of the PD-1 axis binding antagonist and the MEK inhibitor, the severity and course of the disease, the clinical condition of the individual, the individual's clinical history and response to the treatment, and the discretion of the attending physician.

Any of the PD-1 axis binding antagonists and the MEK inhibitors known in the art or described below may be used in the methods.

PD-1 Axis Binding Antagonists

Provided herein is a method for treating or delaying progression of cancer in an individual comprising administering to the individual an effective amount of a PD-1 axis binding antagonist and a MEK inhibitor. For example, a PD-1 axis binding antagonist includes a PD-1 binding antagonist, a PD-L1 binding antagonist and a PD-L2 binding antagonist. Alternative names for "PD-1" include CD279 and SLEB2. Alternative names for "PD-L" include B7-H1, B7-4, CD274, and B7-H. Alternative names for "PD-L2" include B7-DC, Btdc, and CD273. In some embodiments, PD-1, PD-L1, and PD-L2 are human PD-1, PD-L1 and PD-L2.

In some embodiments, the PD-1 binding antagonist is a molecule that inhibits the binding of PD-1 to its ligand binding partners. In a specific aspect the PD-1 ligand binding partners are PD-L1 and/or PD-L2. In another embodiment, a PD-L1 binding antagonist is a molecule that inhibits the binding of PD-L1 to its binding partners. In a specific aspect, PD-L1 binding partners are PD-1 and/or B7-1. In another embodiment, the PD-L2 binding antagonist is a molecule that inhibits the binding of PD-L2 to its binding partners. In a specific aspect, a PD-L2 binding partner is PD-1. The antagonist may be an antibody, an antigen binding fragment thereof, an immunoadhesin, a fusion protein, or oligopeptide.

In some embodiment, the PD-1 binding antagonist is an anti-PD-1 antibody (e.g., a human antibody, a humanized antibody, or a chimeric antibody). In some embodiments, the anti-PD-1 antibody is selected from the group consisting of MDX-1106 (nivolumab, OPDIVO®), Merck 3745 (MK-3475, pembrolizumab, KEYTRUDA®), CT-011 (pidilizumab), MEDI-0680 (AMP-514), PDR001, REGN2810, BGB-108, and BGB-A317. In some embodiments, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 binding antagonist is AMP-224. In some embodiments, the PD-L1 binding antagonist is anti-PD-L1 antibody. In some embodiments, the anti-PD-L1 binding antagonist is selected from the group consisting of YW243.55.S70, MPDL3280A (atezolizumab), MEDI4736 (durvalumab), MDX-1105, and MSB0010718C (avelumab). MDX-1105, also known as BMS-936559, is an anti-PD-L1 antibody described in WO2007/005874. Antibody YW243.55.S70 (heavy and light chain variable region sequences shown in SEQ ID Nos: 20 and 21, respectively) is an anti-PD-L1 described in WO 2010/077634 A1. MEDI4736 is an anti-PD-L1 antibody described in WO2011/066389 and US2013/034559. MDX-1106, also known as nivolumab, MDX-1106-04, ONO-4538, BMS-936558, or OPDIVO®, is an anti-PD-1 antibody described in WO2006/121168. Merck 3745, also known as MK-3475, pembrolizumab, lambrolizumab, KEYTRUDA®, or SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PD-L2-Fc fusion soluble receptor described in WO2010/027827 and WO2011/066342.

In some embodiments, the anti-PD-1 antibody is MDX-1106. Alternative names for "MDX-1106" include MDX-1106-04, ONO-4538, BMS-936558 or nivolumab. In some embodiments, the anti-PD-1 antibody is Nivolumab (CAS Registry Number: 946414-94-4). In a still further embodiment, provided is an isolated anti-PD-1 antibody comprising a heavy chain variable region comprising the heavy chain variable region amino acid sequence from SEQ ID NO:22 and/or a light chain variable region comprising the light chain variable region amino acid sequence from SEQ ID NO:23. In a still further embodiment, provided is an isolated anti-PD-1 antibody comprising a heavy chain and/or a light chain sequence, wherein:

(a) the heavy chain sequence has at least 85%, at least 90%, at least 91%, at least 92%, at least 93%, at least 94%, at least 95%, at least 96%, at least 97%, at least 98%, at least 99% or 100% sequence identity to the heavy chain sequence:

```
(SEQ ID NO: 22)
QVQLVESGGGVVQPGRSLRLDCKASGITFSNSGMHWVRQAPGKGLEWVAVI
WYDGSKRYYADSVKGRFTISRDNSKNTLFLQMNSLRAEDTAVYYCATNDDY
WGQGTLVTVSSASTKGPSVFPLAPCSRSTSESTAALGCLVKDYFPEPVTVS
WNSGALTSGVHTFPAVLQSSGLYSLSSVVTVPSSSLGTKTYTCNVDHKPSN
TKVDKRVESKYGPPCPPCPAPEFLGGPSVFLFPPKPKDTLMISRTPEVTCV
VVDVSQEDPEVQFNWYVDGVEVHNAKTKPREEQFNSTYRVVSVLTVLHQDW
LNGKEYKCKVSNKGLPSSIEKTISKAKGQPREPQVYTLPPSQEEMTKNQVS
LTCLVKGFYPSDIAVEWESNGQPENNYKTTPPVLDSDGSFFLYSRLTVDKS
RWQEGNVFSCSVMHEALHNHYTQKSLSLSLGK,
```
or (b) the light chain sequences has at least 85%, at least 90%, at least 91%, at least 92%, at least 93%, at least 94%, at least 95%, at least 96%, at least 97%, at least 98%, at least 99% or 100% sequence identity to the light chain sequence:

```
(SEQ ID NO: 23)
EIVLTQSPATLSLSPGERATLSCRASQSVSSYLAWYQQKPGQAPRLLIYD
ASNRATGIPARFSGSGSGTDFTLTISSLEPEDFAVYYCQQSSNWPRTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC.
```

Examples of anti-PD-L1 antibodies useful for the methods of this invention, and methods for making thereof are described in PCT patent application WO 2010/077634 A1, which is incorporated herein by reference.

In some embodiments, the PD-1 axis binding antagonist is an anti-PD-L1 antibody. In some embodiments, the anti-PD-L1 antibody is capable of inhibiting binding between PD-L1 and PD-1 and/or between PD-L1 and B7-1. In some embodiments, the anti-PD-L1 antibody is a monoclonal antibody. In some embodiments, the anti-PD-L1 antibody is an antibody fragment selected from the group consisting of Fab, Fab'-SH, Fv, scFv, and (Fab')$_2$ fragments. In some embodiments, the anti-PD-L1 antibody is a humanized antibody. In some embodiments, the anti-PD-L1 antibody is a human antibody.

The anti-PD-L1 antibodies useful in this invention, including compositions containing such antibodies, such as those described in WO 2010/077634 A1, may be used in combination with a MEK inhibitor to treat cancer. In some embodiments, the anti-PD-L1 antibody comprises a heavy chain variable region comprising the amino acid sequence of SEQ ID NO:20 and a light chain variable region comprising the amino acid sequence of SEQ ID NO:21.

In one embodiment, the anti-PD-L1 antibody contains a heavy chain variable region polypeptide comprising an HVR-H1, HVR-H2 and HVR-H3 sequence, wherein:
(a) the HVR-H1 sequence is GFTFSX$_1$SWIH (SEQ ID NO:1);
(b) the HVR-H2 sequence is AWIX$_2$PYGGSX$_3$YYADSVKG (SEQ ID NO:2);
(c) the HVR-H3 sequence is RHWPGGFDY (SEQ ID NO:3);
further wherein: X$_1$ is D or G; X$_2$ is S or L; X$_3$ is T or S.

In one specific aspect, X$_1$ is D; X$_2$ is S and X$_3$ is T. In another aspect, the polypeptide further comprises variable region heavy chain framework sequences juxtaposed between the HVRs according to the formula: (HC-FR1)-(HVR-H1)-(HC-FR2)-(HVR-H2)-(HC-FR3)-(HVR-H3)-(HC-FR4). In yet another aspect, the framework sequences are derived from human consensus framework sequences. In a further aspect, the framework sequences are VH subgroup III consensus framework. In a still further aspect, at least one of the framework sequences is the following:

```
                                         (SEQ ID NO: 4)
HC-FR1 is EVQLVESGGGLVQPGGSLRLSCAAS (SEQ ID NO: 5)
HC-FR2 is WVRQAPGKGLEWV (SEQ ID NO: 6)
HC-FR3 is RFTISADTSKNTAYLQMNSLRAEDTAVYYCAR (SEQ ID NO: 7)
HC-FR4 is WGQGTLVTVSA.
```

In a still further aspect, the heavy chain polypeptide is further combined with a variable region light chain comprising an HVR-L1, HVR-L2 and HVR-L3, wherein:
(a) the HVR-L1 sequence is RASQX$_4$X$_5$X$_6$TX$_7$X$_8$A (SEQ ID NO:8);
(b) the HVR-L2 sequence is SASX$_9$LX$_{10}$S, (SEQ ID NO:9);
(c) the HVR-L3 sequence is QQX$_{11}$X$_{12}$X$_{13}$X$_{14}$PX$_{15}$T (SEQ ID NO:10);
further wherein: X$_4$ is D or V; X$_5$ is V or I; X$_6$ is S or N; X$_7$ is A or F; X$_8$ is V or L; X$_9$ is F or T; X$_{10}$ is Y or A; X$_{11}$ is Y, G, F, or S; X$_{12}$ is L, Y, F or W; X$_{13}$ is Y, N, A, T, G, F or I; X$_{14}$ is H, V, P, T or I; X$_{15}$ is A, W, R, P or T.

In a still further aspect, X$_4$ is D; X$_5$ is V; X$_6$ is S; X$_7$ is A; X$_8$ is V; X$_9$ is F; X$_{10}$ is Y; X$_{11}$ is Y; X$_{12}$ is L; X$_{13}$ is Y; X$_{14}$ is H; X$_{15}$ is A. In a still further aspect, the light chain further comprises variable region light chain framework sequences juxtaposed between the HVRs according to the formula: (LC-FR1)-(HVR-L1)-(LC-FR2)-(HVR-L2)-(LC-FR3)-(HVR-L3)-(LC-FR4). In a still further aspect, the framework sequences are derived from human consensus framework sequences. In a still further aspect, the framework sequences are VL kappa I consensus framework. In a still further aspect, at least one of the framework sequence is the following:

```
                                         (SEQ ID NO: 11)
LC-FR1 is DIQMTQSPSSLSASVGDRVTITC (SEQ ID NO: 12)
LC-FR2 is WYQQKPGKAPKLLIY (SEQ ID NO: 13)
LC-FR3 is GVPSRFSGSGSGTDFTLTISSLQPEDFATYYC (SEQ ID NO: 14)
LC-FR4 is FGQGTKVEIKR.
```

In another embodiment, provided is an isolated anti-PD-L1 antibody or antigen binding fragment comprising a heavy chain and a light chain variable region sequence, wherein:
(a) the heavy chain comprises and HVR-H1, HVR-H2 and HVR-H3, wherein further:
  (i) the HVR-H1 sequence is GFTFSX$_1$SWIH; (SEQ ID NO:1)
  (ii) the HVR-H2 sequence is AWIX$_2$PYGGSX$_3$YYADSVKG (SEQ ID NO:2)
  (iii) the HVR-H3 sequence is RHWPGGFDY, and (SEQ ID NO:3)
(b) the light chain comprises and HVR-L1, HVR-L2 and HVR-L3, wherein further:
  (i) the HVR-L1 sequence is RASQX$_4$X$_5$X$_6$TX$_7$X$_8$A (SEQ ID NO:8)
  (ii) the HVR-L2 sequence is SASX$_9$LX$_{10}$S; and (SEQ ID NO:9)
  (iii) the HVR-L3 sequence is QQX$_{11}$X$_{12}$X$_{13}$X$_{14}$PX$_{15}$T; (SEQ ID NO:10)

Further wherein: X$_1$ is D or G; X$_2$ is S or L; X$_3$ is T or S; X$_4$ is D or V; X$_5$ is V or I; X$_6$ is S or N; X$_7$ is A or F; X$_8$ is V or L; X$_9$ is F or T; X$_{10}$ is Y or A; X$_{11}$ is Y, G, F, or S; X$_{12}$ is L, Y, F or W; X$_{13}$ is Y, N, A, T, G, F or I; X$_{14}$ is H, V, P, T or I; X$_{15}$ is A, W, R, P or T.

In a specific aspect, X$_1$ is D; X$_2$ is S and X$_3$ is T. In another aspect, X$_4$ is D; X$_5$ is V; X$_6$ is S; X$_7$ is A; X$_8$ is V; X$_9$ is F; X$_{10}$ is Y; X$_{11}$ is Y; X$_{12}$ is L; X$_{13}$ is Y; X$_{14}$ is H; X$_{15}$ is A. In yet another aspect, X$_1$ is D; X$_2$ is S and X$_3$ is T, X$_4$ is D; X$_5$ is V; X$_6$ is S; X$_7$ is A; X$_5$ is V; X$_9$ is F; X$_{10}$ is Y; X$_{11}$ is Y; X$_{12}$ is L; X$_{13}$ is Y; X$_{14}$ is H and X$_{15}$ is A.

In a further aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In a still further aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
                                                 (SEQ ID NO: 4)
HC-FR1 is EVQLVESGGGLVQPGGSLRLSCAAS (SEQ ID NO: 5)
HC-FR2 is WVRQAPGKGLEWV (SEQ ID NO: 6)
HC-FR3 is RFTISADTSKNTAYLQMNSLRAEDTAVYYCAR (SEQ ID NO: 7)
HC-FR4 is WGQGTLVTVSA.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
                                                 (SEQ ID NO: 11)
LC-FR1 is DIQMTQSPSSLSASVGDRVTITC (SEQ ID NO: 12)
LC-FR2 is WYQQKPGKAPKLLIY (SEQ ID NO: 13)
LC-FR3 is GVPSRFSGSGSGTDFTLTISSLQPEDFATYYC (SEQ ID NO: 14)
LC-FR4 is FGQGTKVEIKR.
```

In a still further specific aspect, the antibody further comprises a human or murine constant region. In a still further aspect, the human constant region is selected from the group consisting of IgG1, IgG2, IgG2, IgG3, and IgG4. In a still further specific aspect, the human constant region is IgG1. In a still further aspect, the murine constant region is selected from the group consisting of IgG1, IgG2A, IgG2B, and IgG3. In a still further aspect, the murine constant region if IgG2A. In a still further specific aspect, the antibody has reduced or minimal effector function. In a still further specific aspect the minimal effector function results from an "effector-less Fc mutation" or aglycosylation. In still a further embodiment, the effector-less Fc mutation is an N297A or D265A/N297A substitution in the constant region.

In yet another embodiment, provided is an anti-PD-L1 antibody comprising a heavy chain and a light chain variable region sequence, wherein:
(a) the heavy chain further comprises and HVR-H1, HVR-H2 and an HVR-H3 sequence having at least 85% sequence identity to GFTFSDSWIH (SEQ ID NO:15), AWISPYGGSTYYADSVKG (SEQ ID NO:16) and RHWPGGFDY (SEQ ID NO:3), respectively, or
(b) the light chain further comprises an HVR-L1, HVR-L2 and an HVR-L3 sequence having at least 85% sequence identity to RASQDVSTAVA (SEQ ID NO: 17), SASFLYS (SEQ ID NO:18) and QQYLYHPAT (SEQ ID NO:19), respectively.

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
                                                 (SEQ ID NO: 4)
HC-FR1 is EVQLVESGGGLVQPGGSLRLSCAAS (SEQ ID NO: 5)
HC-FR2 is WVRQAPGKGLEWV (SEQ ID NO: 6)
HC-FR3 is RFTISADTSKNTAYLQMNSLRAEDTAVYYCAR (SEQ ID NO: 7)
HC-FR4 is WGQGTLVTVSA.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
                                                 (SEQ ID NO: 11)
LC-FR1 is DIQMTQSPSSLSASVGDRVTITC (SEQ ID NO: 12)
LC-FR2 is WYQQKPGKAPKLLIY (SEQ ID NO: 13)
LC-FR3 is GVPSRFSGSGSGTDFTLTISSLQPEDFATYYC (SEQ ID NO: 14)
LC-FR4 is FGQGTKVEIKR.
```

In a still further specific aspect, the antibody further comprises a human or murine constant region. In a still further aspect, the human constant region is selected from the group consisting of IgG1, IgG2, IgG2, IgG3, and IgG4. In a still further specific aspect, the human constant region is IgG1. In a still further aspect, the murine constant region is selected from the group consisting of IgG1, IgG2A, IgG2B, and IgG3. In a still further aspect, the murine constant region if IgG2A. In a still further specific aspect, the antibody has reduced or minimal effector function. In a still further specific aspect the minimal effector function results from an "effector-less Fc mutation" or aglycosylation. In still a further embodiment, the effector-less Fc mutation is an N297A or D265A/N297A substitution in the constant region.

In a still further embodiment, provided is an isolated anti-PD-Li antibody comprising a heavy chain and a light chain variable region sequence, wherein:
(a) the heavy chain sequence has at least 85% sequence identity to the heavy chain sequence: EVQLVESGG-GLVQPGGSLRLSCAASGFTFSD-SWIHWVRQAPGKGLEWVAWIS PYGGSTYY-ADSVKGRFTISADTSKNTAYLQMNSLRAEDTAV-YYCARRHWPGGFDYWG QGTLVTVSA (SEQ ID NO:20), or
(b) the light chain sequence has at least 85% sequence identity to the light chain sequence: DIQMTQSPSSL-SASVGDRVTITCRASQDVSTA-VAWYQQKPGKAPKLLIY SASF LYSGVPSRFSGSGSGTDFTLTISSLQPEDFA-TYYCQQYLYHPATFGQGTKVEIKR (SEQ ID NO:21).

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
                                        (SEQ ID NO: 4)
HC-FR1 is EVQLVESGGGLVQPGGSLRLSCAAS (SEQ ID NO: 5)
HC-FR2 is WVRQAPGKGLEWV (SEQ ID NO: 6)
HC-FR3 is RFTISADTSKNTAYLQMNSLRAEDTAVYYCAR (SEQ ID NO: 7)
HC-FR4 is WGQGTLVTVSA.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
                                        (SEQ ID NO: 11)
LC-FR1 is DIQMTQSPSSLSASVGDRVTITC (SEQ ID NO: 12)
LC-FR2 is WYQQKPGKAPKLLIY (SEQ ID NO: 13)
LC-FR3 is GVPSRFSGSGSGTDFTLTISSLQPEDFATYYC (SEQ ID NO: 14)
LC-FR4 is FGQGTKVEIKR.
```

In a still further specific aspect, the antibody further comprises a human or murine constant region. In a still further aspect, the human constant region is selected from the group consisting of IgG1, IgG2, IgG2, IgG3, and IgG4. In a still further specific aspect, the human constant region is IgG1. In a still further aspect, the murine constant region is selected from the group consisting of IgG1, IgG2A, IgG2B, and IgG3. In a still further aspect, the murine constant region if IgG2A. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation. In still a further embodiment, the effector-less Fc mutation is an N297A or D265A/N297A substitution in the constant region.

In another further embodiment, provided is an isolated anti-PD-L1 antibody comprising a heavy chain and a light chain variable region sequence, wherein:

(a) the heavy chain sequence has at least 85% sequence identity to the heavy chain sequence: EVQLVESGG-GLVQPGGSLRLSCAASGFTFSD-SWIHWVRQAPGKGLEWVAWIS PYGGSTYY-ADSVKGRFTISADTSKNTAYLQMNS LRAEDTAVYYCARRHWPGGFDYWG QGTLVTVSS (SEQ ID NO:24), or (b) the light chain sequence has at least 85% sequence identity to the light chain sequence: DIQMTQSPSSL-SASVGDRVTITCRASQDVSTA-VAWYQQKPGKAPKLLIY SASF LYSGVPSRFSGSGSGTDFTLTISSLQPEDFA-TYYCQQYLYHPATFGQGTKVEIKR (SEQ ID NO:21).

In a still further embodiment, provided is an isolated anti-PDL1 antibody comprising a heavy chain and a light chain variable region sequence, wherein:

(a) the heavy chain sequence has at least 85% sequence identity to the heavy chain sequence: EVQLVESGG-GLVQPGGSLRLSCAASGFTFSD-SWIHWVRQAPGKGLEWVAWI SPYGGSTYY-ADSVKGRFTISADTSKNTAYLQMNSLRAEDTAV-YYCARRHWPGGFDYW GQGTLVTVSSASTK (SEQ ID NO:28), or (b) the light chain sequence has at least 85% sequence identity to the light chain sequence: DIQMTQSPSSL-SASVGDRVTITCRASQDVSTA-VAWYQQKPGKAPKLLIYSASFLYSGVPS RFSGSGSGTDFTLTISSLQPEDFATYYCQQYLYH-PATFGQGTKVEIKR (SEQ ID NO:21).

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
                                        (SEQ ID NO: 4)
HC-FR1 is EVQLVESGGGLVQPGGSLRLSCAAS (SEQ ID NO: 5)
HC-FR2 is WVRQAPGKGLEWV (SEQ ID NO: 6)
HC-FR3 is RFTISADTSKNTAYLQMNSLRAEDTAVYYCAR (SEQ ID NO: 25)
HC-FR4 is WGQGTLVTVSS.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
LC-FR1 is DIQMTQSPSSLSASVGDRVTITC          (SEQ ID NO: 11)

LC-FR2 is WYQQKPGKAPKLLIY                  (SEQ ID NO: 12)

LC-FR3 is GVPSRFSGSGSGTDFTLTISSLQPEDFATYYC (SEQ ID NO: 13)

LC-FR4 is FGQGTKVEIKR.                     (SEQ ID NO: 14)
```

In a still further specific aspect, the antibody further comprises a human or murine constant region. In a still further aspect, the human constant region is selected from the group consisting of IgG1, IgG2, IgG2, IgG3, and IgG4. In a still further specific aspect, the human constant region is IgG1. In a still further aspect, the murine constant region is selected from the group consisting of IgG1, IgG2A, IgG2B, and IgG3. In a still further aspect, the murine constant region if IgG2A. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation. In still a further embodiment, the effector-less Fc mutation is an N297A or D265A/N297A substitution in the constant region.

In yet another embodiment, the anti-PD-1 antibody is MPDL3280A (atezolizumab). In a still further embodiment, provided is an isolated anti-PD-1 antibody comprising a heavy chain variable region comprising the heavy chain variable region amino acid sequence from SEQ ID NO:24 and/or a light chain variable region comprising the light chain variable region amino acid sequence from SEQ ID NO:25. In a still further embodiment, provided is an isolated anti-PD-1 antibody comprising a heavy chain and/or a light chain sequence, wherein:

(a) the heavy chain sequence has at least 85%, at least 90%, at least 91%, at least 92%, at least 93%, at least 94%, at least 95%, at least 96%, at least 97%, at least 98%, at least 99% or 100% sequence identity to the heavy chain sequence: EVQLVESGG-GLVQPGGSLRLSCAASGFTFSD-SWIHWVRQAPGKGLEWVAWISPYGGST YYADSVKGRFTISADTSKNTAYLQMNSLRAED-TAVYYCARRHWPGGFDYWGQGTLVT VSSAS-TKGPSVFPLAPSSKSTSGGTAALGCLVKDYF-PEPVTVSWNSGALTSGVHTFPAVL QSSGLYS-LSSVVTVPSSSLGTQTYICNVNHKPSNTKVDKK-VEPKSCDKTHTCPPCPAPEL LGGPSVFLFPPKPKDTLMISRTPE-VTCVVVDVSHEDPE-VKFNWYVDGVEVHNAKTKPR EEQYASTYRVVSVLTVLHQDWLNGKEYKCKVS-NKALPAPIEKTISKAKGQPREPQVYT LPPS-REEMTKNQVSLTCLVKGFYPSDIAVEWESNGQ-PENNYKTTPPVLDSDGSFFLYSK LTVDKSRWQQGNVFSCSVMHEALHN-HYTQKSLSLSPGK (SEQ ID NO:26), or (b) the light chain sequences has at least 85%, at least 90%, at least 91%, at least 92%, at least 93%, at least 94%, at least 95%, at least 96%, at least 97%, at least 98%, at least 99% or 100% sequence identity to the light chain sequence:

```
                                           (SEQ ID NO: 27)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.
```

In a still further embodiment, the invention provides for compositions comprising any of the above described anti-PD-L1 antibodies in combination with at least one pharmaceutically-acceptable carrier.

In a still further embodiment, provided is an isolated nucleic acid encoding a light chain or a heavy chain variable region sequence of an anti-PD-L1 antibody, wherein:

(a) the heavy chain further comprises and HVR-H1, HVR-H2 and an HVR-H3 sequence having at least 85% sequence identity to GFTFSDSWIH (SEQ ID NO:15), AWISPYGGSTYYADSVKG (SEQ ID NO:16) and RHWPGGFDY (SEQ ID NO:3), respectively, and (b) the light chain further comprises an HVR-L1, HVR-L2 and an HVR-L3 sequence having at least 85% sequence identity to RASQDVSTAVA (SEQ ID NO: 17), SASFLYS (SEQ ID NO:18) and QQYLYHPAT (SEQ ID NO:19), respectively.

In a specific aspect, the sequence identity is 86%, 87%, 88%, 89%, 90%, 91%, 92%, 93%, 94%, 95%, 96%, 97%, 98%, 99% or 100%. In aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
HC-FR1 is EVQLVESGGGLVQPGGSLRLSCAAS   (SEQ ID NO: 4)

HC-FR2 is WVRQAPGKGLEWV                (SEQ ID NO: 5)

HC-FR3 is RFTISADTSKNTAYLQMNSLRAEDTAVYYCAR (SEQ ID NO: 6)

HC-FR4 is WGQGTLVTVSA.                 (SEQ ID NO: 7)
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
LC-FR1 is DIQMTQSPSSLSASVGDRVTITC          (SEQ ID NO: 11)

LC-FR2 is WYQQKPGKAPKLLIY                  (SEQ ID NO: 12)

LC-FR3 is GVPSRFSGSGSGTDFTLTISSLQPEDFATYYC (SEQ ID NO: 13)

LC-FR4 is FGQGTKVEIKR.                    (SEQ ID NO: 14)
```

In a still further specific aspect, the antibody described herein (such as an anti-PD-1 antibody, an anti-PD-L1 antibody, or an anti-PD-L2 antibody) further comprises a human or murine constant region. In a still further aspect, the human constant region is selected from the group consisting of IgG1, IgG2, IgG2, IgG3, and IgG4. In a still further specific aspect, the human constant region is IgG1. In a still further aspect, the murine constant region is selected from the group consisting of IgG1, IgG2A, IgG2B, and IgG3. In a still further aspect, the murine constant region if IgG2A. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation. In still a further aspect, the effector-less Fc mutation is an N297A or D265A/N297A substitution in the constant region.

In a still further aspect, provided herein are nucleic acids encoding any of the antibodies described herein. In some embodiments, the nucleic acid further comprises a vector suitable for expression of the nucleic acid encoding any of the previously described anti-PD-L1, anti-PD-1, or anti-PD-L2 antibodies. In a still further specific aspect, the vector further comprises a host cell suitable for expression of the nucleic acid. In a still further specific aspect, the host cell is a eukaryotic cell or a prokaryotic cell. In a still further specific aspect, the eukaryotic cell is a mammalian cell, such as Chinese Hamster Ovary (CHO).

The antibody or antigen binding fragment thereof, may be made using methods known in the art, for example, by a process comprising culturing a host cell containing nucleic acid encoding any of the previously described anti-PD-L1, anti-PD-1, or anti-PD-L2 antibodies or antigen-binding fragment in a form suitable for expression, under conditions suitable to produce such antibody or fragment, and recovering the antibody or fragment.

In a still further embodiment, the invention provides for a composition comprising an anti-PD-L1, an anti-PD-1, or an anti-PD-L2 antibody or antigen binding fragment thereof as provided herein and at least one pharmaceutically acceptable carrier. In some embodiments, the anti-PD-L1, anti-PD-1, or anti-PD-L2 antibody or antigen binding fragment thereof administered to the individual is a composition comprising one or more pharmaceutically acceptable carrier. Any of the pharmaceutically acceptable carrier described herein or known in the art may be used.

MEK Inhibitors

The invention provides methods for treating cancer or slowing progression of cancer in an individual comprising administering an effective amount of a PD-1 pathway antagonist and a MEK inhibitor. Any known MEK inhibitors are intended, such as the MEK inhibitor compounds described in PCT patent applications WO 03/077914 A1, WO 2005/121142 A1, WO 2007/044515 A1, WO 2008/024725 A1 and WO 2009/085983 A1, the content of which are incorporated herein by reference. The MEK inhibitor administered may be in a pharmaceutical composition or formulation. In some embodiments, the pharmaceutical composition or formulation comprises one or more MEK inhibitors described herein and a pharmaceutically acceptable carrier or excipient.

In some embodiments, the MEK inhibitor is a competitive inhibitor of MEK. In some embodiments, the MEK inhibitor is more selective against an activating KRAS mutation. In some embodiments, the MEK inhibitor is an allosteric inhibitor of MEK. In some embodiments, the MEK inhibitor is more selective against an activating B-raf mutation (e.g., B-raf V600E mutation). In some embodiments, the MEK inhibitor binds and inhibits the activity of MEK1 and/or MEK2 (such as human MEK1 and/or human MEK2).

In some embodiments, the MEK inhibitor is a compound selected from the group consisting of GDC-0973 (also known as "Cobimetinib" or "XL518"), G-38963, G02443714 (also known as "AS703206"), G02442104 (also known as "GSK-1120212"), and G00039805 (also known as "AZD-6244"), or a pharmaceutically acceptable salt or solvate thereof.

In some embodiments, the MEK inhibitor is a compound of formula (I),

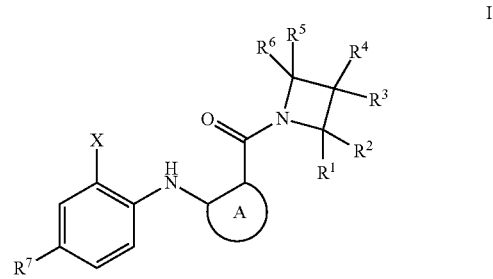

or a pharmaceutically acceptable salt or solvate thereof, wherein A, X, $R^1$, $R^2$, $R^3$, $R^4$, $R^5$, $R^6$, and $R^7$ are as defined in Group A, Group B, Group C, or Group D:

Group A:

A is arylene optionally substituted with one, two, three or four groups selected from $R^{10}$, $R^{12}$, $R^{14}$, $R^{16}$, and $R^{19}$ where $R^{10}$, $R^{12}$, $R^{14}$ and $R^{16}$ are independently hydrogen, alkyl, alkenyl, alkynyl, halo, haloalkoxy, hydroxy, alkoxy, amino, alkylamino, dialkylamino, haloalkyl, —NHS(O)$_2$R$^8$, —CN, —C(O)R$^8$, —C(O)OR$^8$, —C(O)NR$^8$R$^{8'}$ and —NR$^8$C(O)R$^{8'}$ and where $R^{19}$ is hydrogen, alkyl, or alkenyl;

X is alkyl, halo, haloalkyl, or haloalkoxy;

$R^1$, $R^2$, $R^3$, $R^4$, $R^5$ and $R^6$ are independently hydrogen, halo, nitro, —NR$^8$R$^{8'}$, —OR$^8$, —NHS(O)$_2$R$^8$, —CN, —S(O)$_m$R$^8$, —S(O)$_2$NR$^8$R$^{8'}$, —C(O)R$^8$, —C(O)OR$^8$, —C(O)NR$^8$R$^{8'}$, —NR$^8$C(O)OR$^{8'}$, —NR$^8$C(O)NR$^8$R$^{8''}$, —NR$^8$C(O)OR$^{8'}$, —NR$^8$C(O)R$^{8'}$, —CH$_2$N(R$^{25}$)(NR$^{25a}$R$^{25b}$), —CH$_2$NR$^{25}$C(=NH)(NR$^{25a}$R$^{25b}$), —CH$_2$NR$^{25}$C(=NH)(N(R$^{25a}$)(NO$_2$)), —CH$_2$NR$^2$C(=NH)(N(R$^{25a}$)(CN)), —CH$_2$NR$^{25}$C(=NH)(R$^{25}$), —CH$_2$NR$^{25}$C(NR$^{25a}$R$^{25b}$)=CH(NO$_2$), alkyl, alkenyl, alkynyl, cycloalkyl, heteroaryl, or heterocycloalkyl; where the alkyl, alkenyl, alkynyl, cycloalkyl, heteroaryl, and heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, —OR$^8$, —NR$^8$R$^{8'}$, —NR$^8$S(O)$_2$R$^9$, —CN, —S(O)$_m$R$^9$, —C(O)R$^8$, —C(O)OR$^8$, —C(O)NR$^8$R$^{8'}$, —NR$^8$C(O)NR$^8$R$^{8''}$, —NR$^8$C(O)OR$^{8'}$ and —NR$^8$C(O)R$^{8'}$; or one of R$^1$ and R$^2$ together with the carbon to which they are attached, R$^3$ and R$^4$ together with the carbon to which they are attached, and R$^5$ and R$^6$ together with the carbon to which they are attached form C(O) or C(=NOH);

m is 0, 1, or 2;

R$^7$ is hydrogen, halo or alkyl;

each R$^8$, R$^{8'}$ and R$^{8''}$ is independently selected from hydrogen, hydroxy, optionally substituted alkoxy, alkyl, alkenyl, alkynyl, aryl, cycloalkyl, heteroaryl, and heterocycloalkyl; where the alkyl, alkenyl, alkynyl, aryl, cycloalkyl, heteroaryl, and heterocycloalkyl are independently optionally substituted with one, two three, four, or five groups independently selected from alkyl, halo, hydroxy, hydroxyalkyl, optionally substituted alkoxy, alkoxyalkyl, haloalkyl, carboxy, alkoxycarbonyl, alkenyloxycarbonyl, optionally substituted cycloalkyl, optionally substituted cycloalkyloxycarbonyl, optionally substituted aryl, optionally substituted aryloxy, optionally substituted aryloxycarbonyl, optionally substituted arylalkyl, optionally substituted arylalkyloxy, optionally substituted arylalkyloxycarbonyl, nitro, cyano, optionally substituted heterocycloalkyl, optionally substituted heteroaryl, —S(O)R$^{31}$ (where n is 0, 1, or 2 and R$^{31}$ is optionally substituted alkyl, optionally substituted aryl, optionally substituted heterocycloalkyl, or optionally substituted heteroaryl), —NR$^{34}$SO$_2$R$^{34a}$ (where R$^{34}$ is hydrogen or alkyl and R$^{34a}$ is alkyl, alkenyl, cycloalkyl, aryl, heteroaryl, or heterocycloalkyl), —SO$_2$NR$^{35}$R$^{35a}$ (where R$^{35}$ is hydrogen or alkyl and R$^{35a}$ is alkyl, alkenyl, cycloalkyl, aryl, heteroaryl, or heterocycloalkyl), —NR$^{32}$C(O)R$^{32a}$ (where R$^{32}$ is hydrogen or alkyl and R$^{32a}$ is alkyl, alkenyl, alkoxy, or cycloalkyl), —NR$^{30}$R$^{30'}$ (where R$^{30}$ and R$^{30'}$ are independently hydrogen, alkyl, or hydroxyalkyl), and —C(O)NR$^{33}$R$^{33a}$ (where R$^{33}$ is hydrogen or alkyl and R$^{33a}$ is alkyl, alkenyl, alkynyl, or cycloalkyl); and each R$^9$ is independently selected from alkyl, alkenyl, alkynyl, aryl, cycloalkyl, heteroaryl, and heterocycloalkyl; where the alkyl, alkenyl, alkynyl, aryl, cycloalkyl, heteroaryl, and heterocycloalkyl are independently optionally substituted with one, two, three, four, or five groups selected from halo, hydroxy, alkyl, haloalkyl, haloalkoxy, amino, alkylamino, and dialkylamino;

Group B:

A is heteroarylene optionally substituted with one, two, three, or four groups selected from R$^{10}$, R$^{12}$, R$^{14}$, R$^{16}$ and R$^{19}$ where R$^{10}$, R$^{12}$, R$^{14}$ and R$^{16}$ are independently hydrogen, alkyl, alkenyl, alkynyl, halo, haloalkoxy, hydroxy, alkoxy, cyano, amino, alkylamino, dialkylamino, haloalkyl, alkylsulfonylamino, alkylcarbonyl, alkenylcarbonyl, alkoxycarbonyl, alkenyloxycarbonyl, aminocarbonyl, alkylaminocarbonyl, dialkylaminocarbonyl, or alkylcarbonylamino; where R$^{19}$ is hydrogen, alkyl, or alkenyl; and where each alkyl and alkenyl, either alone or as part of another group within R$^{10}$, R$^{12}$, R$^{14}$, R$^{16}$, and R$^{19}$, is independently optionally substituted with halo, hydroxy, or alkoxy;

X is alkyl, halo, haloalkyl, or haloalkoxy;

R$^1$, R$^2$, R$^3$, R$^4$, R$^5$ and R$^6$ are independently hydrogen, halo, nitro, —NR$^8$R$^{8'}$, —OR$^8$, —NHS(O)$_2$R$^8$, —CN, —S(O)$_m$R$^8$, —S(O)$_2$NR$^8$R$^{8'}$, —C(O)R$^8$, —C(O)OR$^8$, —C(O)NR$^8$R$^{8'}$, —NR$^8$C(O)OR$^{8'}$, —NR$^8$C(O)NR$^8$R$^{8''}$, —NR$^8$C(O)OR$^{8'}$, —NR$^8$C(O)R$^{8'}$, —CH$_2$N(R$^{25}$)(NR$^{25a}$R$^{25b}$), —CH$_2$NR$^{25}$C(=NH)(NR$^{25a}$R$^{25b}$), —CH$_2$NR$^{25}$C(=NH)(N(R$^{25a}$)(NO$_2$)), —CH$_2$NR$^{25}$C(NH)(N(R$^{25a}$)(CN)), —CH$_2$NR$^{25}$C(=NH)(R$^{25}$), —CH$_2$NR$^{25}$C(NR$^{25a}$R$^{25b}$)=CH(NO$_2$), alkyl, alkenyl, alkynyl, cycloalkyl, heteroaryl, or heterocycloalkyl, where the alkyl, alkenyl, alkynyl, cycloalkyl, heteroaryl, and heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, —OR$^8$, —NR$^8$R$^{8'}$, —NR$^8$S(O)$_2$R$^9$, —CN, —S(O)$_m$R$^9$, —C(O)R$^8$, —C(O)OR$^8$, —C(O)NR$^8$R$^{8'}$, —NR$^8$C(O)NR$^8$R$^{8''}$, —NR$^8$C(O)OR$^{8'}$ and —NR$^8$C(O)R$^{8'}$; or one of R$^1$ and R$^2$ together with the carbon to which they are attached, R$^3$ and R$^4$ together with the carbon to which they are attached, and R$^5$ and R$^6$ together with the carbon to which they are attached form C(O) or C(=NOH);

m is 1 or 2;

R$^7$ is hydrogen, halo or alkyl; and each R$^8$, R$^{8'}$ and R$^{8'}$ is independently selected from hydrogen, hydroxy, optionally substituted alkoxy, alkyl, haloalkyl, alkenyl, alkynyl, aryl, cycloalkyl, heteroaryl, and heterocycloalkyl, where the alkyl, alkenyl, alkynyl, aryl, cycloalkyl, heteroaryl, and heterocycloalkyl are independently optionally substituted with one, two three, four, or five groups independently selected from alkyl, halo, hydroxy, hydroxyalkyl, optionally substituted alkoxy, alkoxyalkyl, haloalkyl, carboxy, carboxy ester, nitro, cyano, —S(O)$_n$R$^{31}$ (where n is 0, 1, or 2 and R$^{31}$ is optionally substituted alkyl, optionally substituted aryl, optionally substituted cycloalkyl, optionally substituted heterocycloalkyl, or optionally substituted heteroaryl), —NR$^{36}$S(O)$_2$R$^{36a}$ (where R$^{36}$ is hydrogen, alkyl, or alkenyl and R$^{36a}$ is alkyl, alkenyl, optionally substituted aryl, optionally substituted cycloalkyl, optionally substituted heterocycloalkyl, or optionally substituted heteroaryl), —S(O)$_2$NR$^{37}$R$^{37a}$ (where R$^{37}$ is hydrogen, alkyl, or alkenyl and R$^{37a}$ is alkyl, alkenyl, optionally substituted aryl, optionally substituted cycloalkyl, optionally substituted heterocycloalkyl, or optionally substituted heteroaryl), optionally substituted cycloalkyl, optionally substituted heterocycloalkyl, optionally substituted aryl, optionally substituted arylalkyl, optionally substituted aryloxy, optionally substituted arylalkyloxy, optionally substituted heteroaryl, —NHC(O)R$^{32}$ (where R$^{32}$ is alkyl, alkenyl, alkoxy, or cycloalkyl) and —NR$^{30}$R$^{30'}$ (where R$^{30}$ and R$^{30'}$ are independently hydrogen, alkyl, or hydroxyalkyl), and —C(O)NHR$^{33}$ (where R$^{33}$ is alkyl, alkenyl, alkynyl, or cycloalkyl);

Group C:

A is

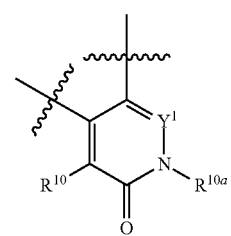

(a)

45 where $R^{10}$ is hydrogen, alkyl, alkenyl, alkynyl, halo, haloalkoxy, hydroxy, alkoxy, amino, alkylamino, dialkylamino, haloalkyl, —NHS(O)$_2$R$^8$, —CN, —C(O)R$^8$, —C(O)OR$^8$, —C(O)NR$^8$R$^{8'}$ and —NR$^8$C(O)R$^{8'}$;

$R^{10a}$ is hydrogen, alkyl, or alkenyl;

$Y^1$ is =CH— or =N—;

X is alkyl, halo, haloalkyl, or haloalkoxy;

$R^1$, $R^2$, $R^3$, $R^4$, $R^5$ and $R^6$ are independently hydrogen, halo, nitro, —NR$^8$R$^{8'}$, —OR$^8$, —NHS(O)$_2$R$^8$, —CN, —S(O)$_m$R$^8$, —S(O)$_2$NR$^8$R$^{8'}$, —C(O)R$^8$, —C(O)OR$^8$, —C(O)NR$^8$R$^{8'}$, —NR$^8$C(O)OR$^{8'}$, —NR$^8$C(O)NR$^8$R$^{8''}$, —NR$^8$C(O)OR$^{8'}$, —NR$^8$C(O)R$^{8'}$, —CH$_2$N(R$^{25}$)NR$^{25a}$R$^{25b}$), —CH$_2$NR$^{25}$C(=NH)(NR$^{25a}$R$^{25b}$), —CH$_2$NR$^{25}$C(=NH)(N(R$^{25a}$)(NO$_2$)), —CH$_2$NR$^{25}$C(=NH)(N(R$^{25a}$)(CN)), —CH$_2$NR$^{25}$C(=NH)(R$^{25}$), —CH$_2$NR$^{25}$C(NR$^{25a}$R$^{25b}$)=CH(NO$_2$), alkyl, alkenyl, alkynyl, cycloalkyl, heteroaryl, or heterocycloalkyl, where the alkyl, alkenyl, alkynyl, cycloalkyl, heteroaryl, and heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, —OR$^8$, —NR$^8$R$^{8'}$, —NR$^8$S(O)$_2$R$^9$, —CN, —S(O)$_m$R$^9$, —C(O)R$^8$, —C(O)OR$^8$, —C(O)NR$^8$R$^{8'}$, —NR$^8$C(O)NR$^8$R$^{8''}$, —NR$^8$C(O)OR$^{8'}$ and —NR$^8$C(O)R$^{8'}$; or one of $R^1$ and $R^2$ together with the carbon to which they are attached, $R^3$ and $R^4$ together with the carbon to which they are attached, and $R^5$ and $R^6$ together with the carbon to which they are attached form C(O) or C(NOH);

m is 1 or 2;

$R^7$ is hydrogen, halo or alkyl; and each $R^8$, $R^{8'}$ and $R^{8''}$ is independently selected from hydrogen, hydroxy, optionally substituted alkoxy, alkyl, haloalkyl, alkenyl, alkynyl, aryl, cycloalkyl, heteroaryl, and heterocycloalkyl, where the alkyl, alkenyl, alkynyl, aryl, cycloalkyl, heteroaryl, and heterocycloalkyl are independently optionally substituted with one, two three, four, or five groups independently selected from alkyl, halo, hydroxy, hydroxyalkyl, optionally substituted alkoxy, alkoxyalkyl, haloalkyl, carboxy, carboxy ester, nitro, cyano, —S(O)$_n$R$^{31}$ (where n is 0, 1, or 2 and $R^{31}$ is optionally substituted alkyl, optionally substituted aryl, optionally substituted cycloalkyl, optionally substituted heterocycloalkyl, or optionally substituted heteroaryl), —NR$^{36}$S(O)$_2$R$^{36a}$ (where $R^{36}$ is hydrogen, alkyl, or alkenyl and $R^{36a}$ is alkyl, alkenyl, optionally substituted aryl, optionally substituted cycloalkyl, optionally substituted heterocycloalkyl, or optionally substituted heteroaryl), —S(O)$_2$NR$^{37}$R$^{37a}$ (where $R^{37}$ is hydrogen, alkyl, or alkenyl and $R^{37a}$ is alkyl, alkenyl, optionally substituted aryl, optionally substituted cycloalkyl, optionally substituted heterocycloalkyl, or optionally substituted heteroaryl), optionally substituted cycloalkyl, optionally substituted heterocycloalkyl, optionally substituted aryl, optionally substituted arylalkyl, optionally substituted aryloxy, optionally substituted arylalkyloxy, optionally substituted heteroaryl, —NHC(O)R$^{32}$ (where $R^{32}$ is alkyl, alkenyl, alkoxy, or cycloalkyl) and —NR$^{30}$R$^{30'}$ (where $R^{30}$ and $R^{30'}$ are independently hydrogen, alkyl, or hydroxyalkyl), and —C(O)NHR$^{33}$ (where $R^{33}$ is alkyl, alkenyl, alkynyl, or cycloalkyl); or

46

Group D:

A is

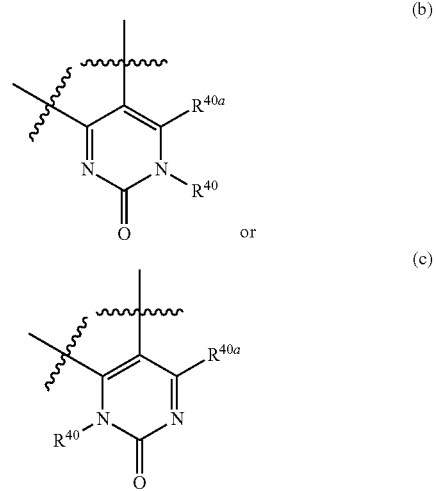

$R^{40}$ and $R^{40a}$ are independently hydrogen or alkyl;

X is alkyl, halo, haloalkyl, or haloalkoxy;

$R^1$, $R^2$, $R^3$, $R^4$, $R^5$ and $R^6$ are independently hydrogen, halo, nitro, —NR$^8$R$^{8'}$, —OR$^8$, —NHS(O)$_2$R$^8$, —CN, —S(O)$_m$R$^8$, —S(O)$_2$NR$^8$R$^{8'}$, —C(O)R$^8$, —C(O)OR$^8$, —C(O)NR$^8$R$^{8'}$, —NR$^8$C(O)OR$^{8'}$, —NR$^8$C(O)NR$^8$R$^{8''}$, —NR$^8$C(O)OR$^{8'}$, —NR$^8$C(O)R$^{8'}$, —CH$_2$N(R$^{25}$)(NR$^{25a}$R$^{25b}$), —CH$_2$NR$^8$C(=NH)(NR$^{25a}$R$^{25b}$), —CH$_2$NR$^{25}$C(=NH)(N(R$^{25a}$)(NO$_2$)), —CH$_2$NR$^{25}$C(=NH)(N(R$^{25a}$)(CN)), —CH$_2$NR$^{25}$C(=NH)(R$^{25}$), —CH$_2$NR$^{25}$C(NR$^{25a}$R$^{25b}$)=CH(NO$_2$), alkyl, alkenyl, alkynyl, cycloalkyl, heteroaryl, or heterocycloalkyl, where the alkyl, alkenyl, alkynyl, cycloalkyl, heteroaryl, and heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, —OR$^8$, —NR$^8$R$^{8'}$, —NR$^8$S(O)$_2$R$^9$, —CN, —S(O)$_m$R$^9$, —C(O)R$^8$, —C(O)OR$^8$, —C(O)NR$^8$R$^{8'}$, —NR$^8$C(O)NR$^8$R$^{8''}$, —NR$^8$C(O)OR$^{8'}$ and —NR$^8$C(O)R$^{8'}$; or one of $R^1$ and $R^2$ together with the carbon to which they are attached, $R^3$ and $R^4$ together with the carbon to which they are attached, and $R^5$ and $R^6$ together with the carbon to which they are attached form C(O) or C(NOH);

m is 1 or 2;

$R^7$ is hydrogen, halo or alkyl; and $R^8$, $R^{8'}$ and $R^{8''}$ are independently selected from hydrogen, hydroxy, optionally substituted alkoxy, alkyl, haloalkyl, alkenyl, alkynyl, aryl, cycloalkyl, heteroaryl, and heterocycloalkyl, where the alkyl, alkenyl, alkynyl, aryl, cycloalkyl, heteroaryl, and heterocycloalkyl are independently optionally substituted with one, two three, four, or five groups independently selected from alkyl, halo, hydroxy, hydroxyalkyl, optionally substituted alkoxy, alkoxyalkyl, haloalkyl, carboxy, carboxy ester, nitro, cyano, —S(O)$_n$R$^{31}$ (where n is 0, 1, or 2 and $R^{31}$ is optionally substituted alkyl, optionally substituted aryl, optionally substituted cycloalkyl, optionally substituted heterocycloalkyl, or optionally substituted heteroaryl), —NR$^{36}$S(O)$_2$R$^{36a}$ (where R$^{36}$ is hydrogen, alkyl, or alkenyl and R$^{36a}$ is alkyl, alkenyl, optionally substituted aryl, optionally substituted cycloalkyl, optionally substituted heterocycloalkyl, or optionally substituted heteroaryl), —S(O)$_2$NR$^{37}$R$^{37a}$ (where R$^{37}$ is hydrogen, alkyl, or alkenyl and R$^{37a}$ is alkyl, alkenyl, optionally substituted aryl, optionally substituted cycloalkyl, optionally substituted heterocycloalkyl, or optionally substituted heteroaryl), optionally substituted cycloalkyl, optionally substituted heterocycloalkyl, optionally substituted aryl, optionally substituted arylalkyl, optionally substituted aryloxy, optionally substituted arylalkyloxy, optionally substituted heteroaryl, —NHC(O)R$^{32}$ (where R$^{32}$ is alkyl, alkenyl, alkoxy, or cycloalkyl) and —NR$^{30}$R$^{30'}$ (where R$^{30}$ and R$^{30'}$ are independently hydrogen, alkyl, or hydroxyalkyl), and —C(O)NHR$^{33}$ (where R$^{33}$ is alkyl, alkenyl, alkynyl, or cycloalkyl).

In some variations, the MEK inhibitor compound of the formula (I) is a compound of the Group A, having the formula I(a) or I(b):

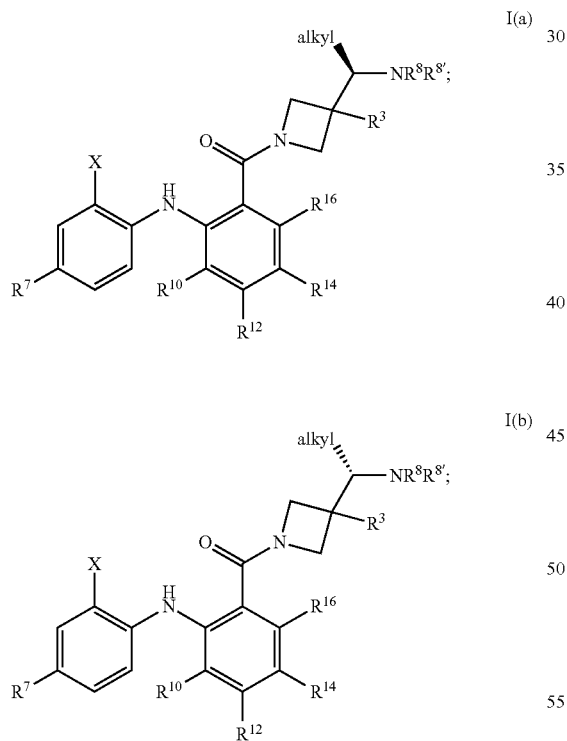

or a pharmaceutically acceptable salt or solvate thereof, wherein the variables are as defined for the formula (I), Group A, or as defined in WO 2007/044515 A1, incorporated herein by reference.

In some variations, the MEK inhibitor compound of the formula (I) is a compound of the Group B, having the formula I(c), I(d), I(e), I(f), I(g), I(h), I(i), I(j), I(k), I(m), I(n), I(o), I(p), I(q), I(r), I(s), I(u), I(v), I(w), I(x), I(cc) or I(dd):

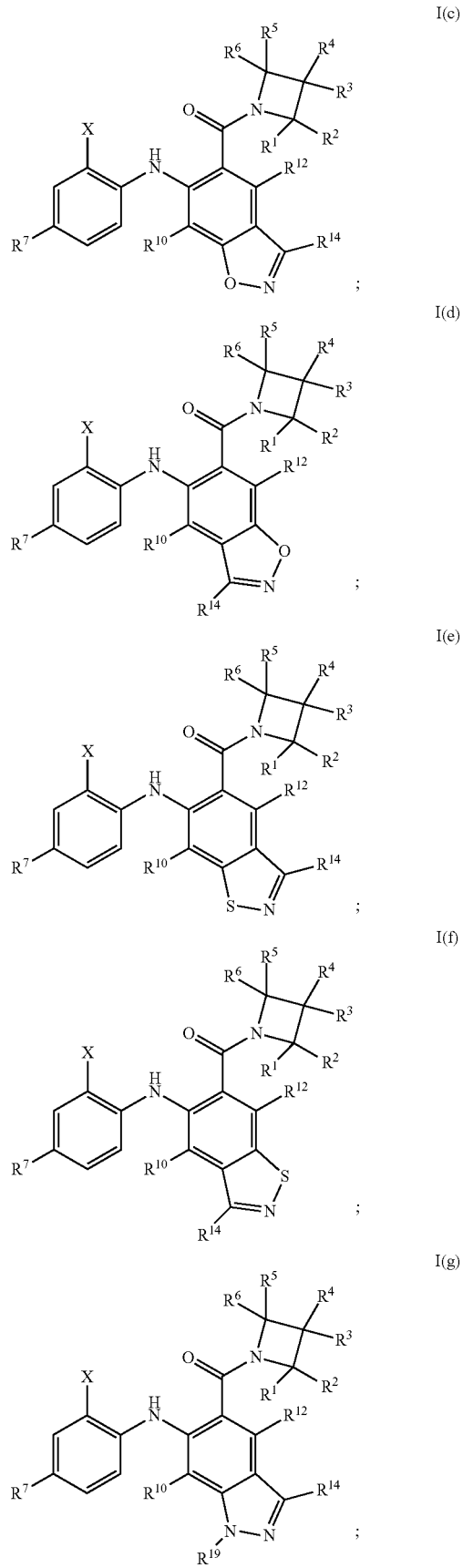

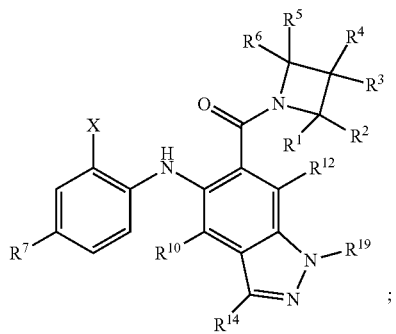
I(h)
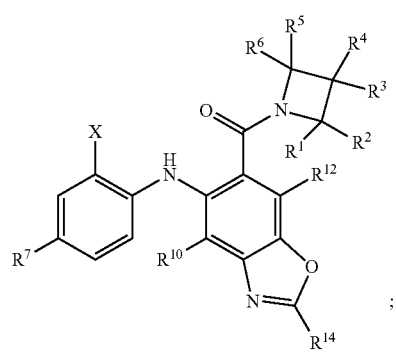
I(i)
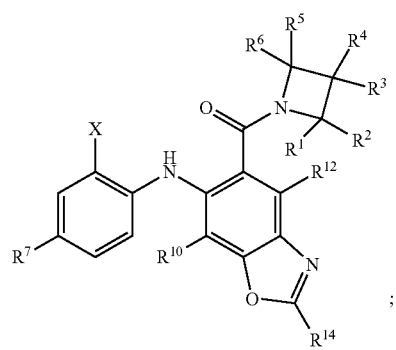
I(j)
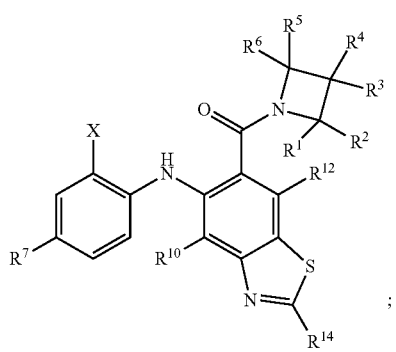
I(k)
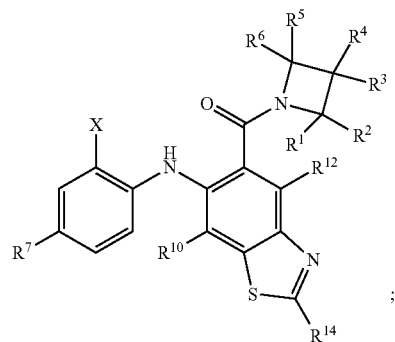
I(m)
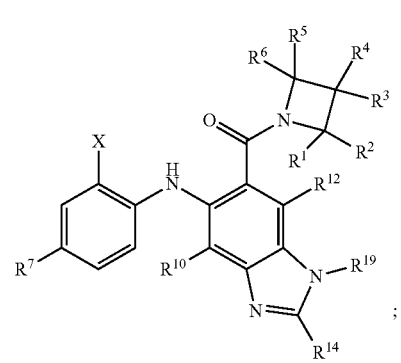
I(n)
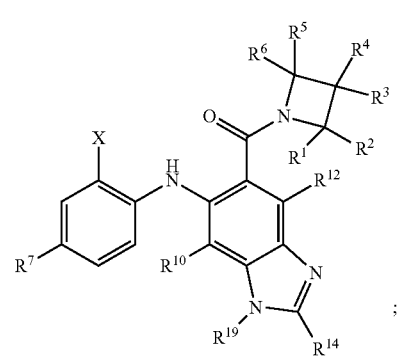
I(o)
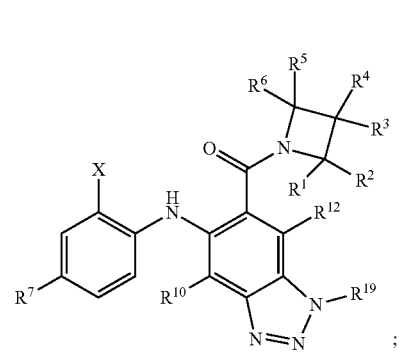
I(p)

I(q)
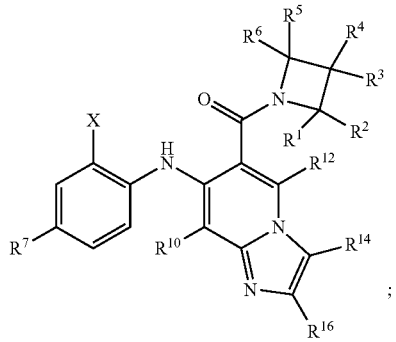
I(r)
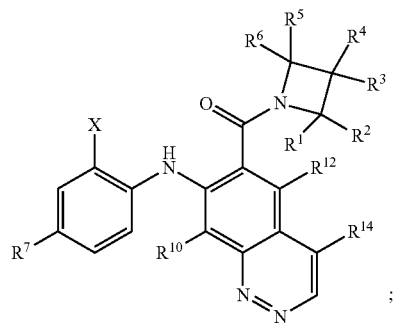
I(s)
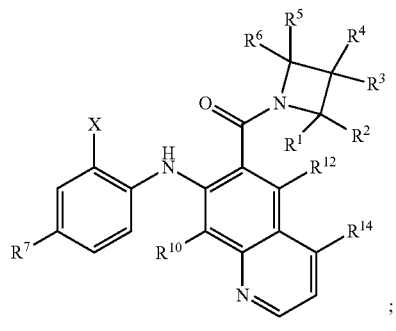
I(u)
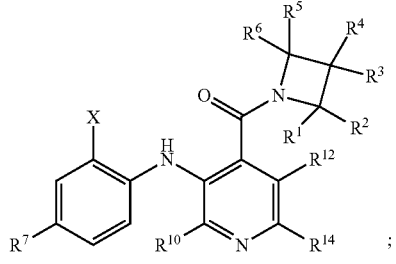
I(v)
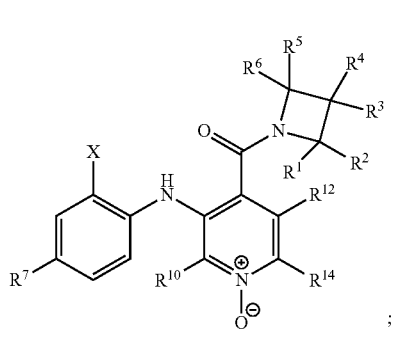
I(w)
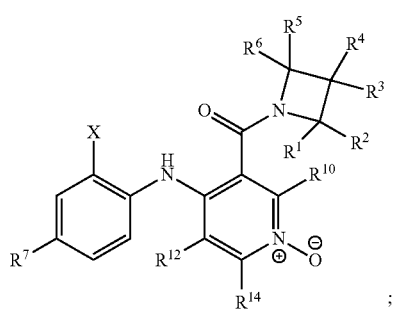
I(x)
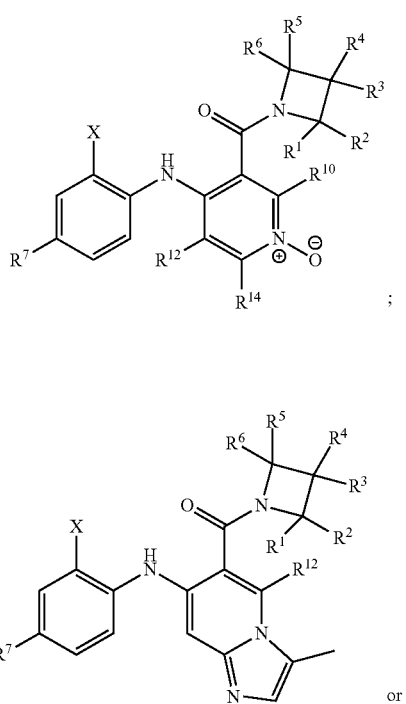
I(cc)
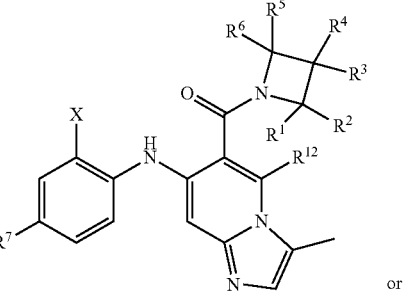
or
I(dd)
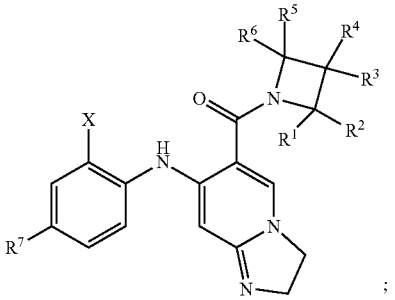
or a pharmaceutically acceptable salt or solvate thereof, wherein the variables are as defined for the formula (I), Group B, or as defined in WO 2007/044515 A1, incorporated herein by reference.
In some variations, the MEK inhibitor compound of the formula (I) is a compound of the Group C, having the formula I(y) or I(z):

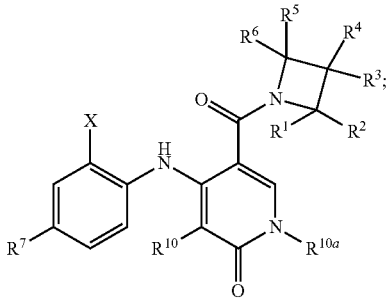

I(y)

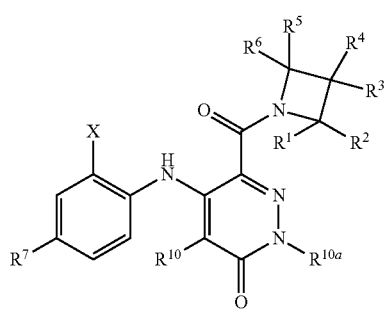

I(z)

or a pharmaceutically acceptable salt or solvate thereof, wherein the variables are as defined for the formula (I), Group C, or as defined in WO 2007/044515 A1, incorporated herein by reference.

In some variations, the MEK inhibitor compound of the formula (I) is a compound of the Group D, having the formula I(aa) or I(bb):

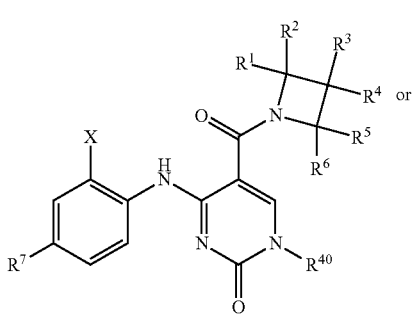

I(aa)

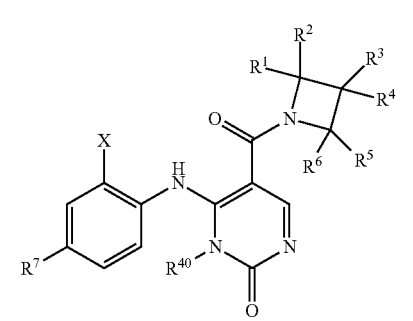

I(bb)

or a pharmaceutically acceptable salt or solvate thereof, wherein the variables are as defined for the formula (I), Group D, or as defined in WO 2007/044515 A1, incorporated herein by reference.

In some embodiments, the MEK inhibitor compound of the formula (I) is a compound selected from the compound Nos. 1-362 as listed in WO 2007/044515 A1, Table 1 on pages 71-144 (herein collectively referred to as the Formula I Species), or a pharmaceutically acceptable salt or solvate thereof.

Also embraced are any variations of formula (I) as described in WO 2007/044515 A1, which is incorporated herein by reference. Compounds of the formula (I) or any variations thereof can be synthesized using methods known in the art, for example, the synthetic methods described in WO 2007/044515 A1, incorporated herein by reference.

Unless defined otherwise herein, the terms used in describing compounds of the formula (I) should be understood to have the same meaning as defined in WO 2007/044515 A1.

In some embodiments, the MEK inhibitor is a compound of formula (II):

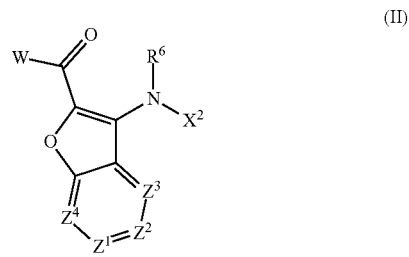

(II)

or a pharmaceutically acceptable salt or solvate thereof, wherein:

$Z^1$ is $CR^1$ or N;
$Z^2$ is $CR^2$ or N;
$Z^3$ is $CR^3$ or N;
$Z^4$ is $CR^4$ or N;
where one or two of $Z^1$, $Z^2$, $Z^3$, and $Z^4$ are N;
$R^1$, $R^2$, $R^3$ and $R^4$ are independently selected from H, halo, CN, $CF_3$, $-OCF_3$, $-NO_2$, $-(CR^{14}R^{15})_nC(=Y)R^{11}$, $-(CR^{14}R^{15})_nC(=Y)OR^{11}$, $-(CR^{14}R^{15})_nC(=Y)NR^{11}R^{12}$, $-(CR^{14}R^{15})_nNR^{11}R^{12}$, $-(CR^{14}R^{15})_nOR^1$, $-(CR^{14}R^{15})_nSR^{11}$, $-(CR^{14}R^{15})_nNR^{12}C(=Y)R^{11}$, $-(CR^{14}R^{15})_nNR^{12}C(=Y)OR^{11}$, $-(CR^{14}R^{15})_nNR^{13}C(=Y)NR^{11}R^{12}$, $-(CR^{14}R^{15})_nNR^{12}SO_2R^{11}$, $-(CR^{14}R^{15})_nOC(=Y)R^{11}$, $-(CR^{14}R^{15})_nOC(=Y)OR^{11}$, $-(CR^{14}R^{15})_nOC(=Y)NR^{11}R^{12}$, $-(CR^{14}R^{15})_nOS(O)_2OR^{11}$, $-(CR^{14}R^{15})_nOP(=Y)(OR^{11})(OR^{12})$, $-(CR^{14}R^{15})_nOP(OR^{11})(OR^{12})$, $-(CR^{14}R^{15})_nS(O)R^{11}$, $-(CR^{14}R^{15})_nS(O)_2R^{11}$, $-(CR^{14}R^{15})_nS(O)_2NR^{11}R^{12}$, $-(CR^{14}R^{15})_nS(O)(OR^{11})$, $-(CR^{14}R^{15})_nS(O)_2(OR^{11})$, $-(CR^{14}R^{15})_nSC(=Y)R^{11}$, $-(CR^{14}R^{15})_nSC(=Y)OR^{11}$, $-(CR^{14}R^{15})_nSC(=Y)NR^{11}R^{12}$, $C_1$-$C_{12}$ alkyl, $C_2$-$C_8$ alkenyl, $C_2$-$C_8$ alkynyl, carbocyclyl, heterocyclyl, aryl, and heteroaryl;
W is

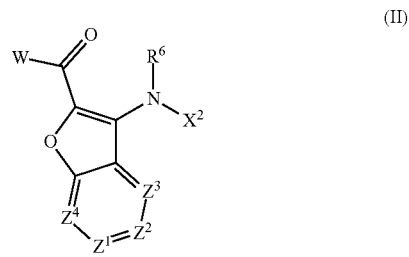

$R^5$ and $R^6$ are independently selected from H or $C_1$-$C_{12}$ alkyl;
$X^1$ is selected from $R^{11}$, $-OR^{11}$, $-NR^{11}R^{12}$, $-S(O)R^{11}$, and $-S(O)_2R^{11}$; when $X^1$ is $R^{11}$ or $-OR^{11}$, $R^{11}$ or $-OR^{11}$ of $X^1$ and $-R^5$ are optionally taken together with the nitrogen atom to which they are attached to form a 4-7 membered saturated or unsaturated ring having 0-2 additional heteroatoms selected from O, S and N, wherein said ring is optionally substituted with one or more groups selected from halo, CN, $CF_3$, $-OCF_3$, $-NO_2$, oxo, $-Si(C_1-C_6$ alkyl), $-(CR^{19}R^{20})_nC(=Y')R^{16}$, $-(CR^{19}R^{20})_nC(=Y')OR^{16}$, $-(CR^{19}R^{20})_nC(=Y')NR^{16}R^{17}$, $-(CR^{19}R^{20})_nNR^{16}R^{17}$, $-(CR^{19}R^{20})_nOR^{16}$, $-(CR^{19}R^{20})_n-SR^{16}$, $-(CR^{19}R^{20})_nNR^{16}C(=Y')R^{17}$, $-(CR^{19}R^{20})_nNR^{16}C(=Y')OR^{17}$, $-(CR^{19}R^{20})_nNR^{18}C(=Y')NR^{16}R^{17}$, $-(CR^{19}R^{20})_nNR^{17}SO_2R^{16}$, $-(CR^{19}R^{20})_nOC(=Y')R^{16}$, $-(CR^{19}R^{20})_nOC(=Y')OR^{16}$, $-(CR^{19}R^{20})_nOC(=Y')NR^{16}R^{17}$, $-(CR^{19}R^{20})_nOS(O)_2(OR^{16})$, $-(CR^{19}R^{20})_nOP(=Y')(OR^{16})(OR^{17})$, $-(CR^{19}R^{20})_nOP(OR^{16})(OR^{17})$, $-(CR^{19}R^{20})_nS(O)R^{16}$, $-(CR^{19}R^{20})_nS(O)_2R^{16}$, $-(CR^{19}R^{20})_nS(O)_2NR^{16}R^{17}$, $-(CR^{19}R^{20})_nS(O)(OR^{16})$, $-(CR^{19}R^{20})_nS(O)_2(OR^{16})$, $-(CR^{19}R^{20})_nSC(=Y')R^{16}$, $-(CR^{19}R^{20})_nSC(=Y')OR^{16}$, $-(CR^{19}R^{20})_nSC(=Y')NR^{16}R^{17}$, and $R^{21}$;

$X^2$ is selected from carbocyclyl, heterocyclyl, aryl, and heteroaryl;

$R^{11}$, $R^{12}$ and $R^{13}$ are independently H, $C_1-C_{12}$ alkyl, $C_2-C_8$ alkenyl, $C_2-C_8$ alkynyl, carbocyclyl, heterocyclyl, aryl, or heteroaryl, or $R^{11}$ and $R^{12}$ together with the nitrogen to which they are attached form a 3-8 membered saturated, unsaturated or aromatic ring having 0-2 heteroatoms selected from O, S and N, wherein said ring is optionally substituted with one or more groups selected from halo, CN, $CF_3$, $-OCF_3$, $-NO_2$, $C_1-C_6$ alkyl, $-OH$, $-SH$, $-O(C_1-C_6$ alkyl), $-S(C_1-C_6$ alkyl), $-NH_2$, $-NH(C_1-C_6$ alkyl), $-N(C_1-C_6$ alkyl)$_2$, $-SO_2(C_1-C_6$ alkyl), $-CO_2H$, $-CO_2(C_1-C_6$ alkyl), $-C(O)NH_2$, $-C(O)NH(C_1-C_6$ alkyl), $-C(O)N(C_1-C_6$ alkyl)$_2$, $-N(C_1-C_6$ alkyl)$C(O)(C_1-C_6$ alkyl), $-NHC(O)(C_1-C_6$ alkyl), $-NHSO_2(C_1-C_6$ alkyl), $-N(C_1-C_6$ alkyl)$SO_2(C_1-C_6$ alkyl), $-SO_2NH_2$, $-SO_2NH(C_1-C_6$ alkyl), $-SO_2N(C_1-C_6$ alkyl)$_2$, $-OC(O)NH_2$, $-OC(O)NH(C_1-C_6$ alkyl), $-OC(O)N(C_1-C_6$ alkyl)$_2$, $-OC(O)O(C_1-C_6$ alkyl), $-NHC(O)NH(C_1-C_6$ alkyl), $-NHC(O)N(C_1-C_6$ alkyl)$_2$, $-N(C_1-C_6$ alkyl)$C(O)NH(C_1-C_6$ alkyl), $-N(C_1-C_6$ alkyl)$C(O)N(C_1-C_6$ alkyl)$_2$, $-NHC(O)NH(C_1-C_6$ alkyl), $-NHC(O)N(C_1-C_6$ alkyl)$_2$, $-NHC(O)O(C_1-C_6$ alkyl), and $-N(C_1-C_6$ alkyl)$C(O)O(C_1-C_6$ alkyl);

$R^{14}$ and $R^{15}$ are independently selected from H, $C_1-C_{12}$ alkyl, aryl, carbocyclyl, heterocyclyl, and heteroaryl;

m and n are independently selected from 0, 1, 2, 3, 4, 5, or 6;

Y is independently O, $NR^{11}$, or S;

wherein each said alkyl, alkenyl, alkynyl, carbocyclyl, heterocyclyl, aryl and heteroaryl of $R^1$, $R^2$, $R^3$, $R^4$, $R^5$, $R^6$, $X^2$, $R^{11}$, $R^{12}$, $R^{13}$, $R^{14}$, and $R^{15}$ is independently optionally substituted with one or more groups independently selected from halo, CN, $CF_3$, $-OCF_3$, $-NO_2$, oxo, $-Si(C_1-C_6$ alkyl), $-(CR^{19}R^{20})_nC(=Y')R^{16}$, $-(CR^{19}R^{20})_nC(=Y')OR^{16}$, $-(CR^{19}R^{20})_nC(=Y')NR^{16}R^{17}$, $-(CR^{19}R^{20})_nNR^{16}R^{17}$, $-(CR^{19}R^{20})_nOR^{16}$, $-(CR^{19}R^{20})_n-SR^{16}$, $-(CR^{19}R^{20})_nNR^{16}C(=Y')R^{17}$, $-(CR^{19}R^{20})_nNR^{16}C(=Y')OR^{17}$, $-(CR^{19}R^{20})_nNR^{18}C(=Y')NR^{16}R^{17}$, $-(CR^{19}R^{20})_nNR^{17}SO_2R^{16}$, $-(CR^{19}R^{20})_nOC(=Y')R^{16}$, $-(CR^{19}R^{20})_nOC(=Y')OR^{16}$, $-(CR^{19}R^{20})_nOC(=Y')NR^{16}R^{17}$, $-(CR^{19}R^{20})_nOS(O)_2(OR^{16})$, $-(CR^{19}R^{20})_nOP(=Y')(OR^{16})(OR^{17})$, $-(CR^{19}R^{20})_nOP(OR^{16})(OR^{17})$, $-(CR^{19}R^{20})_nS(O)R^{16}$, $-(CR^{19}R^{20})_nS(O)_2R^{16}$, $-(CR^{19}R^{20})_nS(O)_2NR^{16}R^{17}$, $-(CR^{19}R^{20})_nS(O)(OR^{16})$, $-(CR^{19}R^{20})_nS(O)_2(OR^{16})$, $-(CR^{19}R^{20})_nSC(=Y')R^{16}$, $-(CR^{19}R^{20})_nSC(=Y')OR^{16}$, $-(CR^{19}R^{20})_nSC(=Y')NR^{16}R^{17}$, and $R^{21}$;

each $R^{16}$, $R^{17}$ and $R^{18}$ is independently H, $C_1-C_{12}$ alkyl, $C_2-C_8$ alkenyl, $C_2-C_8$ alkynyl, carbocyclyl, heterocyclyl, aryl, or heteroaryl, wherein said alkyl, alkenyl, alkynyl, carbocyclyl, heterocyclyl, aryl, or heteroaryl is optionally substituted with one or more groups selected from halo, oxo, CN, $-OCF_3$, $CF_3$, $-NO_2$, $C_1-C_6$ alkyl, $-OH$, $-SH$, $-O(C_1-C_6$ alkyl), $-S(C_1-C_6$ alkyl), $-NH_2$, $-NH(C_1-C_6$ alkyl), $-N(C_1-C_6$ alkyl)$_2$, $-SO_2(C_1-C_6$ alkyl), $-CO_2H$, $-CO_2(C_1-C_6$ alkyl), $-C(O)NH_2$, $-C(O)NH(C_1-C_6$ alkyl), $-C(O)N(C_1-C_6$ alkyl)$_2$, $-N(C_1-C_6$ alkyl)$C(O)(C_1-C_6$ alkyl), $-NHC(O)(C_1-C_6$ alkyl), $-NHSO_2(C_1-C_6$ alkyl), $-N(C_1-C_6$ alkyl)$SO_2(C_1-C_6$ alkyl), $-SO_2NH_2$, $-SO_2NH(C_1-C_6$ alkyl), $-SO_2N(C_1-C_6$ alkyl)$_2$, $-OC(O)NH_2$, $-OC(O)NH(C_1-C_6$ alkyl), $-OC(O)N(C_1-C_6$ alkyl)$_2$, $-OC(O)O(C_1-C_6$ alkyl), $-NHC(O)NH(C_1-C_6$ alkyl), $-NHC(O)N(C_1-C_6$ alkyl)$_2$, $-N(C_1-C_6$ alkyl)$C(O)NH(C_1-C_6$ alkyl), $-N(C_1-C_6$ alkyl)$C(O)N(C_1-C_6$ alkyl)$_2$, $-NHC(O)NH(C_1-C_6$ alkyl), $-NHC(O)N(C_1-C_6$ alkyl)$_2$, $-NHC(O)O(C_1-C_6$ alkyl), and $-N(C_1-C_6$ alkyl)$C(O)O(C_1-C_6$ alkyl);

or $R^{16}$ and $R^{17}$ together with the nitrogen to which they are attached form a 3-8 membered saturated, unsaturated or aromatic ring having 0-2 heteroatoms selected from O, S and N, wherein said ring is optionally substituted with one or more groups selected from halo, CN, $-OCF_3$, $CF_3$, $-NO_2$, $C_1-C_6$ alkyl, $-OH$, $-SH$, $-O(C_1-C_6$ alkyl), $-S(C_1-C_6$ alkyl), $-NH_2$, $-NH(C_1-C_6$ alkyl), $-N(C_1-C_6$ alkyl)$_2$, $-SO_2(C_1-C_6$ alkyl), $-CO_2H$, $-CO_2(C_1-C_6$ alkyl), $-C(O)NH_2$, $-C(O)NH(C_1-C_6$ alkyl), $-C(O)N(C_1-C_6$ alkyl)$_2$, $-N(C_1-C_6$ alkyl)$C(O)(C_1-C_6$ alkyl), $-NHC(O)(C_1-C_6$ alkyl), $-NHSO_2(C_1-C_6$ alkyl), $-N(C_1-C_6$ alkyl)$SO_2(C_1-C_6$ alkyl), $-SO_2NH_2$, $-SO_2NH(C_1-C_6$ alkyl), $-SO_2N(C_1-C_6$ alkyl)$_2$, $-OC(O)NH_2$, $-OC(O)NH(C_1-C_6$ alkyl), $-OC(O)N(C_1-C_6$ alkyl)$_2$, $-OC(O)O(C_1-C_6$ alkyl), $-NHC(O)NH(C_1-C_6$ alkyl), $-NHC(O)N(C_1-C_6$ alkyl)$_2$, $-N(C_1-C_6$ alkyl)$C(O)NH(C_1-C_6$ alkyl), $-N(C_1-C_6$ alkyl)$C(O)N(C_1-C_6$ alkyl)$_2$, $-NHC(O)NH(C_1-C_6$ alkyl), $-NHC(O)N(C_1-C_6$ alkyl)$_2$, $-NHC(O)O(C_1-C_6$ alkyl), and $-N(C_1-C_6$ alkyl)$C(O)O(C_1-C_6$ alkyl);

$R^{19}$ and $R^{20}$ are independently selected from H, $C_1-C_{12}$ alkyl, $-(CH_2)_n$-aryl, $-(CH_2)_n$-carbocyclyl, $-(CH_2)$-heterocyclyl, and $-(CH_2)$-heteroaryl;

$R^{21}$ is $C_1-C_{12}$ alkyl, $C_2-C_8$ alkenyl, $C_2-C_8$ alkynyl, carbocyclyl, heterocyclyl, aryl, or heteroaryl, wherein each member of $R^{21}$ is optionally substituted with one or more groups selected from halo, CN, $-OCF_3$, $CF_3$, $-NO_2$, $C_1-C_6$ alkyl, $-OH$, $-SH$, $-O(C_1-C_6$ alkyl), $-S(C_1-C_6$ alkyl), $-NH_2$, $-NH(C_1-C_6$ alkyl), $-N(C_1-C_6$ alkyl)$_2$, $-SO_2(C_1-C_6$ alkyl), $-CO_2H$, $-CO_2(C_1-C_6$ alkyl), $-C(O)NH_2$, $-C(O)NH(C_1-C_6$ alkyl), $-C(O)N(C_1-C_6$ alkyl)$_2$, $-N(C_1-C_6$ alkyl)$C(O)(C_1-C_6$ alkyl), $-NHC(O)(C_1-C_6$ alkyl), $-NHSO_2(C_1-C_6$ alkyl), $-N(C_1-C_6$ alkyl)$SO_2(C_1-C_6$ alkyl), $-SO_2NH_2$, $-SO_2NH(C_1-C_6$ alkyl), $-SO_2N(C_1-C_6$ alkyl)$_2$, $-OC(O)NH_2$, $-OC(O)NH(C_1-C_6$ alkyl), $-OC(O)N(C_1-C_6$ alkyl)$_2$, $-OC(O)O(C_1-C_6$ alkyl), $-NHC(O)NH(C_1-C_6$ alkyl), $-NHC(O)N(C_1-C_6$ alkyl)$_2$, $-N(C_1-C_6$ alkyl)$C(O)NH(C_1-C_6$ alkyl), $-N(C_1-C_6$ alkyl)$C(O)N(C_1-C_6$ alkyl)$_2$, $-NHC(O)NH (C$_1$-C$_6$ alkyl), —NHC(O)N(C$_1$-C$_6$ alkyl)$_2$, —NHC(O)O(C$_1$-C$_6$ alkyl), and —N(C$_1$-C$_6$ alkyl)C(O)O(C$_1$-C$_6$ alkyl);

each Y' is independently O, NR$^{22}$, or S; and

R$^{22}$ is H or C$_1$-C$_{12}$ alkyl.

In some variations, the MEK inhibitor compound of the formula (II) is a compound of the formula (II-1-a), (II-1-b), (II-1-c), (II-1-d), (II-1-e), (II-1-f), (II-1-g), (II-1-h), (II-1-i), (II-2-a), (II-2-b), (II-2-c), (II-2-d), (II-2-e), (II-2-f), (II-2-g), (II-2-h), (II-2-i), (II-3-a), (II-3-b), (II-3-c), (II-3-d), (II-3-e), (II-3-f), (II-3-g), (II-3-h), or (II-3-i):

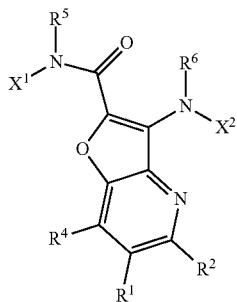

II-1-a

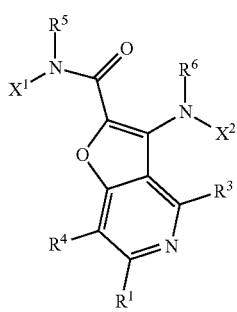

II-1-b

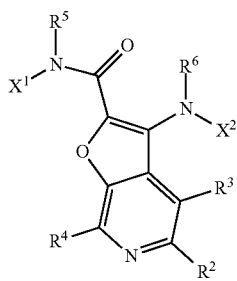

II-1-c

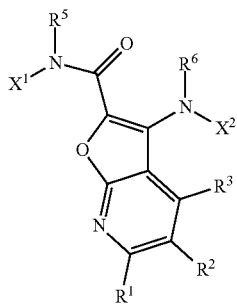

II-1-d

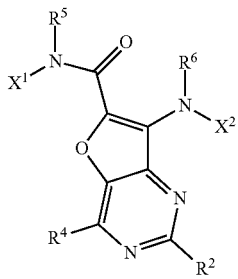

II-1-e

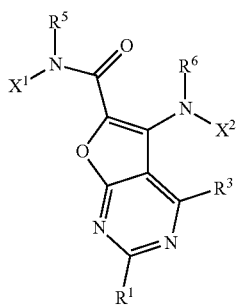

II-1-f

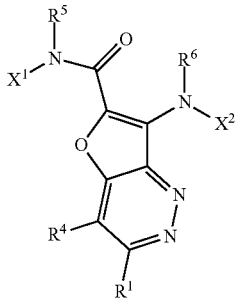

II-1-g

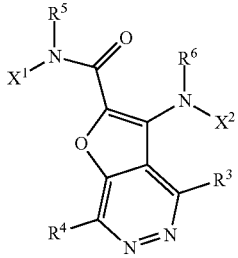

II-1-h

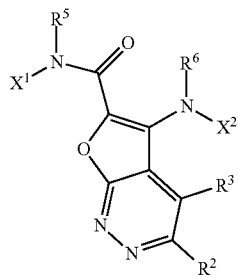

II-1-i

-continued
II-2-a
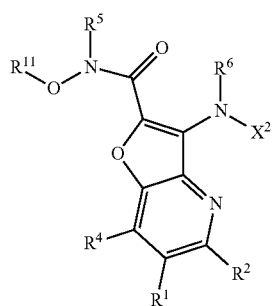
II-2-b
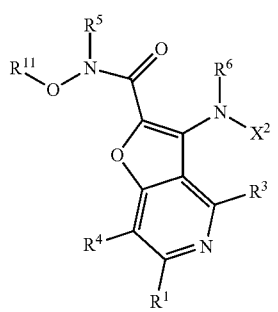
II-2-c
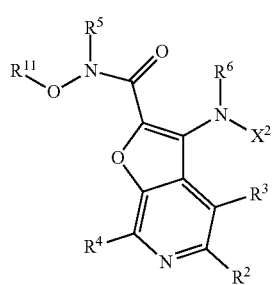
II-2-d
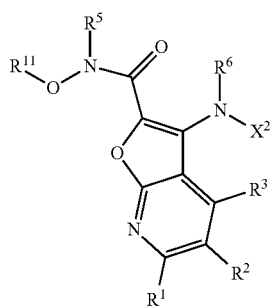
II-2-e
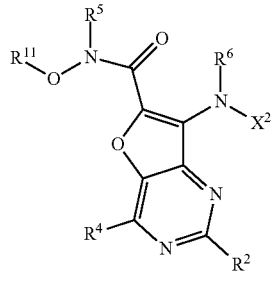
II-2-f
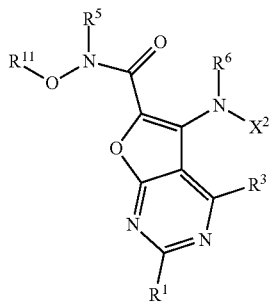
II-2-g
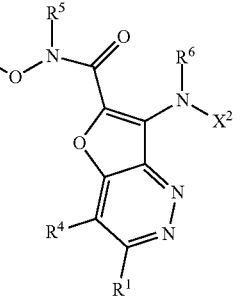
II-2-h
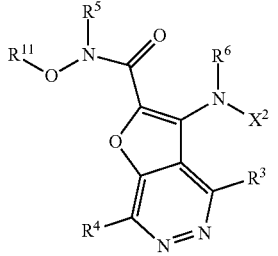
II-2-i
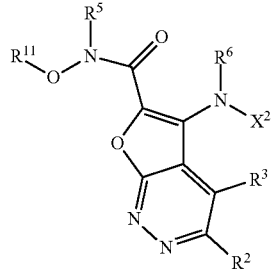
II-3-a
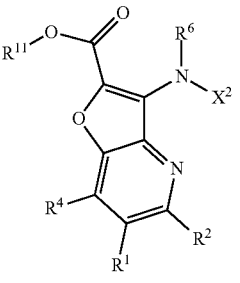

II-3-b
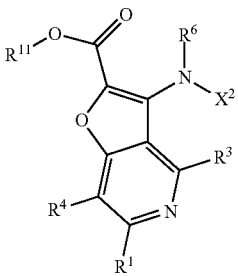

II-3-c
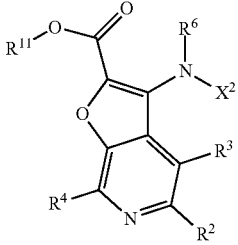

II-3-d
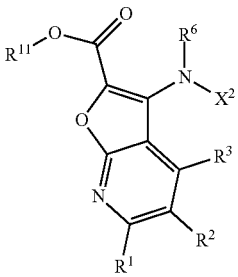

II-3-e
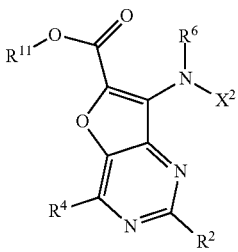

II-3-f
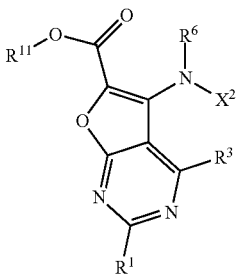

II-3-g
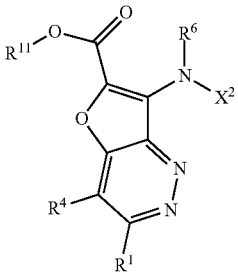

II-3-h
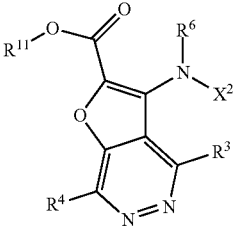

II-3-i
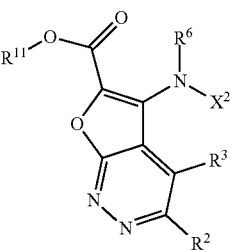

or a pharmaceutically acceptable salt or solvate thereof, wherein the variables are as defined for the formula (II) or as defined in WO 2008/024725 A1, incorporated herein by reference.

In some embodiments, the MEK inhibitor compound of the formula (II) is a compound selected from the compounds of Examples 5-18, 20-102, 105-109, 111-118, 120-133, 136-149 and 151-160 in WO 2008/024725 A1 (herein collectively referred to as the Formula II Species), or a pharmaceutically acceptable salt or solvate thereof. These compounds exhibited an $IC_{50}$ of less than 10 µM in the assay described either in Example 8a or 8b (MEK activity assays). Most of these compounds exhibited an $IC_{50}$ of less than 5 µM. See page 62 in WO 2008/024725 A1.

Also embraced are MEK inhibitor compounds (and/or solvates and salts thereof) described in WO 2008/024725 A1, which is incorporated herein by reference, for example, aza-benzofuran compounds of the formula (II) (designated as formula I in WO 2008/024725 A1, e.g., on page 3) and variations thereof as described in WO 2008/024725 A1. Compounds of formula (II) can be synthesized using methods known in the art, for example, the synthetic methods described in WO 2008/024725 A1, incorporated herein by reference.

In some embodiments, the MEK inhibitor is a compound of formula (III):

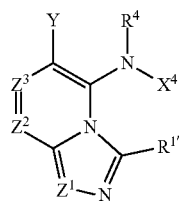

(III)

or a pharmaceutically acceptable salt or solvate thereof, wherein:
$Z^1$ is $CR^1$ or N;
$R^1$ is H, $C_1$-$C_3$ alkyl, halo, $CF_3$, $CHF_2$, CN, $OR^A$ or $NR^AR^A$;
$R^{1'}$ is H, $C_1$-$C_3$ alkyl, halo, $CF_3$, $CHF_2$, CN, $OR^A$, or $NR^AR^A$;

wherein each $R^A$ is independently H or $C_1$-$C_3$ alkyl;
$Z^2$ is $CR^2$ or N;
$Z^3$ is $CR^3$ or N; provided that only one of $Z^1$, $Z^2$ and $Z^3$ can be N at the same time;
$R^2$ and $R^3$ are independently selected from H, halo, CN, $CF_3$, —$OCF_3$, —$NO_2$, —$(CR^{14}R^{15})_nC(=Y')R^{11}$, —$(CR^{14}R^{15})_nC(=Y')OR^{11}$, —$(CR^{14}R^{15})_nC(=Y')NR^{11}R^{12}$, —$(CR^{14}R^{15})_nNR^{11}R^{12}$, —$(CR^{14}R^{15})_nOR^{11}$, —$(CR^{14}R^{15})_nSR^{11}$, —$(CR^{14}R^{15})_nNR^{12}C(=Y')R^{11}$, —$(CR^{14}R^{15})_nNR^{12}C(=Y')OR^{11}$, —$(CR^{14}R^{15})_nNR^{13}C(=Y')NR^{11}R^{12}$, —$(CR^{14}R^{15})_nNR^{12}SO_2R^{11}$, —$(CR^{14}R^{15})_nOC(=Y')R^{11}$, —$(CR^{14}R^{15})_nOC(=Y')OR^{11}$, —$(CR^{14}R^{15})_nOC(=Y')NR^{11}R^{12}$, —$(CR^{14}R^{15})_nOS(O)_2(OR^{11})$, —$(CR^{14}R^{15})_nOP(=Y')(OR^{11})(OR^{12})$, —$(CR^{14}R^{15})_nOP(OR^{11})(OR^{12})$, —$(CR^{14}R^{15})_nS(O)R^{11}$, —$(CR^{14}R^{15})_nS(O)_2R^{11}$, —$(CR^{14}R^{15})_nS(O)_2NR^{11}R^{12}$, —$(CR^{14}R^{15})_nS(O)(OR^{11})$, —$(CR^{14}R^{15})_nS(O)_2(OR^{11})$, —$(CR^{14}R^{15})_nSC(=Y')R^{11}$, —$(CR^{14}R^{15})_nSC(=Y')OR^{11}$, —$(CR^{14}R^{15})_nSC(=Y')NR^{11}R^{12}$, $C_1$-$C_{12}$ alkyl, $C_2$-$C_8$ alkenyl, $C_2$-$C_8$ alkynyl, carbocyclyl, heterocyclyl, aryl, and heteroaryl;
$R^4$ is H, $C_1$-$C_6$ alkyl or $C_3$-$C_4$ carbocyclyl;
Y is W—C(O)— or W';
W is

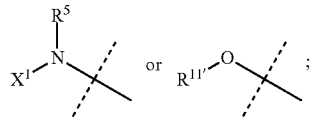

$R^5$ is H or $C_1$-$C_{12}$ alkyl;
$X^1$ is selected from $R^{11'}$ and —$OR^{11'}$; when $X^1$ is $R^{11'}$, $X^1$ is optionally taken together with $R^5$ and the nitrogen atom to which they are bound to form a 4-7 membered saturated or unsaturated ring having 0-2 additional heteroatoms selected from O, S and N, wherein said ring is optionally substituted with one or more groups selected from halo, CN, $CF_3$, —$OCF_3$, —$NO_2$, oxo, —$(CR^{19}R^{20})_nC(=Y')R^{16}$, —$(CR^{19}R^{20})_nC(=Y')OR^{16}$, —$(CR^{19}R^{20})_nC(=Y')NR^{16}R^{17}$, —$(CR^{19}R^{20})_nNR^{16}R^{17}$, —$(CR^{19}R^{20})_nOR^{16}$, —$(CR^{19}R^{20})_n$—$SR^{16}$, —$(CR^{19}R^{20})_nNR^{16}C(=Y')R^{17}$, —$(CR^{19}R^{20})_nNR^{16}C(=Y')OR^{17}$, —$(CR^{19}R^{20})_nNR^{18}C(=Y')NR^{16}R^{17}$, —$(CR^{19}R^{20})_nNR^{17}SO_2R^{16}$, —$(CR^{19}R^{20})_nOC(=Y')R^{16}$, —$(CR^{19}R^{20})_nOC(=Y')OR^{16}$, —$(CR^{19}R^{20})_nOC(=Y')NR^{16}R^{17}$, —$(CR^{19}R^{20})_nOS(O)_2(OR^{16})$, —$(CR^{19}R^{20})_nOP(=Y')(OR^{16})(OR^{17})$, —$(CR^{19}R^{20})_nOP(OR^{16})(OR^{17})$, —$(CR^{19}R^{20})_nS(O)R^{16}$, —$(CR^{19}R^{20})_nS(O)_2R^{16}$, —$(CR^{19}R^{20})_nS(O)_2NR^{16}R^{17}$, —$(CR^{19}R^{20})_nS(O)(OR^{16})$, —$(CR^{19}R^{20})_nS(O)_2(OR^{16})$, —$(CR^{19}R^{20})_nSC(=Y')R^{16}$, —$(CR^{19}R^{20})_nSC(=Y')OR^{16}$, —$(CR^{19}R^{20})_nSC(=Y')NR^{16}R^{17}$, and $R^{21}$;
each $R^{11'}$ is independently H, $C_1$-$C_{12}$ alkyl, $C_2$-$C_8$ alkenyl, $C_2$-$C_8$ alkynyl, carbocyclyl, heterocyclyl, aryl, or heteroaryl;
$R^{11}$, $R^{12}$ and $R^{13}$ are independently H, $C_1$-$C_{12}$ alkyl, $C_2$-$C_8$ alkenyl, $C_2$-$C_8$ alkynyl, carbocyclyl, heterocyclyl, aryl, or heteroaryl,
or $R^{11}$ and $R^{12}$ together with the nitrogen to which they are attached form a 3-8 membered saturated, unsaturated or aromatic ring having 0-2 heteroatoms selected from O, S and N, wherein said ring is optionally substituted with one or more groups selected from halo, CN, $CF_3$, —$OCF_3$, —$NO_2$, $C_1$-$C_6$ alkyl, —OH, —SH, —O($C_1$-$C_6$ alkyl), —S($C_1$-$C_6$ alkyl), —$NH_2$, —NH ($C_1$-$C_6$ alkyl), —N($C_1$-$C_6$ alkyl)$_2$, —$SO_2$($C_1$-$C_6$ alkyl), —$CO_2$H, —$CO_2$($C_1$-$C_6$ alkyl), —C(O)$NH_2$, —C(O) NH($C_1$-$C_6$ alkyl), —C(O)N($C_1$-$C_6$ alkyl)$_2$, —N($C_1$-$C_6$ alkyl)C(O)($C_1$-$C_6$ alkyl), —NHC(O)($C_1$-$C_6$ alkyl), —$NHSO_2$($C_1$-$C_6$ alkyl), —N($C_1$-$C_6$ alkyl)$SO_2$($C_1$-$C_6$ alkyl), —$SO_2NH_2$, —$SO_2$NH($C_1$-$C_6$ alkyl), —$SO_2$N ($C_1$-$C_6$ alkyl)$_2$, —OC(O)$NH_2$, —OC(O)NH($C_1$-$C_6$ alkyl), —OC(O)N($C_1$-$C_6$ alkyl)$_2$, —OC(O)O($C_1$-$C_6$ alkyl), —NHC(O)NH($C_1$-$C_6$ alkyl), —NHC(O)N($C_1$-$C_6$ alkyl)$_2$, —N($C_1$-$C_6$ alkyl)C(O)NH($C_1$-$C_6$ alkyl), —N($C_1$-$C_6$ alkyl)C(O)N($C_1$-$C_6$ alkyl)$_2$, —NHC(O)NH ($C_1$-$C_6$ alkyl), —NHC(O)N($C_1$-$C_6$ alkyl)$_2$, —NHC(O)O($C_1$-$C_6$ alkyl), and —N($C_1$-$C_6$ alkyl)C(O)O($C_1$-$C_6$ alkyl);
$R^{14}$ and $R^{15}$ are independently selected from H, $C_1$-$C_{12}$ alkyl, aryl, carbocyclyl, heterocyclyl, and heteroaryl;
W' is

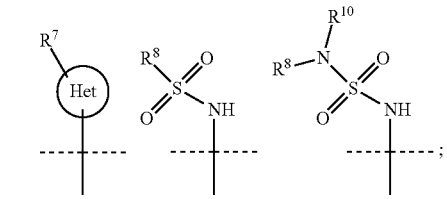

wherein

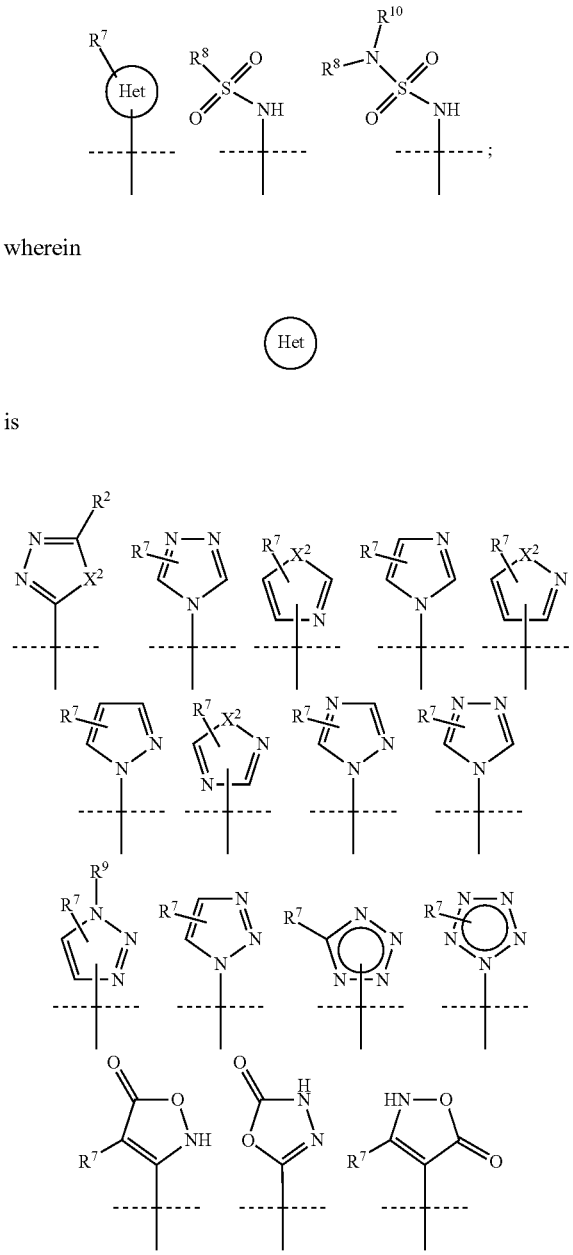

each $X^2$ is independently O, S, or $NR^9$;

each $R^7$ is independently selected from H, halo, CN, $CF_3$, $-OCF_3$, $-NO_2$, $-(CR^{14}R^{15})_nC(=Y')R^{11}$, $-(CR^{14}R^{15})_nC(=Y')OR^{11}$, $-(CR^{14}R^{15})_nC(=Y')NR^{11}R^{12}$, $-(CR^{14}R^{15})_nNR^{11}R^{12}$, $-(CR^{14}R^{15})_nOR^{11}$, $-(CR^{14}R^{15})_nSR^{11}$, $-(CR^{14}R^{15})_nNR^{12}C(=Y')R^{11}$, $-(CR^{14}R^{15})_nNR^{12}C(=Y')OR^{11}$, $-(CR^{14}R^{15})_nNR^{13}C(=Y')NR^{11}R^{12}$, $-(CR^{14}R^{15})_nNR^{12}SO_2R^{11}$, $-(CR^{14}R^{15})_nOC(=Y')R^{11}$, $-(CR^{14}R^{15})_nOC(=Y')OR^{11}$, $-(CR^{14}R^{15})_nOC(=Y')NR^{11}R^{12}$, $-(CR^{14}R^{15})_nOS(O)_2(OR^{11})$, $-(CR^{14}R^{15})_nO(=Y')(OR^{11})(OR^{12})$, $-(CR^{14}R^{15})_nOP(OR^{11})(OR^{12})$, $-(CR^{14}R^{15})_nS(O)R^{11}$, $-(CR^{14}R^{15})_nS(O)_2R^{11}$, $-(CR^{14}R^{15})_nS(O)_2NR^{11}R^{12}$, $-(CR^{14}R^{15})_nS(O)(OR^{11})$, $-(CR^{14}R^{15})_nS(O)_2(OR^{11})$, $-(CR^{14}R^{15})_nSC(=Y')R^{11}$, $-(CR^{14}R^{15})_nSC(=Y')OR^{11}$, $-(CR^{14}R^{15})_nSC(=Y')NR^{11}R^{12}$, $C_1-C_{12}$ alkyl, $C_2-C_8$ alkenyl, $C_2-C_8$ alkynyl, carbocyclyl, heterocyclyl, aryl, and heteroaryl;

each $R^8$ is independently selected from $C_1-C_{12}$ alkyl, aryl, carbocyclyl, heterocyclyl, and heteroaryl;

$R^9$ is selected from H, $-(CR^{14}R^{15})_nC(=Y')R^{11}$, $-(CR^{14}R^{15})_nC(=Y')OR^{11}$, $-(CR^{14}R^{15})_nC(=Y')NR^{11}R^{12}$, $-(CR^{14}R^{15})_qNR^{11}R^{12}$, $-(CR^{14}R^{15})_qOR^{11}$, $-(CR^{14}R^{15})_qSR^{11}$, $-(CR^{14}R^{15})_qNR^{12}C(=Y')R^{11}$, $-(CR^{14}R^{15})_qNR^{12}C(=Y')OR^{11}$, $-(CR^{14}R^{15})_qNR^{13}C(=Y')NR^{11}R^{12}$, $-(CR^{14}R^{15})_qNR^{12}SO_2R^{11}$, $-(CR^{14}R^{15})_qOC(=Y')R^{11}$, $-(CR^{14}R^{15})_qOC(=Y')OR^{11}$, $-(CR^{14}R^{15})_qOC(=Y')NR^{11}R^{12}$, $-(CR^{14}R^{15})_qOS(O)_2(OR^{11})$, $-(CR^{14}R^{15})_qOP(=Y')(OR^{11})(OR^{12})$, $-(CR^{14}R^{15})_qOP(OR^{11})(OR^{12})$, $-(CR^{14}R^{15})_nS(O)R^{11}$, $-(CR^{14}R^{15})_nS(O)_2R^{11}$, $-(CR^{14}R^{15})_nS(O)_2NR^{11}R^{12}$, $C_1-C_{12}$ alkyl, $C_2-C_8$ alkenyl, $C_2-C_8$ alkynyl, carbocyclyl, heterocyclyl, aryl, and heteroaryl;

$R^{10}$ is H, $C_1-C_6$ alkyl or $C_3-C_4$ carbocyclyl;

$X^4$ is

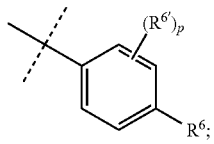

$R^6$ is H, halo, $C_1-C_6$ alkyl, $C_2-C_8$ alkenyl, $C_2-C_8$ alkynyl, carbocyclyl, heteroaryl, heterocyclyl, $-OCF_3$, $-NO_2$, $-Si(C_1-C_6$ alkyl), $-(CR^{19}R^{20})_nNR^{16}R^{17}$, $-(CR^{19}R^{20})_nOR^{16}$, or $-(CR^{19}R^{20})_n-SR^{16}$, $R^{6'}$ is H, halo, $C_1-C_6$ alkyl, carbocyclyl, $CF_3$, $-OCF_3$, $-NO_2$, $-Si(C_1-C_6$ alkyl), $-(CR^{19}R^{20})_nNR^{16}R^{17}$, $-(CR^{19}R^{20})_nOR^{16}$, $-(CR^{19}R^{20})_n-SR^{16}$, $C_2-C_8$ alkenyl, $C_2-C_8$ alkynyl, heterocyclyl, aryl, or heteroaryl;

p is 0, 1, 2 or 3;

n is 0, 1, 2 or 3;

q is 2 or 3;

wherein each said alkyl, alkenyl, alkynyl, carbocyclyl, heterocyclyl, aryl and heteroaryl of $R^1$, $R^2$, $R^3$, $R^4$, $R^5$, $R^6$, $R^{6'}$, $R^7$, $R^8$, $R^9$, $R^{10}$, $R^{11}$, $R^{11'}$, $R^{12}$, $R^{13}$, $R^{14}$, $R^{15}$ and $R^A$ is independently optionally substituted with one or more groups independently selected from halo, CN, $CF_3$, $-OCF_3$, $-NO_2$, oxo, $-Si(C_1-C_6$ alkyl), $-(CR^{19}R^{20})_nC(=Y')R^{16}$, $-(CR^{19}R^{20})_nC(=Y')OR^{16}$, $-(CR^{19}R^{20})_nC(=Y')NR^{16}R^{17}$, $-(CR^{19}R^{20})_nNR^{16}R^{17}$, $-(CR^{19}R^{20})_nOR^{16}$, $-(CR^{19}R^{20})_nSR^{16}$, $-(CR^{19}R^{20})_nNR^{16}C(=Y')R^{17}$, $-(CR^{19}R^{20})_nNR^{16}C(=Y')OR^{17}$, $-(CR^{19}R^{20})_nNR^{18}C(=Y')NR^{16}R^{17}$, $-(CR^{19}R^{20})_nNR^{17}SO_2R^{16}$, $-(CR^{19}R^{20})_nOC(=Y')R^{16}$, $-(CR^{19}R^{20})_nOC(=Y')OR^{16}$, $-(CR^{19}R^{20})_nOC(=Y')NR^{16}R^{17}$, $-(CR^{19}R^{20})_nOS(O)_2(OR^{16})$, $-(CR^{19}R^{20})_nOP(=Y')(OR^{16})(OR^{17})$, $-(CR^{19}R^{20})_nOP(OR^{16})(OR^{17})$, $-(CR^{19}R^{20})_nS(O)R^{16}$, $-(CR^{19}R^{20})_nS(O)_2R^{16}$, $-(CR^{19}R^{20})_nS(O)_2NR^{16}R^{17}$, $-(CR^{19}R^{20})_nS(O)(OR^{16})$, $-(CR^{19}R^{20})_nS(O)_2(OR^{16})$, $-(CR^{19}R^{20})_nSC(=Y')R^{16}$, $-(CR^{19}R^{20})_nSC(=Y')OR^{16}$, $-(CR^{19}R^{20})_nSC(=Y')NR^{16}R^{17}$, and $R^{21}$;

each $R^{16}$, $R^{17}$ and $R^{18}$ is independently H, $C_1-C_{12}$ alkyl, $C_2-C_8$ alkenyl, $C_2-C_8$ alkynyl, carbocyclyl, heterocyclyl, aryl, or heteroaryl, wherein said alkyl, alkenyl, alkynyl, carbocyclyl, heterocyclyl, aryl, or heteroaryl is optionally substituted with one or more groups selected from halo, CN, $-OCF_3$, $CF_3$, $-NO_2$, $C_1-C_6$ alkyl, $-OH$, $-SH$, $-O(C_1-C_6$ alkyl), $-S(C_1-C_6$ alkyl), $-NH_2$, $-NH(C_1-C_6$ alkyl), $-N(C_1-C_6$ alkyl)$_2$, $-SO_2(C_1-C_6$ alkyl), $-CO_2H$, $-CO_2(C_1-C_6$ alkyl), $-C(O)NH_2$, $-C(O)NH(C_1-C_6$ alkyl), $-C(O)N(C_1-C_6$ alkyl)$_2$, $-N(C_1-C_6$ alkyl)$C(O)(C_1-C_6$ alkyl), $-NHC(O)(C_1-C_6$ alkyl), $-NHSO_2(C_1-C_6$ alkyl), $-N(C_1-C_6$ alkyl)$SO_2(C_1-C_6$ alkyl), $-SO_2NH_2$, $-SO_2NH(C_1-C_6$ alkyl), $-SO_2N(C_1-C_6$ alkyl)$_2$, $-OC(O)NH_2$, $-OC(O)NH(C_1-C_6$ alkyl), $-OC(O)N(C_1-C_6$ alkyl)$_2$, $-OC(O)O(C_1-C_6$ alkyl), $-NHC(O)NH(C_1-C_6$ alkyl), $-NHC(O)N(C_1-C_6$ alkyl)$_2$, $-N(C_1-C_6$ alkyl)$C(O)NH(C_1-C_6$ alkyl), $-N(C_1-C_6$ alkyl)$C(O)N(C_1-C_6$ alkyl)$_2$, $-NHC(O)NH(C_1-C_6$ alkyl), $-NHC(O)N(C_1-C_6$ alkyl)$_2$, $-NHC(O)O(C_1-C_6$ alkyl), and $-N(C_1-C_6$ alkyl)$C(O)O(C_1-C_6$ alkyl);

or $R^{16}$ and $R^{17}$ together with the nitrogen to which they are attached form a 3-8 membered saturated, unsaturated or aromatic ring having 0-2 heteroatoms selected from O, S and N, wherein said ring is optionally substituted with one or more groups selected from halo, CN, $-OCF_3$, $CF_3$, $-NO_2$, $C_1-C_6$ alkyl, $-OH$, $-SH$, $-O(C_1-C_6$ alkyl), $-S(C_1-C_6$ alkyl), $-NH_2$, $-NH(C_1-C_6$ alkyl), $-N(C_1-C_6$ alkyl)$_2$, $-SO_2(C_1-C_6$ alkyl), $-CO_2H$, $-CO_2(C_1-C_6$ alkyl), $-C(O)NH_2$, $-C(O)NH(C_1-C_6$ alkyl), $-C(O)N(C_1-C_6$ alkyl)$_2$, $-N(C_1-C_6$ alkyl)$C(O)(C_1-C_6$ alkyl), $-NHC(O)(C_1-C_6$ alkyl), $-NHSO_2(C_1-C_6$ alkyl), $-N(C_1-C_6$ alkyl)$SO_2(C_1-C_6$ alkyl), $-SO_2NH_2$, $-SO_2NH(C_1-C_6$ alkyl), $-SO_2N(C_1-C_6$ alkyl)$_2$, $-OC(O)NH_2$, $-OC(O)NH(C_1-C_6$ alkyl), $-OC(O)N(C_1-C_6$ alkyl)$_2$, $-OC(O)O(C_1-C_6$ alkyl), $-NHC(O)NH(C_1-C_6$ alkyl), $-NHC(O)N(C_1-C_6$ alkyl)$_2$, $-N(C_1-C_6$ alkyl)$C(O)NH(C_1-C_6$ alkyl), $-N(C_1-C_6$ alkyl)$C(O)N(C_1-C_6$ alkyl)$_2$, $-NHC(O)NH(C_1-C_6$ alkyl), $-NHC(O)N(C_1-C_6$ alkyl)$_2$, $-NHC(O)O(C_1-C_6$ alkyl), and $-N(C_1-C_6$ alkyl)$C(O)O(C_1-C_6$ alkyl);

$R^{19}$ and $R^{20}$ are independently selected from H, $C_1-C_{12}$ alkyl, $-(CH_2)_n$-aryl, $-(CH_2)_n$-carbocyclyl, $-(CH_2)_n$-heterocyclyl, and $-(CH_2)_n$-heteroaryl;

$R^{21}$ is $C_1-C_{12}$ alkyl, $C_2-C_8$ alkenyl, $C_2-C_8$ alkynyl, carbocyclyl, heterocyclyl, aryl, or heteroaryl, wherein each member of $R^{21}$ is optionally substituted with one or more groups selected from halo, oxo, CN, $-OCF_3$, $CF_3$, $-NO_2$, $C_1-C_6$ alkyl, $-OH$, $-SH$, $-O(C_1-C_6$ alkyl), $-S(C_1-C_6$ alkyl), $-NH_2$, $-NH(C_1-C_6$ alkyl), $-N(C_1-C_6$ alkyl)$_2$, $-SO_2(C_1-C_6$ alkyl), $-CO_2H$, $-CO_2(C_1-C_6$ alkyl), $-C(O)NH_2$, $-C(O)NH(C_1-C_6$ alkyl), $-C(O)N(C_1-C_6$ alkyl)$_2$, $-N(C_1-C_6$ alkyl)$C(O)(C_1-C_6$ alkyl), $-NHC(O)(C_1-C_6$ alkyl), $-NHSO_2(C_1-C_6$ alkyl), $-N(C_1-C_6$ alkyl)$SO_2(C_1-C_6$ alkyl), $-SO_2NH_2$, $-SO_2NH(C_1-C_6$ alkyl), $-SO_2N(C_1-C_6$ alkyl)$_2$, $-OC(O)NH_2$, $-OC(O)NH(C_1-C_6$ alkyl), $-OC(O)N(C_1-C_6$ alkyl)$_2$, $-OC(O)O(C_1-C_6$ alkyl), —NHC(O)NH(C$_1$-C$_6$ alkyl), —NHC(O)N(C$_1$-C$_6$ alkyl)$_2$, —N(C$_1$-C$_6$ alkyl)C(O)NH(C$_1$-C$_6$ alkyl), —N(C$_1$-C$_6$ alkyl)C(O)N(C$_1$-C$_6$ alkyl)$_2$, —NHC(O)NH (C$_1$-C$_6$ alkyl), —NHC(O)N(C$_1$-C$_6$ alkyl)$_2$, —NHC(O) O(C$_1$-C$_6$ alkyl), and —N(C$_1$-C$_6$ alkyl)C(O)O(C$_1$-C$_6$ alkyl);

each Y' is independently O, NR$^{22}$, or S; and
R$^{22}$ is H or C$_1$-C$_{12}$ alkyl.

In some variations, the MEK inhibitor compound of the formula (III) has the formula (III-a) or (III-b):

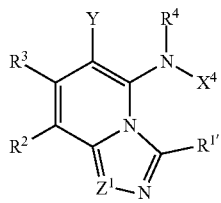

III-a

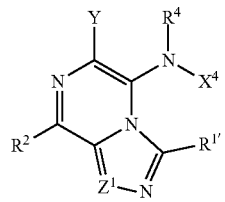

III-b or a pharmaceutically acceptable salt or solvate thereof, wherein the variables are as defined for the formula (III) or as defined in WO 2009/085983 A1, incorporated herein by reference.

In some embodiments, the MEK inhibitor compound of the formula (III) is a compound selected from the compounds listed in Table 1, or a pharmaceutically acceptable salt or solvate thereof.

TABLE 1

| Compound No. | Chemical Name | Structure |
| --- | --- | --- |
| (III)-5 | 5-(2-Fluoro-4-iodophenylamino)-imidazo[1,5-a]pyridine-6-carboxylic acid (2-hydroxyethoxy)-amide | 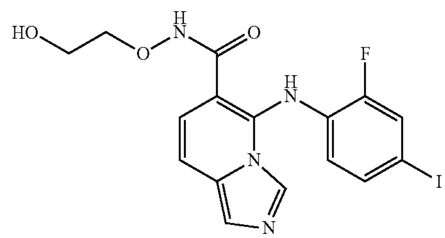 [SMILES: O=C(NOCCO)c1ccc2cncn2c1Nc1ccc(I)cc1F] |
| (III)-6 | 5-(2-Fluoro-4-iodo-phenylamino)-imidazo[1,5-a]pyridine-6-carboxylic acid ((R)-2,3-dihydroxy-propoxy)-amide | 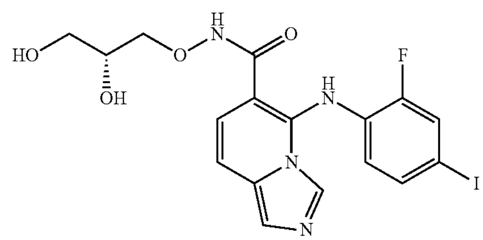 [SMILES: O=C(NOC[C@H](O)CO)c1ccc2cncn2c1Nc1ccc(I)cc1F] |
| (III)-7 | 5-(2-Fluoro-4-iodo-phenylamino)-imidazo[1,5-a]pyridine-6-carboxylic acid ((S)-2-hydroxy-propoxy)-amide | 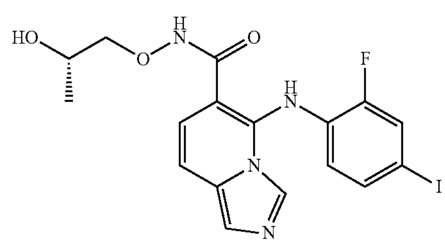 [SMILES: C[C@H](O)CONC(=O)c1ccc2cncn2c1Nc1ccc(I)cc1F] |
| (III)-8 | 5-(4-Bromo-2-fluorophenylamino)-imidazo[1,5-a]pyridine-6-carboxylic acid (2-hydroxyethoxy)-amide | 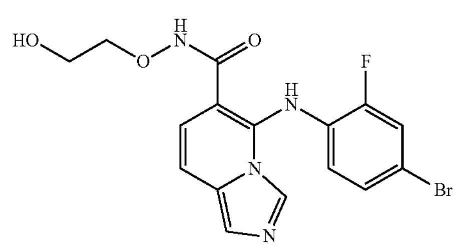 |

TABLE 1-continued

| Compound No. | Chemical Name | Structure |
|---|---|---|
| (III)-9 | 5-(4-Bromo-2-fluoro-phenylamino)-imidazo[1,5-a]pyridine-6-carboxylic acid ((S)-2-hydroxy-propoxy)-amide | 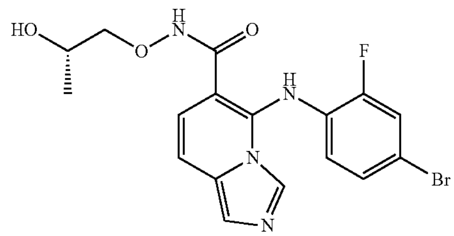 [SMILES: C[C@H](O)CONC(=O)c1ccc2cncn2c1Nc1ccc(Br)cc1F] |
| (III)-10 | 5-(4-Bromo-2-fluoro-phenylamino)-8-fluoro-imidazo[1,5-a]pyridine-6-carboxylic acid ((S)-2-hydroxy-propoxy)-amide | 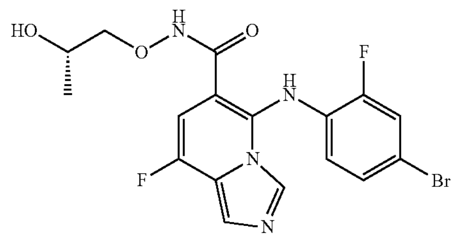 [SMILES: C[C@H](O)CONC(=O)c1cc(F)c2cncn2c1Nc1ccc(Br)cc1F] |
| (III)-11 | 8-Fluoro-5-(2-fluoro-4-iodo-phenylamino)-imidazo[1,5-a]pyridine-6-carboxylic acid (2-hydroxy-ethoxy)-amide | 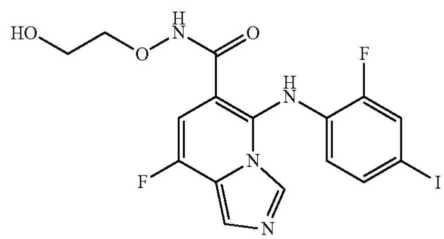 [SMILES: O=C(NOCCO)c1cc(F)c2cncn2c1Nc1ccc(I)cc1F] |
| (III)-12 | 8-Fluoro-5-(2-fluoro-4-iodo-phenylamino)-imidazo[1,5-a]pyridine-6-carboxylic acid ((R)-2,3-dihydroxy-propoxy)-amide | 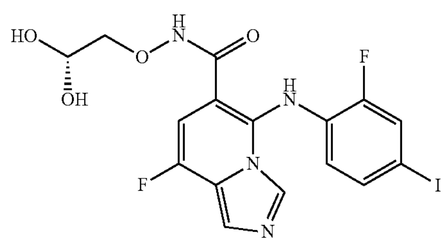 |
| (III)-13 | 8-Fluoro-5-(2-fluoro-4-iodo-phenylamino)-imidazo[1,5-a]pyridine-6-carboxylic acid ((S)-2-hydroxy-propoxy)-amide | 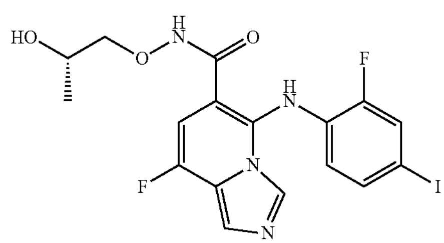 [SMILES: C[C@H](O)CONC(=O)c1cc(F)c2cncn2c1Nc1ccc(I)cc1F] |
| (III)-14 | 5-(2-Fluoro-methanesulfanyl-phenylamino)-imidazo[1,5-a]pyridine-6-carboxylic acid (2-hydroxy-ethoxy)-amide | 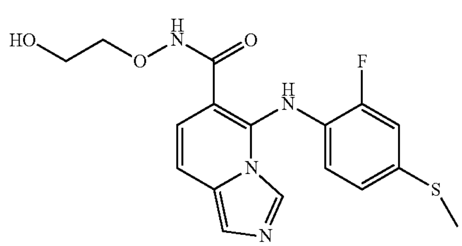 [SMILES: CSc1ccc(Nc2c(C(=O)NOCCO)ccc3cncn23)c(F)c1] |

TABLE 1-continued

| Compound No. | Chemical Name | Structure |
|---|---|---|
| (III)-15 | 5-(2-Fluoro-4-iodo-phenylamino)-imidazo[1,5-a]pyrazine-6-carboxylic acid (2-hydroxy-ethoxy)-amide | 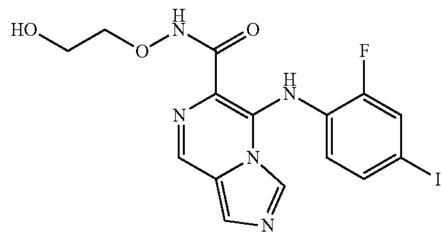 [SMILES: O=C(NOCCO)c1ncc2cncn2c1Nc1ccc(I)cc1F] |
| (III)-16 | 5-(2-Fluoro-4-iodo-phenylamino)-imidazo[1,5-a]pyrazine-6-carboxylic acid ((S)-2-hydroxy-propoxy)-amide | 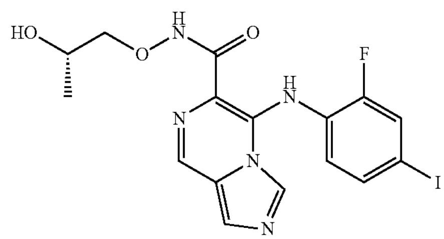 [SMILES: C[C@H](O)CONC(=O)c1ncc2cncn2c1Nc1ccc(I)cc1F] |
| (III)-17 | 5-(4-Cyclopropyl-2-fluoro-phenylamino)-imidazo[1,5-a]pyridine-6-carboxylic acid (2-hydroxy-ethoxy)-amide | 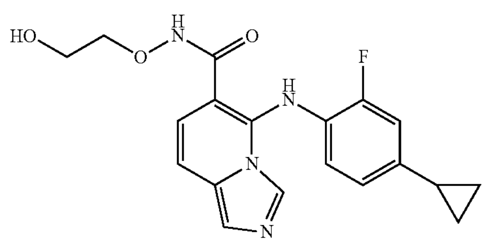 [SMILES: O=C(NOCCO)c1ccc2cncn2c1Nc1ccc(C2CC2)cc1F] |
| (III)-18 | (R)-N-(2,3-Dihydroxypropoxy)-5-(2-fluoro-4-iodophenylamino)imidazo[1,5-a]pyrazine-6-carboxamide | 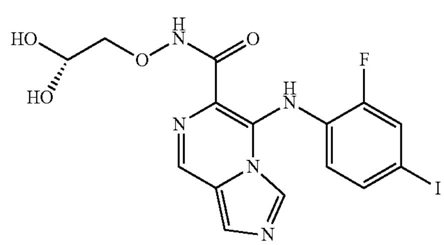 |
| (III)-19 | N-Ethoxy-5-(2-fluoro-4-iodophenylamino)imidazo[1,5-a]pyrazine-6-carboxamide | 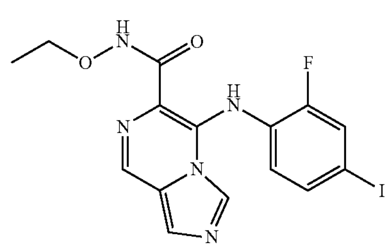 [SMILES: CCONC(=O)c1ncc2cncn2c1Nc1ccc(I)cc1F] |
| (III)-20 | N-(Cyclopropylmethoxy)-5-(2-fluoro-4-iodophenylamino)imidazo[1,5-a]pyrazine-6-carboxamide | 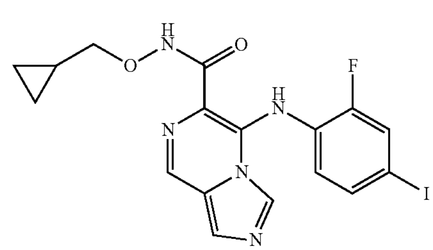 [SMILES: O=C(NOCC1CC1)c1ncc2cncn2c1Nc1ccc(I)cc1F] |

TABLE 1-continued

| Compound No. | Chemical Name | Structure |
|---|---|---|
| (III)-21 | 5-(2-Fluoro-4-iodophenylamino)-N-methylimidazo[1,5-a]pyrazine-6-carboxamide | 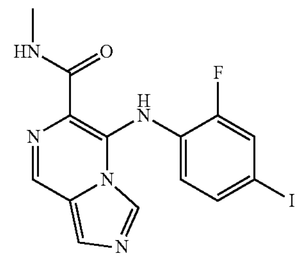 [SMILES: CNC(=O)c1ncc2cncn2c1Nc1ccc(I)cc1F] |
| (III)-22 | 5-(4-Bromo-2-fluorophenylamino)-N-(2-hydroxy-ethoxy)imidazo[1,5-a]pyrazine-6-carboxamide | 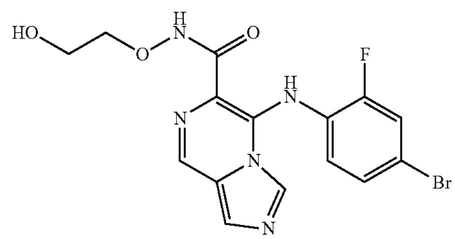 [SMILES: O=C(NOCCO)c1ncc2cncn2c1Nc1ccc(Br)cc1F] |
| (III)-23 | (S)-5-(4-Bromo-2-fluorophenylamino)-N-(2-hydroxy-propoxy)imidazo[1,5-a]pyrazine-6-carboxamide | 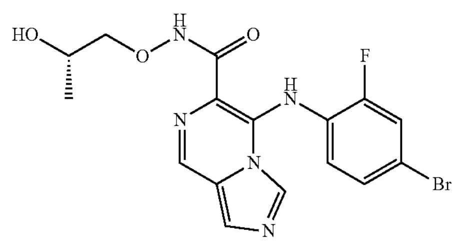 [SMILES: C[C@H](O)CONC(=O)c1ncc2cncn2c1Nc1ccc(Br)cc1F] |
| (III)-24 | (R)-5-(4-Bromo-2-fluorophenylamino)-N-(2,3-dihydroxy-propoxy)imidazo[1,5-a]pyrazine-6-carboxamide | 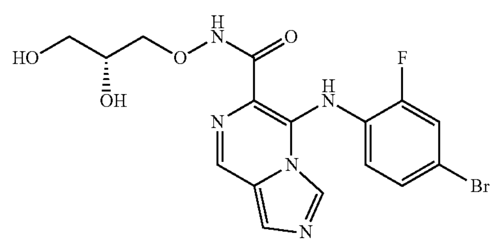 [SMILES: O=C(NOC[C@H](O)CO)c1ncc2cncn2c1Nc1ccc(Br)cc1F] |
| (III)-25 | 5-(4-Bromo-2-fluorophenylamino)-N-(cyclopropyl-methoxy)imidazo[1,5-a]pyrazine-6-carboxamide | 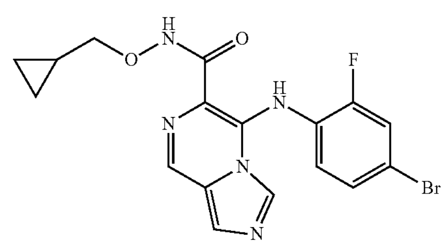 [SMILES: O=C(NOCC1CC1)c1ncc2cncn2c1Nc1ccc(Br)cc1F] |

Compounds in Table 1 correspond to Examples 5-25 in WO 2009/085983 A1. Compounds (III)-5-(III)-20 and (III)-22-(III)-24 exhibited an $IC_{50}$ of less than 0.5 µM in the assay described in Example 8b (MEK activity assay). Some of these compounds exhibited an $IC_{50}$ of less than 0.1 µM. Compounds (III)-21 and (III)-25 exhibited an $IC_{50}$ of less than 10 µM. See page 49 in WO 2009/085983 A1.

Also embraced are MEK inhibitor compounds (and/or solvates and salts thereof) described in WO 2009/085983 A1, which is incorporated herein by reference, for example, imidazopyridine compounds of the formula (III) (designated as formula I in WO 2009/085983 A1, e.g., on page 3) and variations thereof as described in WO 2009/085983 A1. Compounds of formula (III) can be synthesized using methods known in the art, for example, the synthetic methods described in WO 2009/085983 A1, incorporated herein by reference.

In some embodiments, the MEK inhibitor is a compound of formula (IV),

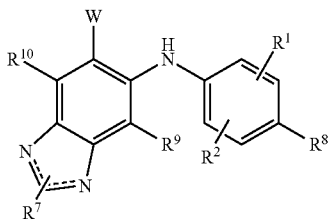

IV or a pharmaceutically acceptable salt or solvate thereof, wherein the variables are as defined in WO 03/077914 A1 for the formula I on pages 4-9 or any applicable variations described in WO 03/077914 A1, incorporated herein by reference.

In some variations, the MEK inhibitor compound of the formula (IV) is a compound of the formula (IV-a), (IV-b), (IV-c), or (IV-d):

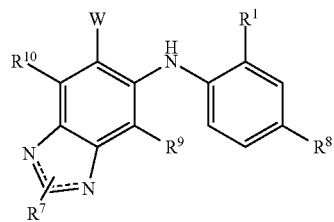

IV-a

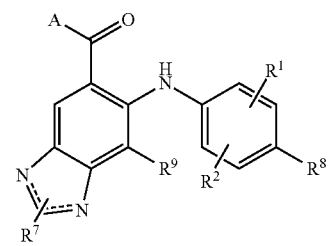

IV-b

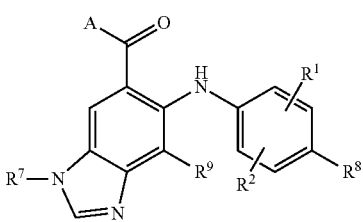

IV-c

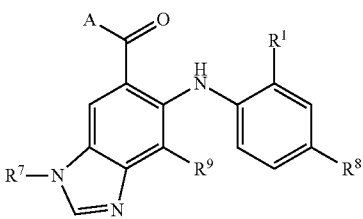

IV-d or a pharmaceutically acceptable salt or solvate thereof, wherein the variables are as defined in WO 03/077914 A1 for the formulae II, III, IIIa and IIIb, respectively on pages 10-13 or any applicable variations described in WO 03/077914 A1, incorporated herein by reference.

In some embodiments, the MEK inhibitor compound of the formula (IV) is a compound selected from the group consisting of:

7-Fluoro-6-(4-bromo-2-methyl-phenylamino)-3H-benzoimidazole-5-carboxylic acid cyclopropylmethoxy-amide;
6-(4-Bromo-2-chloro-phenylamino)-7-fluoro-3H-benzoimidazole-5-carboxylic acid cyclopropylmethoxy-amide;
6-(4-Bromo-2-chloro-phenylamino)-7-fluoro-3-methyl-3H-benzoimidazole-5-carboxylic acid (2-hydroxy-ethoxy)-amide;
6-(4-Bromo-2-chloro-phenylamino)-7-fluoro-3-methyl-3H-benzoimidazole-5-carboxylic acid (2,3-dihydroxy-propoxy)-amide;
6-(4-Bromo-2-chloro-phenylamino)-7-fluoro-3-(tetrahydropyran-2-ylmethyl)-3H-benzoimidazole-5-carboxylic acid (2-hydroxy-ethoxy)-amide;
[6-(5-Amino-[1,3,4]oxadiazol-2-yl)-4-fluoro-1H-benzoimidazol-5-yl]-(4-bromo-2-methyl-phenyl)-amine;
1-[6-(4-Bromo-2-chloro-phenylamino)-7-fluoro-3-methyl-3H-benzoimidazol-5-yl]-2-hydroxy-ethanone;
1-[6-(4-Bromo-2-chloro-phenylamino)-7-fluoro-3H-benzoimidazol-5-yl]-2-methoxy ethanone;
6-(4-Bromo-2-chloro-phenylamino)-7-fluoro-3-methyl-3H-benzoimidazole-5-carboxylic acid (2-hydroxy-1,1-dimethyl-ethoxy)-amide;
6-(4-Bromo-2-chloro-phenylamino)-7-fluoro-3-(tetrahydrofuran-2-ylmethyl)-3H-benzoimidazole-5-carboxylic acid (2-hydroxy-ethoxy)-amide;
6-(4-Bromo-2-chloro-phenylamino)-7-fluoro-3H-benzoimidazole-5-carboxylic acid (2-hydroxy-ethoxy)-amide;
6-(-Bromo-2-fluoro-phenylamino)-7-fluoro-3-methyl-3H-benzoimidazole-5-carboxylic acid (2-hydroxy-ethoxy)-amide; and
6-(2,4-Dichloro-phenylamino)-7-fluoro-3-methyl-3H-benzoimidazole-5-carboxylic acid (2-hydroxy-ethoxy)-amide;
or a pharmaceutically acceptable salt or solvate thereof.

Also embraced are any variations of formula (IV) as described in WO 03/077914 A1, which is incorporated herein by reference. Compounds of the formula (IV) or any variations thereof can be synthesized using methods known in the art, for example, the synthetic methods described in WO 03/077914 A1, incorporated herein by reference.

In some embodiments, the MEK inhibitor is a compound of formula (V),

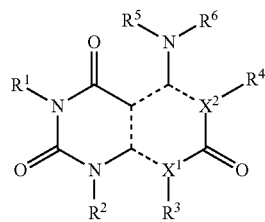

V or a pharmaceutically acceptable salt or solvate thereof, wherein the variables are as defined in WO 2005/121142 A1 for the formula [I] on pages 6-10 or any applicable variations described in WO 2005/121142 A1, incorporated herein by reference.

Also embraced are any variations of formula (V) as described in WO 2005/121142 A1, such as the individual MEK inhibitor compounds described in WO 2005/121142 A1, e.g., Examples 1-1 to 1-343 in Table 1, Examples 2-1 and 2-2 in Table 2, Examples 3-1 to 3-9 in Table 3, Examples 4-1 to 4-148 in Table 4. Compounds of the formula (V) or any variations thereof can be synthesized using methods known in the art, for example, the synthetic methods described in WO 2005/121142 A1, incorporated herein by reference.

In some embodiments, the MEK inhibitor is a compound of formula (VI),

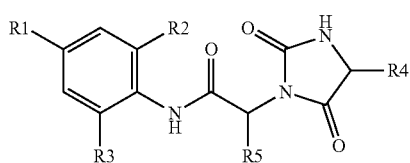

or a pharmaceutically acceptable salt or ester thereof, wherein:

R1 is selected from the group consisting of bromo, iodo, ethynyl, cycloalkyl, alkoxy, azetidinyl, acetyl, heterocycyl, cyano, straight-chained alkyl and branched-chain alkyl;

R2 is selected from the group consisting of hydrogen, chlorine, fluorine, and alkyl;

R3 is selected from the group consisting of hydrogen, chlorine, and fluorine;

R4 is selected from the group consisting of hydrogen, optionally substituted aryl, alkyl, and cycloalkyl;

R5 is selected from the group consisting of hydrogen and

wherein R6 is selected from the group consisting of hydroxyl, alkoxy, cycloalkyl, optionally substituted alkyl, optionally substituted aryl, and optionally substituted heteroaryl;

R7 and R8 are independently selected from the group consisting of hydrogen and optionally substituted alkyl;

or R6 and R7 can together form a cycloalkyl group and R8 is hydrogen.

In some variations, the MEK inhibitor compound is of the formula (VI), or a pharmaceutically acceptable salt or ester thereof, wherein the variables are as defined in WO 2007/096259 A1 for the formula I or any applicable variations described on pages 4-10 in WO 2007/096259 A1, incorporated herein by reference. Further embraced MEK inhibitors are compounds described in Examples 1-182 in WO 2007/096259 A1, incorporated herein by reference.

In some embodiments, the MEK inhibitor compound of the formula (VI) is a compound selected from the group consisting of:
(2S,3S)—N-(4-Bromo-phenyl)-2-[(R)-4-(4-methoxy-phenyl)-2,5-dioxo-imidazolidin-1-yl]-3-phenyl-butyramide;
(2S,3S)—N-(4-Iodo-phenyl)-2-[(R)-4-(4-methoxy-phenyl)-2,5-dioxo-imidazolidin-1-yl]-3-phenyl-butyramide;
(2S,3S)—N-(2-Fluoro-4-iodo-phenyl)-2-{(R)-4-[4-(2-hydroxy-ethoxy)-phenyl]-2,5-dioxo-imidazolidin-1-yl}-3-phenyl-butyramide;
(2S,3S)—N-(4-Ethynyl-2-fluoro-phenyl)-2-{(R)-4-[4-(2-hydroxy-ethoxy)-phenyl]-2,5-dioxo-imidazolidin-1-yl}-3-phenyl-butyramide;
(2R,3S)—N-(4-Ethynyl-2-fluoro-phenyl)-2-{(R)-4-[4-(2-hydroxy-ethoxy)-phenyl]-2,5-dioxo-imidazolidin-1-yl}-3-phenyl-butyramide;
(2S,3S)—N-(2-Chloro-4-iodo-phenyl)-2-{(R)-4-[4-(2-hydroxy-ethoxy)-phenyl]-2,5-dioxo-imidazolidin-1-yl}-3-phenyl-butyramide;
(2S,3S)-2-{(R)-4-[4-(2-Hydroxy-ethoxy)-phenyl]-2,5-dioxo-imidazolidin-1-yl}-N-(4-iodo-2-methyl-phenyl)-3-phenyl-butyramide;
(2S,3S)—N-(2-Chloro-4-iodo-phenyl)-2-{(R)-4-[4-((R)-2,3-dihydroxy-propoxy)-phenyl]-2,5-dioxo-imidazolidin-1-yl}-3-phenyl-butyramide;
(2S,3S)—N-(2-Chloro-4-iodo-phenyl)-2-{(R)-4-[4-((S)-2,3-di hydroxy-propoxy)-phenyl]-2,5-dioxo-imidazolidin-1-yl}-3-phenyl-butyramide;
(2S,3S)-2-{(R)-2, 5-Dioxo-4-[4-(2-oxo-2-pyrrolidin-1-yl-ethoxy)-phenyl]-imidazolidin-1-yl}-N-(2-fluoro-4-iodo-phenyl)-3-phenyl-butyramide;
(2S,3S)-2-((R)-2,5-Dioxo-4-thiophen-3-yl-imidazolidin-1-yl)-N-(4-iodo-phenyl)-3-phenyl-butyramide;
(S)-2-[(R)-4-(2,3-Dihydro-benzo[1,4]dioxin-6-yl)-2,5-dioxo-imidazolidin-1-yl]-N-(2-fluoro-4-iodo-phenyl)-3-phenyl-propionamide;
(S)-2-[(R)-4-(4-Acetylamino-phenyl)-2,5-dioxo-imidazolidin-1-yl]-N-(2-fluoro-4-iodo-phenyl)-3-phenyl-propionamide;
(4-{(R)-1-[(1S,2S)-1-(2-Fluoro-4-iodo-phenylcarbamoyl)-2-phenyl-propyl]-2,5-dioxo-imidazolidin-4-yl}-phenoxymethyl)-phosphonic acid dimethyl ester;
(2S,3S)—N-(2-Fluoro-4-iodo-phenyl)-2-((R)-4-isopropyl-2,5-dioxo-imidazolidin-1-yl)-3-phenyl-butyramide;
(S)—N-(2-Fluoro-4-iodo-phenyl)-2-{(R)-4-[4-(2-hydroxy-ethoxy)-phenyl]-2,5-dioxo-imidazolidin-1-yl}-3-methyl-butyramide;
(S)—N-(2-Fluoro-4-iodo-phenyl)-2-[(R)-4-(4-methoxy-phenyl)-2,5-dioxo-imidazolidin-1-yl]-3-o-tolyl-propionamide;
(S)—N-(2-Fluoro-4-iodo-phenyl)-2-[(R)-4-(4-methoxy-phenyl)-2,5-dioxo-imidazolidin-1-yl]-3-m-tolyl-propionamide;
(S)—N-(2-Fluoro-4-iodo-phenyl)-2-[(R)-4-(4-methoxy-phenyl)-2,5-dioxo-imidazolidin-1-yl]-3-p-tolyl-propionamide; and
(S)—N-(4-Cyclopropyl-2-fluoro-phenyl)-3-(4-fluoro-phenyl)-2-{(R)-4-[4-(2-hydroxy-1-hydroxymethyl-ethoxy)-phenyl]-2,5-dioxo-imidazolidin-1-yl}-propionamide;
or a pharmaceutically acceptable salt or ester thereof.

In some embodiments, the MEK inhibitor is a compound of formula (VII),

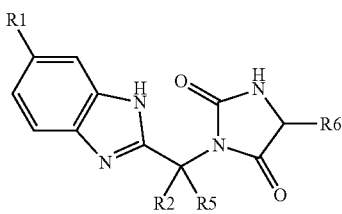

or a pharmaceutically acceptable salt or ester thereof, wherein:

R1 is selected from the group consisting of halogen, ethynyl, and cycloalkyl;

R2 is selected from the group consisting of hydrogen and CH(R3)(R4);

R3 is selected from the group consisting of lower alkyl, lower alkoxy, optionally substituted aryl, and optionally substituted heteroaryl;

R4 is selected from the group consisting of hydrogen and lower alkyl;

R5 is hydrogen or, taken together with R2 and the carbon to which R2 and R5 are attached, forms lower cycloalkyl; and R6 is selected from the group consisting of hydrogen, lower alkyl, lower cycloalkyl, optionally substituted aryl, and optionally substituted heteroaryl.

In some variations, the MEK inhibitor compound is of the formula (VI), or a pharmaceutically acceptable salt or ester thereof, wherein the variables are as defined in WO 2009/021887 A1 for the formula I or any applicable variations described on pages 4-5 in WO 2009/021887 A1, incorporated herein by reference. Further embraced MEK inhibitors are compounds described in Examples 1-21 in 2009/021887 A1, incorporated herein by reference.

In some embodiments, the MEK inhibitor compound of the formula (VI) is a compound selected from the group consisting of:
(R)-5-[4-(2-Hydroxy-ethoxy)-phenyl]-3-[(S)-1-(6-iodo-1H-benzoimidazol-2-yl)-2-phenyl-ethyl]-imidazolidine-2,4-dione;
(R)-5-[4-(2-Hydroxy-ethoxy)-phenyl]-3-(5-iodo-1H-benzoimidazol-2-ylmethyl)-imidazolidine-2,4-dione;
(R)-5-[4-(2-Hydroxy-ethoxy)-phenyl]-3-[(S)-1-(5-iodo-1H-benzoimidazol-2-yl)-2-methyl-propyl]-imidazolidine-2,4-dione;
(R)-5-[4-(2-Hydroxy-ethoxy)-phenyl]-3-[(1R,2R)-1-(5-iodo-1H-benzoimidazol-2-yl)-2-methoxy-propyl]-imidazolidine-2,4-dione;
3-[(S)-1-(5-Iodo-1H-benzoimidazol-2-yl)-2-phenyl-ethyl]-imidazolidine-2,4-dione; compound with trifluoro-acetic acid;
(R)-3-[(S)-2-(4-Fluoro-phenyl)-1-(5-iodo-1H-benzoimidazol-2-yl)-ethyl]-5-[4-(2-hydroxy-ethoxy)-phenyl]-imidazolidine-2,4-dione;
(R)-5-[4-(2-Hydroxy-ethoxy)-phenyl]-3-[(S)-1-(5-iodo-H-benzoimidazol-2-yl)-2-(4-methoxy-phenyl)-ethyl]-imidazolidine-2,4-dione;
(R)-5-[4-(2-Hydroxy-ethoxy)-phenyl]-3-[(S)-1-(5-iodo-1H-benzoimidazol-2-yl)-2-thiophen-2-yl-ethyl]-imidazolidine-2,4-dione;
(R)-3-[(1S,2S)-1-(6-Iodo-1H-benzoimidazol-2-yl)-2-phenyl-propyl]-5-phenyl-imidazolidine-2,4-dione;
(R)-3-[(1S,2S)-1-(6-Iodo-1H-benzoimidazol-2-yl)-2-phenyl-propyl]-5-(4-methoxy-phenyl)-imidazolidine-2,4-dione;
(R)-5-[4-(2-Hydroxy-ethoxy)-phenyl]-3-[(1S,2S)-1-(6-iodo-1H-benzoimidazol-2-yl)-2-phenyl-propyl]-imidazolidine-2,4-dione;
(R)-3-[(1S,2S)-1-(6-Iodo-1H-benzoimidazol-2-yl)-2-phenyl-propyl]-5-[4-(2-methoxy-ethoxy)-phenyl]-imidazolidine-2,4-dione;
2-(4-{(R)-1-[(1S,2S)-1-(6-Iodo-1H-benzoimidazol-2-yl)-2-phenyl-propyl]-2,5-dioxo-imidazolidin-4-yl}-phenoxy)-N,N-dimethyl-acetamide;
N,N-Bis-(2-hydroxy-ethyl)-2-(4-{(R)-1-[(1S,2S)-1-(6-iodo-1H-benzoimidazol-2-yl)-2-phenyl-propyl]-2,5-dioxo-imidazolidin-4-yl}-phenoxy)-acetamide;
(R)-3-[(1S,2S)-1-(5-Iodo-1H-benzoimidazol-2-yl)-2-phenyl-propyl]-5-isopropyl-imidazolidine-2,4-dione;
(R)-5-Cyclohexyl-3-[(1S,2S)-1-(5-iodo-1H-benzoimidazol-2-yl)-2-phenyl-propyl]-imidazolidine-2,4-dione;
(R)-5-[4-(2-Hydroxy-ethoxy)-phenyl]-3-[1-(5-iodo-1H-benzoimidazol-2-yl)-cyclopropyl]-imidazolidine-2,4-dione;
(R)-3-[(1S,2S)-1-(6-Bromo-1H-benzoimidazol-2-yl)-2-phenyl-propyl]-5-[4-(2-hydroxy-ethoxy)-phenyl]-imidazolidine-2,4-dione;
(R)-3-[(S)-1-(5-Cyclopropyl-1H-benzoimidazol-2-yl)-2-phenyl-ethyl]-5-[4-(2-hydroxy-ethoxy)-phenyl]-imidazolidine-2,4-dione;
(R)-3-[(S)-1-(5-Ethynyl-1H-benzoimidazol-2-yl)-2-phenyl-ethyl]-5-[4-(2-hydroxy-ethoxy)-phenyl]-imidazolidine-2,4-dione; and
(R)-3-[(1S,2S)-1-(5-Ethynyl-1H-benzoimidazol-2-yl)-2-phenyl-propyl]-5-[4-(2-hydroxy-ethoxy)-phenyl]-imidazolidine-2,4-dione;

or a pharmaceutically acceptable salt or solvate thereof.

In some embodiments, the MEK inhibitor is a compound selected from the group consisting of GDC-0973 (Methanone, [3,4-difluoro-2-[(2-fluoro-4-iodophenyl)amino]phenyl][3-hydroxy-3-(2S)-2-piperidinyl-1-azetidinyl]-), G-38963, G02443714, G02442104, and G00039805, or a pharmaceutically acceptable salt or solvate thereof.

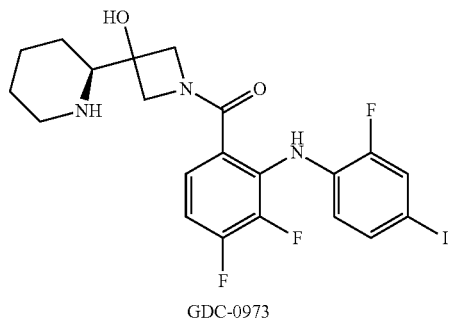

GDC-0973

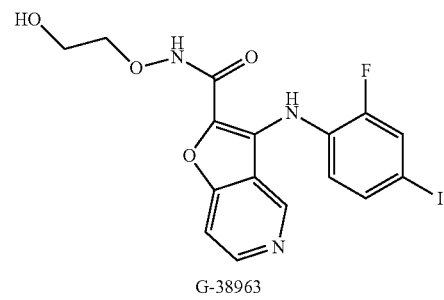

G-38963

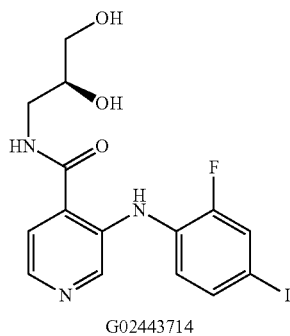

G02443714

-continued

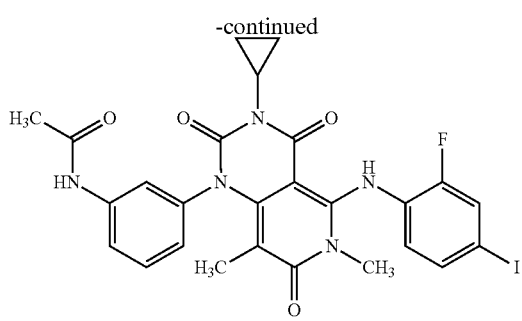

G02442104

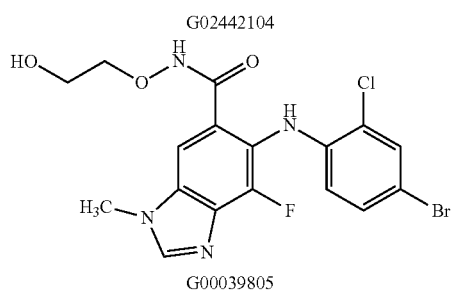

G00039805

IV Kits

In another aspect, provided herein is a kit comprising a PD-L1 axis binding antagonist and/or a MEK inhibitor for treating or delaying progression of a cancer in an individual or for enhancing immune function of an individual having cancer. In some embodiments, the kit comprises a PD-1 axis binding antagonist and a package insert comprising instructions for using the PD-1 axis binding antagonist in combination with a MEK inhibitor to treat or delay progression of cancer in an individual or to enhance immune function of an individual having cancer. In some embodiments, the kit comprises a MEK inhibitor and a package insert comprising instructions for using the MEK inhibitor in combination with a PD-1 axis binding antagonist to treat or delay progression of cancer in an individual or to enhance immune function of an individual having cancer. In some embodiments, the kit comprises a PD-1 axis binding antagonist and a MEK inhibitor, and a package insert comprising instructions for using the PD-1 axis binding antagonist and the MEK inhibitor to treat or delay progression of cancer in an individual or to enhance immune function of an individual having cancer. Any of the PD-1 axis binding antagonists and/or MEK inhibitors described herein may be included in the kits.

In some embodiments, the kit comprises a container containing one or more of the PD-1 axis binding antagonists and MEK inhibitors described herein. Suitable containers include, for example, bottles, vials (e.g., dual chamber vials), syringes (such as single or dual chamber syringes) and test tubes. The container may be formed from a variety of materials such as glass or plastic. In some embodiments, the kit may comprise a label (e.g., on or associated with the container) or a package insert. The label or the package insert may indicate that the compound contained therein may be useful or intended for treating or delaying progression of cancer in an individual or for enhancing immune function of an individual having cancer. The kit may further comprise other materials desirable from a commercial and user standpoint, including other buffers, diluents, filters, needles, and syringes.

Examples

The invention can be further understood by reference to the following examples, which are provided by way of illustration and are not meant to be limiting.

Example 1: Combination Treatment with an Anti-PDL1 Antibody and a MEK Inhibitor Causes Sustained Tumor Regression in Vemurafenib-Progressing Tumors While B-raf inhibition (such as by treatment with Vemurafenib) is effective in eliciting short-term tumor regression, resistance is frequently observed. This Example describes the finding that treatment with a combination of a PD-1 axis binding antagonist and a MEK inhibitor induces sustained tumor regression and increased progression-free survival in animals with Vemurafenib-progressing tumors. Moreover, treatment with a combination of a PD-1 axis binding antagonist and a MEK inhibitor was surprisingly superior to treatment with either agent individually.

Materials and Methods
Mouse Model

A melanoma GEM model B-raf$^{V600E}$; PTEN$^{fl/fl}$; TyCreER was used. B-raf$^{V600E}$ and TyCreER alleles were as described in Dankort, D., et al. Nat. Genet. 41(5):544-52 (2009). The PTEN conditional allele was as described in Lesche, R. et al. genesis 32:148-9 (2002).

Tumor Initiation

Tumors were initiated by application of tamoxifen as described in Dankort, D., et al. Nat. Genet. 41(5):544-52 (2009). Animals were enrolled into the study once their tumors reached a size greater than or equal to 400 mm$^3$.

Treatments

Prior to beginning treatment, each mouse received a biopsy of a melanoma tumor. After the biopsy, mice were allowed to recover for up to one week prior to receiving treatment. Mice were assigned into initial treatment groups (n=20), and treatment commenced at day 0.

For Vemurafenib treatment, mice were given either MCT, 200 µL, PO, qd; or PLX-4032 (Vemurafenib), 50 mg/kg PO, BID (volume not to exceed 300 µL). When animals in any group reached ~2000 mm$^3$, the tumors were biopsied a second time. After the biopsy procedure, mice recovered for up to one week prior to receiving further therapeutic treatment. The animals were then re-assigned to the following treatment groups: GDC-0973 (Cobimetinib), 7.5 mg/kg PO, qd (volume not to exceed 300 µL)+Ragweed Control (IgG2a), 10 mg/kg IP, three times weekly; GDC-0973, 7.5 mg/kg PO, qd (volume not to exceed 300 µL)+anti-PDL1 (IgG1-WT), 10 mg/kg IP, three times weekly; or MCT, 200 uL, PO, qd+anti-PDL1 (IgG1-WT), 10 mg/kg IP, three times weekly. IP dose volume did not exceed 300 µL.

Mice were weighed and tumors measured at least once a week until study termination. Mice received treatment each day until a mean tumor volume of 2500 mm$^3$ was achieved. Mice were then euthanized, and melanoma tumors were collected for histology and assessing molecular changes. Mice were perfused under anesthesia at euthanasia.

Throughout the study, mice were monitored for clinical appearance (body condition, coat appearance, posture, labored breathing, etc.) at least 2 times a week, with increasing frequency, up to daily, depending on severity of adverse clinical signs observed. Moribund animals were euthanized. Mice with a body condition score <2 were euthanized.

Results

Upon tumor induction, the melanoma GEM model B-raf$^{V600E}$; PTEN$^{fl/fl}$; TyCreER causes tumors that show an initial regression in size upon treatment with the B-raf inhibitor Vemurafenib. After this initial regression, the tumors display steady re-growth, thereby modeling resistance to B-raf inhibition in Vemurafenib-progressing tumors.

This model was used to test the efficacy of PD-1 axis binding antagonists and MEK inhibitors as a 2$^{nd}$ line therapy for Vemurafenib-progressing tumors. As shown in FIG. 1, after first line treatment with Vemurafenib, animals were treated with an antibody against PD-L1, a MEK inhibitor (Cobimetinib), or both. Treatment with anti-PD-L1 alone showed no effect on tumor growth. Treatment with Cobimetinib caused an initial tumor regression, but this response was not sustained and tumor re-growth was observed. Combination treatment with anti-PD-L1 and Cobimetinib, however, caused regression in every tumor, and this regression was sustained. In addition, intratumoral GR1 levels were significantly reduced, and a signature of T cell activation was observed (e.g., increased CD8, PRF1, and MHC I). Importantly, treatment with anti-PD-L1 and Cobimetinib led to increased progression-free survival (PFS).

Figure 2:
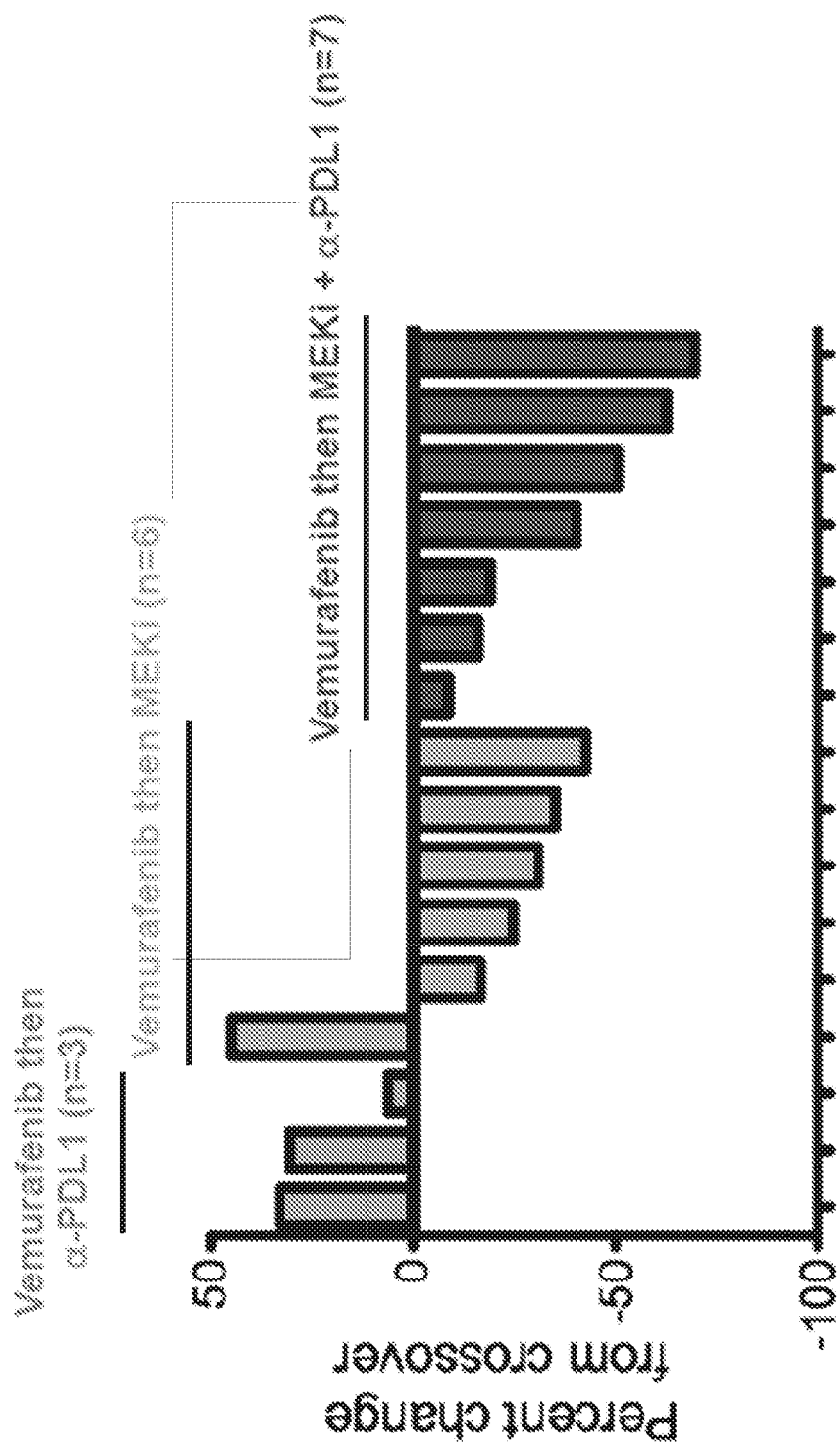
FIG. 2 shows individual animal responses to treatment with Vemurafenib followed by anti-PDL1, a MEK inhibitor, or both. Each bar depicts the percent change in tumor growth upon crossover from Vemurafenib to the indicated treatment in an individual animal.

FIG. 2 shows individual animal responses following crossover from Vemurafenib to anti-PD-L1, Cobimetinib, or combination treatment.

These results demonstrate that combined treatment with a PD-1 axis binding antagonist and a MEK inhibitor leads to dramatic, sustained tumor regression in Vemurafenib-progressing tumors, as compared to treatment with each agent alone. Moreover, these results demonstrate the superior efficacy of combined PD-1 axis/MEK inhibition as a 2$^{nd}$ line treatment for tumors resistant to B-raf inhibition.

All patents, patent applications, documents, and articles cited herein are herein incorporated by reference in their entireties.

What is claimed is:

1. A method for treating or delaying progression of a melanoma that is resistant to a B-raf antagonist in an individual, the method comprising administering to the individual an effective amount of a PD-L1 binding antagonist and a MEK inhibitor, wherein:
the individual has been previously treated with the B-raf antagonist for melanoma and the melanoma is resistant to the B-raf antagonist,
the MEK inhibitor is GDC-0973 or a pharmaceutically acceptable salt or solvate thereof, and
the PD-L1 antagonist is an anti-PD-L1 antibody comprising a heavy chain comprising HVR-H1 sequence of SEQ ID NO: 15, HVR-H2 sequence of SEQ ID NO: 16, and HVR-H3 sequence of SEQ ID NO: 3; and a light chain comprising HVR-L1 sequence of SEQ ID NO: 17, HVR-L2 sequence of SEQ ID NO: 18, and HVR-L3 sequence of SEQ ID NO: 19.

2. The method of claim 1, further comprising diagnosing the individual as having a melanoma that is resistant to the B-raf antagonist, wherein the diagnosing occurs prior to administering the effective amount of the PD-L1 binding antagonist and the MEK inhibitor.

3. The method of claim 1, wherein the melanoma in the individual has progressed within 1 month, 6 months, 1 year, or 5 years after completing a B-raf antagonist-based therapy regimen.

4. The method of claim 1, wherein the B-raf antagonist is a small molecule inhibitor.

5. The method of claim 4, wherein the B-raf antagonist is dabrafenib, vemurafenib, GSK 2118436, RAF265, XL281, ARQ736, BAY73-4506, sorafenib, PLX4720, PLX-3603, GSK2118436, GDC-0879, or N-(3-(5-(4-chlorophenyl)-1H-pyrrolo[2,3-b]pyridine-3-carbonyl)-2,4-difluorophenyl)propane-1-sulfonamide.

6. The method of claim 4, wherein the B-raf antagonist is a selective B-raf antagonist of B-raf V600.

7. The method of claim 6, wherein the selective B-raf antagonist of B-raf V600 is a selective antagonist of B-raf V600E.

8. The method of claim 6, wherein the selective B-raf antagonist of B-raf V600 is a selective antagonist of B-raf V600E, B-raf V600K, and/or V600D.

9. The method of claim 6, wherein the selective B-raf antagonist of B-raf V600 is a selective antagonist of B-raf V600R.

10. The method of claim 1, wherein the melanoma contains a BRAF V600E mutation, a BRAF wildtype, a KRAS wildtype, or an activating KRAS mutation.

11. The method of claim 1, wherein the treatment results in a sustained response in the individual after cessation of the treatment.

12. The method of claim 1, wherein the melanoma is metastatic.

13. The method of claim 1, wherein the PD-L1 binding antagonist inhibits the binding of PD-L1 to PD-1, PD-L1 to B7-1, or PD-L1 to both PD-1 and B7-1.

14. The method of claim 1, wherein the anti-PD-L1 antibody is a monoclonal antibody.

15. The method of claim 1, wherein the anti-PD-L1 antibody is an antibody fragment selected from the group consisting of Fab, Fab'-SH, Fv, scFv, and F(ab')$_2$ fragments.

16. The method of claim 1, wherein the anti-PD-L1 antibody is a humanized antibody.

17. The method of claim 1, wherein the PD-L1 binding antagonist is YW243.55.S70 or atezolizumab.

18. The method of claim 1, wherein the anti-PD-L1 antibody comprises a heavy chain variable region comprising the amino acid sequence of SEQ ID NO: 24 and a light chain variable region comprising the amino acid sequence of SEQ ID NO: 21.

19. The method of claim 1, wherein the MEK inhibitor is administered continuously.

20. The method of claim 1, wherein the MEK inhibitor is administered intermittently.

21. The method of claim 1, wherein the MEK inhibitor is administered before the PD-L1 binding antagonist.

22. The method of claim 1, wherein the MEK inhibitor is administered simultaneously with the PD-L1 binding antagonist.

23. The method of claim 1, wherein the MEK inhibitor is administered after the PD-L1 binding antagonist.

24. The method of claim 1, wherein the PD-L1 binding antagonist and/or the MEK inhibitor is administered intravenously, intramuscularly, subcutaneously, topically, orally, transdermally, intraperitoneally, intraorbitally, by implantation, by inhalation, intrathecally, intraventricularly, or intranasally.

* * * * *